United States Patent
Du et al.

(10) Patent No.: US 9,840,498 B2
(45) Date of Patent: Dec. 12, 2017

(54) SUBSTITUTED QUINAZOLIN-4-ONE DERIVATIVES

(71) Applicants: NOVARTIS AG, Basel (CH); Zhenxing Du, Shanghai (CN); Samuel Hintermann, Basel (CH); Konstanze Hurth, Lorrach (DE); Sebastien Jacquier, Hegenheim (FR); Hansjoerg Lehmann, Basel (CH); Henrik Moebitz, Freiburg (DE); Nicolas Soldermann, Village-Neuf (FR); Aleksandar Stojanovic, Basel (CH)

(72) Inventors: Zhenxing Du, Shanghai (CN); Samuel Hintermann, Basel (CH); Konstanze Hurth, Lorrach (DE); Sébastien Jacquier, Hegenheim (FR); Hansjoerg Lehmann, Basel (CH); Henrik Moebitz, Freiburg (DE); Nicolas Soldermann, Village-Neuf (FR); Aleksandar Stojanovic, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/907,225

(22) PCT Filed: Jul. 24, 2014

(86) PCT No.: PCT/CN2014/082946
§ 371 (c)(1),
(2) Date: Jan. 22, 2016

(87) PCT Pub. No.: WO2015/010641
PCT Pub. Date: Jan. 29, 2015

(65) Prior Publication Data
US 2016/0168131 A1  Jun. 16, 2016

(30) Foreign Application Priority Data

Jul. 24, 2013  (EP) .................................. 13177827

(51) Int. Cl.
| C07D 403/14 | (2006.01) |
| C07D 401/14 | (2006.01) |
| C07D 417/14 | (2006.01) |
| C07D 473/16 | (2006.01) |
| A61K 31/517 | (2006.01) |
| A61K 31/52 | (2006.01) |

(52) U.S. Cl.
CPC .......... *C07D 403/14* (2013.01); *A61K 31/517* (2013.01); *A61K 31/52* (2013.01); *C07D 401/14* (2013.01); *C07D 417/14* (2013.01); *C07D 473/16* (2013.01)

(58) Field of Classification Search
CPC .................................................. C07D 401/12
See application file for complete search history.

(56) References Cited

U.S. PATENT DOCUMENTS

| 3,301,855 A | 1/1967 | Blatter |
| 6,518,277 B1 | 2/2003 | Sadhu et al. |
| 6,667,300 B2 | 12/2003 | Sadhu et al. |
| 6,800,620 B2 | 10/2004 | Sadhu et al. |
| 6,949,535 B2 | 9/2005 | Sadhu et al. |
| 7,932,260 B2 | 4/2011 | Fowler et al. |
| 2002/0151544 A1 | 10/2002 | Hayakawa et al. |
| 2002/0161014 A1 | 10/2002 | Sadhu et al. |
| 2005/0043239 A1 | 2/2005 | Douangpanya et al. |
| 2005/0261319 A1 | 11/2005 | Deuschle et al. |

FOREIGN PATENT DOCUMENTS

| CN | 102838600 A | 12/2012 |
| CN | 102838601 A | 12/2012 |
| EP | 2612861 A2 | 7/2013 |
| WO | 01/70737 A2 | 9/2001 |
| WO | 01/81346 A2 | 11/2001 |
| WO | 02/26718 A2 | 4/2002 |
| WO | 03/035075 A1 | 5/2003 |
| WO | 03/066603 A1 | 8/2003 |
| WO | 03/076418 A1 | 9/2003 |
| WO | 2004/009036 A2 | 1/2004 |

(Continued)

OTHER PUBLICATIONS

Pinedo et al (2000).*
McMahon et al. (2000).*
Okkenhaug K. et al., PI3K in lymphocyte development, differentiation and activation; Nature Reviews Immunology. Apr. 2003; 3:317-330.
Marone R. et al., Targeting phosphoinositide 3-kinase—Moving towards therapy; Biochimica et Biophysica Acta (BBA)—Proteins and Proteomics. Jan. 2008; 1784(1): 159-185.
Okkenhaug K. et al., Impaired B and T Cell Antigen Receptor Signaling in p110δ PI 3-Kinase Mutant Mice. Science. Aug. 2002; 297: 1031-1034.
Martin F. et al, B Cell Immunobiology in Disease: Evolving Concepts from the Clinic. Annual Review of Immunology. Apr. 2006; 24:467-496.
Ghigo A. et al., PI3K inhibition in inflammation: Toward tailored therapies for specific diseases. BioEssays. Mar. 2010; 32(3):185-196.

(Continued)

*Primary Examiner* — Paul V Ward
(74) *Attorney, Agent, or Firm* — Laura K. Madden

(57) ABSTRACT

Provided are substituted quinazolin-4-one compounds of the formula (I) and/or pharmaceutically acceptable salts and/or solvates thereof, wherein $R^1$, $R^2$, $R^3$, $R^5$, $R^6$ and L are as defined in the description. Such compounds are suitable for the treatment of a disorder or disease which is mediated by the activity of the class I PI3K kinases.

(I)

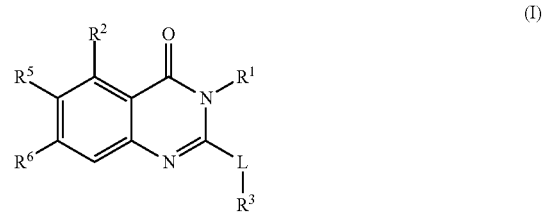

15 Claims, 1 Drawing Sheet

(56) References Cited

FOREIGN PATENT DOCUMENTS

| | | |
|---|---|---|
| WO | 2004/034972 A2 | 4/2004 |
| WO | 2004/087053 A2 | 10/2004 |
| WO | 2005/016348 A1 | 2/2005 |
| WO | 2005/016349 A1 | 2/2005 |
| WO | 2005/067901 A2 | 7/2005 |
| WO | 2005/091711 A2 | 10/2005 |
| WO | 2005/112935 A1 | 12/2005 |
| WO | 2005/113554 A2 | 12/2005 |
| WO | 2005/113556 A1 | 12/2005 |
| WO | 2005/117889 A1 | 12/2005 |
| WO | 2005/120511 A1 | 12/2005 |
| WO | 2005/123694 A2 | 12/2005 |
| WO | 2006/004915 A1 | 1/2006 |
| WO | 2006/089106 A2 | 8/2006 |
| WO | 2007/065662 A2 | 6/2007 |
| WO | 2007/114926 A2 | 10/2007 |
| WO | 2008/064018 A1 | 5/2008 |
| WO | 2008/064244 A2 | 5/2008 |
| WO | 2008/071974 A2 | 6/2008 |
| WO | 2008/076447 A2 | 6/2008 |
| WO | 2008/127226 A2 | 10/2008 |
| WO | 2009/036768 A2 | 3/2009 |
| WO | 2009/058361 A1 | 5/2009 |
| WO | 2009/088986 A1 | 7/2009 |
| WO | 2009/088990 A1 | 7/2009 |
| WO | 2010/057048 A1 | 5/2010 |
| WO | 2010/059593 A1 | 5/2010 |
| WO | 2010/065923 A2 | 6/2010 |
| WO | 2010/083163 A1 | 7/2010 |
| WO | 2010/111432 A1 | 9/2010 |
| WO | 2010/123931 A1 | 10/2010 |
| WO | 2011/011550 A1 | 1/2011 |
| WO | 2011/031896 A2 | 3/2011 |
| WO | 2011/056930 A2 | 5/2011 |
| WO | 2011/082285 A1 | 7/2011 |
| WO | 2011/146882 A1 | 11/2011 |
| WO | 2012/073184 A1 | 6/2012 |
| WO | 2013/012915 A1 | 1/2013 |
| WO | 2013/032591 A1 | 3/2013 |
| WO | 2013/154878 A1 | 10/2013 |
| WO | 2014/014814 A1 | 1/2014 |
| WO | 2014/015523 A1 | 1/2014 |
| WO | 2014/100765 A1 | 6/2014 |
| WO | 2014/100767 A1 | 6/2014 |
| WO | 2014/128612 A1 | 8/2014 |

OTHER PUBLICATIONS

Reif K. et al., Cutting Edge: Differential Roles for Phosphoinositide 3-Kinases, p110γ and p110δ, in Lymphocyte Chemotaxis and Homing. The Journal of Immunology. Aug. 2004; 173(4): 2236-2240.
Laffargue M. et al., Phosphoinositide 3-Kinase γ Is an Essential Amplifier of Mast Cell Function. Immunity. Mar. 2002; 16(3): 441-451.
Gerard C. et al.., Chemokines and disease. Nature Immunology. Feb. 2001; 2(2):108-115.
Liu L. et al. ,Leukocyte PI3Kγ and PI3Kδ have temporally distinct roles for leukocyte recruitment in vivo. Blood. Aug. 2007; 110(4): 1191-1198.
Maira S.-M. et al., Class IA phosphatidylinositol 3-kinase: from their biologic implication in human cancers to drug discovery. Expert Opinion in Therapeutic Targets. Feb. 2008; 12(2): 223-238.
Foukas L.C. et al.; Critical role for the p110α phosphoinositide-3-OH kinase in growth and metabolic regulation. Nature. May 2006; 441: 366-370.
Schofield L. et al., Immunological processes in malaria pathogenesis. Nature Reviews Immunology. Sep. 2005; 5: 722-735.
Schofield L. et al., Intravascular infiltrates and organ-specific inflammation in malaria pathogenesis. Immunology and Cell Biology. Feb. 2007; 85(2):130-137.
Mishra B.B. et al., Toll-Like Receptors in CNS Parasitic Infections. Current Topics in Microbiology and Immunology.Feb. 2009; 336: 83-104.
Bottieau E. et al., Therapy of vector-borne protozoan infections in nonendemic settings. Expert Review of Anti-Infective Therapy. May 2011; 9(5); 583-608.
Hedayat M. et al., Targeting of Toll-like receptors: a decade of progress in combating infectious diseases. The Lancet Infectious Diseases. Sep. 2011; 11(9): 702-712.
Kawai T. et al., Toll-like Receptors and Their Crosstalk with Other Innate Receptors in Infection and Immunity. Immunity. May 2011; 34(5); 637-650.
Higgins S. J. et al., Immunopathogenesis of falciparum malaria: implications for adjunctive therapy in the management of severe and cerebral malaria. Expert review of anti-infective therapy. Sep. 2011; 9(9): 803-819.
Gowda N. M. et al., The Nucleosome Is the TLR9-Specific Immunostimulatory Component of Plasmodium falciparum That Activates DCs. PLoS One. Jun. 2011; 6(6): 1-14.
Peixoto-Rangel et al., Candidate gene analysis of ocular toxoplasmosis in Brazil: evidence for a role for toll-like receptor 9 (TLR9). Memórias do Instituto Oswaldo Cruz. Dec. 2009; 104(8): 1187-1190.
Pellegrini A. et al., The role of Toll-like receptors and adaptive immunity in the development of protective or Pathological immune response triggered by the Trypanosoma cruzi protozoan. Future Microbiology. Dec. 2011; 6 (12):1521-1533.
Franklin B. S. et al., Therapeutical targeting of nucleic acid-sensing Toll-like receptors prevents experimental cerebral malaria. PNAS. Mar. 2011; 108(9): 3689-3694.
Arevalo J.F. et al., Ocular Toxoplasmosis in the Developing World. International Ophthalmology Clinics. 2010; 50(2): 57-69.
Dan S. et al., Correlating phosphatidylinositol 3-kinase inhibitor efficacy with signaling pathway status: in silico and biological evaluations. Cancer Research. Jun. 2010; 70(12):4982-4994.
Sabbah D.A. et al., Docking studies on isoform-specific inhibition of phosphoinositide-3-kinases. Journal of chemical information and modeling. Oct. 25, 2010;50(10):1887-1898.
Berndt A. et al., The p110δ structure: Mechanisms for selectivity and potency of new PI(3)K inhibitors. Nature Chemical Biology. Feb. 6, 2010:117-124.
Williams O. et al., Discovery of dual inhibitors of the immune cell PI3Ks p110δ and p110γ: a prototype for new anti-inflammatory drugs. Chemistry & Biology. Feb. 2010; 17(2)123-134.
Frederick R. et al., Phosphoinositide-3-kinase (PI3K) inhibitors: Identification of new scaffolds using virtual screening. Bioorganic & Medicinal Chemistry Letters. Oct. 2009: 19(20):5842-5847.
Niedermeier M. et al., Isoform-selective phosphoinositide 3'-kinase inhibitors inhibit CXCR4 signaling and overcome stromal cell-mediated drug resistance in chronic lymphocytic leukemia: a novel therapeutic approach. Blood. May 2009; 113(22):5549-5557.
Billottet C. et al.; Inhibition of class I phosphoinositide 3-kinase activity impairs proliferation and triggers apoptosis in acute promyelocytic leukemia without affecting atra-induced differentiation. Cancer Research, Feb. 2009, 69(3):1027-1036.
Apsel B. et al., Targeted polypharmacology: discovery of dual inhibitors of tyrosine and phosphoinositide kinases. Nature chemical biology. Nov. 2008; 4(11):691-699.
Zhan T.-T. et al., Genetic or pharmaceutical blockade of p110δ phosphoinositide 3-kinase enhances IgE production. Journal of Allergy and Clinical Immunology. Oct. 2008; 122(4): 811-819.
Park S. et al., PI-103, a dual inhibitor of Class IA phosphatidylinositide 3-kinase and mTOR, has antileukemic activity in AML. Leukemia. Sep. 2008;22(9):1698-1706.
Zvelebil M. J. et al., Structural analysis of PI3-kinase isoforms: Identification of residues enabling selective inhibition by small molecule ATP-competitive inhibitors. Archives of Biochemistry and Biophysics. Sep. 2008; 477(2):404-410.
Tamburini J.et al., Mammalian target of rapamycin (mTOR) inhibition activates phosphatidylinositol 3-kinase/Akt by up-regulating insulin-like growth factor-1 receptor signaling in acute myeloid leukemia: rationale for therapeutic inhibition of both pathways. Blood. Jan. 2008; 111(1):379-382.
Chaussade C. et al., Evidence for functional redundancy of class IA PI3K isoforms in insulin signalling. Biochemical Journal. Jun. 2007; 404(Pt 3): 449-458.

(56) References Cited

OTHER PUBLICATIONS

Billottet C. et al.; A selective inhibitor of the p110 delta isoform of PI 3-kinase inhibits AML cell proliferation and survival and increases the cytotoxic effects of VP16. Oncogene; May 2006; 25 (50): 6648-6659.

Wolff M. et al., Automated High Content Screening for Phosphoinositide 3 Kinase Inhibition Using an AKT1 Redistribution Assay. Combinatorial Chemistry & High Throughput Screening. Jun. 2006; 9(5):339-350.

Knight Z.A. et al., A Pharmacological Map of the PI3-K Family Defines a Role for p110α in Insulin Signaling. Cell. May 2006; 125(4):733-747.

Fan Q. W. et al, A dual PI3 kinase/mTOR inhibitor reveals emergent efficacy in glioma. Cancer Cell. May 2006;9(5):341-349.

Kuang R.R. et al., Action mechanisms and structure-activity relationships of PI3Kgamma inhibitors on the enzyme: a molecular modeling study. European journal of medicinal chemistry. Apr. 2006; 41(4):558-65.

Kuang R.R. et al.; Study on improving the selectivity of compounds that inhibit two PI3Ks (gamma and delta). Journal of molecular modeling. Mar. 2006;12(4):445-452.

Xue S. et al., A facile synthesis of C2,N3-disubstituted-4-quinazolone.The Journal of organic chemistry. Sep. 2004; 69(19):6474-7.

Puri K. D., Mechanisms and implications of phosphoinositide 3-kinase delta in promoting neutrophil trafficking into inflamed tissue. Blood. May 2004; 103(9):3448-56.

Feng J. et al., Discovery of Alogliptin: A Potent, Selective, Bioavailable, and Efficacious Inhibitor of Dipeptidyl Peptidase IV. Journal of Medicinal Chemistry. Apr. 2007, 50(10):2297-2300.

Noel R. et al., N-Methyldihydroquinazolinone Derivatives of Retro-2 with Enhanced Efficacy against Shiga Toxin. Journal of Medicinal Chemistry. Mar. 2013; 56 (8): 3404-3413.

Rommel et al.: "PI3Kδ and PI3Kγ: partners in crime in inflammation in rheumatoid arthritis and beyond?", Nature Reviews, Immunology, vol. 7, 2007, pp. 191-201.

\* cited by examiner

SUBSTITUTED QUINAZOLIN-4-ONE DERIVATIVES

This application is a U.S. National Phase filing of International Application No. PCT/CN2014/082946 filed 24 Jul. 2014, which claims priority to EP Application No. 13177827.6 filed 24 Jul. 2013, the contents of which are incorporated herein by reference in their entirety.

FIELD OF THE INVENTION

The present invention relates to the preparation and use of new substituted quinazolin-4-one derivatives as drug candidates in free form or in pharmaceutically acceptable salt form with valuable druglike properties, such as e.g. metabolic stability and suitable pharmacokinetics, form for the modulation, notably the inhibition of the activity or function of the phosphoinositide 3' OH kinase family (hereinafter PI3K).

BACKGROUND OF THE INVENTION

Members of the phosphoinositide-3 kinase (PI3K) family are involved in cell growth, differentiation, survival, cytoskeletal remodeling and the trafficking of intracellular organelles in many different types of cells (Okkenhaug and Wymann, Nature Rev. Immunol. 3:317 (2003).

To date, eight mammalian PI3Ks have been identified, divided into three main classes (I, II and III) on the basis of their genetic sequence, structure, adapter molecules, expression, mode of activation, and preferred substrate.

The most widely understood class I family (comprising isoforms PI3K α, β, γ and δ) is further subdivided into subclasses IA and IB. Class IA PI3 kinases (isoforms PI3Kα, PI3Kβ and PI3Kδ) consist of an 85 kDa regulatory/adapter protein and three 110 kDa catalytic subunits (p110α, p110β and p110δ) which are activated in the tyrosine kinase system whilst class IB consists of a single p110γ isoform (PI3Kγ) which is activated by G protein-coupled receptors.

PI3Kδ and PI3Kγ are both lipid kinases belonging to the class I PI3K family (PI3K α, β, γ and δ). PI3Kδ generates second messenger signals downstream of tyrosine kinase-linked receptors while PI3Kγ is primarily activated by G protein-coupled receptors (GPCR).

PI3Kδ and PI3Kγ are heterodimers composed of an adaptor protein and a p110δ or p110γ catalytic subunit, respectively, which converts phosphatidylinositol-4,5-bisphosphate (PtdlnsP2) to phosphatidylinositol-3,4,5-tri-phosphate (PtdlnsP3). Effector proteins interact with PtdlnsP3 and trigger specific signaling pathways involved in cell activation, differentiation, migration, and cell survival.

Expression of the p110δ and p110γ catalytic subunits is preferential to leukocytes. Expression is also observed in smooth muscle cells, myocytes and endothelial cells. In contrast, p110α and p110β are expressed by all cell types (Marone et al. Biochimica et Biophysica Acta 1784:159 (2008)).

PI3Kδ is associated with B cell development and function (Okkenhaug et al. Science 297:1031 (2002)).

B cells play also a critical role in the pathogenesis of a number of autoimmune and allergic diseases as well as in the process of transplant rejection (Martin and Chan, Annu. Rev. Immunol. 24:467 (2006)).

A link between PI3Kγ and processes such as leukocyte chemotaxis and mast cell degranulation has been shown, thereby generating interest in this target for the treatment of autoimmune and inflammatory disorders (Ghigo et al., Bioessays, 2010, 32, 185-196; Reif et al., J. Immunol., 2004, 173, 2236-2240; Laffargue et al., Immunity, 2002, 16, 441-451). There are also reports linking PI3Kγ to cancer, diabetes, cardiovascular disease, and Alzheimer's disease.

Chemotaxis is involved in many autoimmune or inflammatory diseases, in angiogenesis, invasion/metastasis, neurodegeneration or wound healing (Gerard et al. Nat. Immunol. 2:108 (2001)). Temporarily distinct events in leukocyte migration in response to chemokines are fully dependent on PI3Kδ and PI3Kγ (Liu et al. Blood 110:1191 (2007)).

PI3Kα and PI3Kβ play an essential role in maintaining homeostasis and pharmacological inhibition of these molecular targets has been associated with cancer therapy (Maira et al. Expert Opin. Ther. Targets 12:223 (2008)).

PI3Kα is involved in insulin signaling and cellular growth pathways (Foukas et al. Nature 441:366 (2006)). PI3Kδ and/or PI3Kγ isoform-selective inhibition is expected to avoid potential side effects such as hyperglycemia, and metabolic or growth disregulation.

Parasitic infections still represent one of the most important causes of morbidity and mortality worldwide. Among the parasites that cause human and animal pathology the phylum apicomplexa comprises a group of vector-borne parasites that is responsible for a wide variety of serious illnesses including but not limited to malaria, leishmaniasis and trypanosomiasis. Malaria alone infects 5-10% of humanity and causes around two million deaths per year. [Schofield et al, "Immunological processes in malaria pathogenesis", Nat Rev Imm 2005], [Schofiled L, "Intravascular infiltrates and organ-specific inflammation in malaria pathogenesis], [Mishra et al, "TLRs in CNS Parasitic infections", Curr Top Micro Imm 2009], [Bottieau et al, "Therapy of vector-borne protozoan infections in nonendemic settings", Expert Rev. Anti infect. Ther., 2011].

Toll-like receptors (TLRs) are germ-line encoded, phylogenetically ancient molecules that recognize evolutionary conserved structural relevant molecules (known as pathogen-associated molecular patterns (PAMPs)) within microbial pathogens. Various different cell types including cells of the immune system express TLRs and are thereby able to detect the presence of PAMPs. Sofar 10 functional TLR family members (TLR1-10) have been described in humans, all of which recognize specific PAMP molecules. Following recognition of these specific PAMPs TLRs induce and orchestrate the immuneresponse of the host to infections with bacteria, viruses, fungi and parasites. [Hedayat et al, "Targeting of TLRs: a decade of progress in combating infectious disease", review, Lancet Infectious disease 2011], [Kwai et al, "TLRs and their crosstalk with other innate receptors in infection and immunity", review, Immunity May-2011].

The immune system of the infected host responds to infection with the TLR induced production of pro-inflammatory cytokines mainly of the T-helper 1 type (Th1). While adequate amounts of these cytokines are beneficial and required to clear the infection an overproduction of these mediators is harmful to the host and associated with immune mediated pathology including neuropathology and tissue damage with severe and often fatal consequences. One prominent and highly relevant example of such immune mediated pathology is acute and cerebral malaria (CM) which causes severe clinical symptoms and is often fatal. [Schofield et al, "Immunological processes in malaria pathogenesis", Nat Rev Imm 2005], [Schofiled L, "Intravascular infiltrates and organ-specific inflammation in malaria pathogenesis], [Mishra et al, "TLRs in CNS Parasitic infections", Curr Top Micro Imm 2009], [Bottieau et al, "Therapy of vector-borne protozoan infections in nonendemic settings", Expert Rev. Anti infect. Ther., 2011] [Hedayat et al, "Targeting of TLRs: a decade of progress in combating infectious disease", review, Lancet Infectious disease 2011]. Despite progress made in treatment and eradication of malaria, the mortality rate that is associated with severe malaria, including CM remains unacceptably high. Strategies directed solely at the eradication of the parasite in the host might therefore not be sufficient to prevent neurological complications and death in all cases of CM. Development of new innovative adjunct therapeutic strategies to efficiently reduce the CM-associated mortality and morbidity that is caused, in part, by host-mediated immunopathology remains therefore an urgent medical need. [Higgins et al, "Immunopathogenesis of falciparum malaria: implications for adjunctive therapy in the management of severe and cerebral malaria", Expert Rev. Anti Infect. Ther. 2011]

Recently further evidence has been provided that TLR9 plays a key role in the recognition and response to parasites including but not limited to Plasmodium, Leishmania, Trypanosoma and Toxoplasma [Gowda et al, "The Nucleosome is the TLR9-specific Immunostimulatory component of plasmodium falciparum that activates DCs", PLoS ONE, June 2011], [Peixoto-Rangel et al, "Candidate gene analysis of ocular toxoplasmosis in Brazil: evidence for a role for TLR9", Mem Inst Oswaldo Cruz 2009], [Pellegrini et al, "The role of TLRs and adoptive immunity in the development of protective or pathological immune response triggered by the Trypanosoma cruzi protozoan", Future Microbiol 2011] and that interference with the activation of TLRs including TLR9 represents a promising strategy to prevent the deleterious inflammatory responses in severe and cerebral malaria [Franklin et al, "Therapeutical targeting of nucleic acid-sensing TLRs prevents experimental cerebral malaria", PNAS 2011]

Malaria is an infectious disease caused by four protozoan parasites: Plasmodium falciparum; Plasmodium vivax; Plasmodium ovale; and Plasmodium malaria. These four parasites are typically transmitted by the bite of an infected female Anopheles mosquito. Malaria is a problem in many parts of the world and over the last few decades the malaria burden has steadily increased. An estimated 1-3 million people die every year from malaria—mostly children under the age of 5. This increase in malaria mortality is due in part to the fact that Plasmodium falciparum, the deadliest malaria parasite, has acquired resistance against nearly all available antimalarial drugs, with the exception of the artemisinin derivatives.

Leishmaniasis is caused by one or more than 20 varieties of parasitic protozoa that belong to the genus Leishmania, and is transmitted by the bite of female sand flies. Leishmaniasis is endemic in about 88 countries, including many tropical and sub-tropical areas. There are four main forms of Leishmaniasis. Visceral leishmaniasis, also called kala-azar, is the most serious form and is caused by the parasite Leishmania donovani. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the Trypanosoma Genus. They are transmitted to humans by tsetse fly (Glossina Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite Trypanosoma cruzi, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal. The drugs currently available for treating Chagas disease are Nifurtimox and benznidazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

Toxoplasmosis is endemic in many areas globally and can infect a large proportion of the adult population. However, its prevalence differs in different countries. It is estimated to infect at least 10% of adults in northern temperate countries and more than half of adults in Mediterranean and tropical countries. Toxoplasma gondii, the causative pathogen of toxoplamosis, is a ubiquitous, obligate intracellular protozoan and is considered to be the most common cause of infective retinitis in humans, which depends on a variety of factors, including climate, hygiene, and dietary habits. The course of disease in immunocompetent adults is usually asymptomatic
and self-limiting. As soon as infection has occurred, the parasite forms latent cysts in the retina and in other organs of the body, which can reactivate years after the initial infection giving rise to acute retinochoroiditis and the formation of new retinochoroidal lesions. [Arevalo et al, "Ocular Toxoplasmosis in the developing world", Internat. Ophthal. Clin 2010]

Neurocysticercosis is the most common parasitic disease of the CNS (incidence ~2.5 million worldwide) caused by the larvae of Taenia solium. The disease has a long asymptomatic phase in humans characterized by the absence of a detectable inflammatory response surrounding the parasite. The overall immune response during the asymptomatic phase is of the Th2 phenotype. However, the destruction of larvae by therapeutic treatment or by normal parasite attrition causes a strong inflammatory response, often consisting of a chronic granulomatous reaction and manifestation of typical symptoms of the disease. The immune response in the CNS of symptomatic patients consists of an overt Th1 phenotype or a mixed Th1, Th2, and Th3 response, depending upon the absence or presence of granulomas. The hyperinflammatory response prevailing during the symptomatic phase in the CNS is responsible for the severe neuropathology and mortality associated with neurocysticercosis. [Mishra et al, "TLRs in CNS Parasitic infections", Curr Top Micro Imm 2009]

SUMMARY OF THE INVENTION

There is a need to provide new class I PI3 kinase inhibitors that are good drug candidates. In particular, compounds of the invention should bind potently to class I PI3 kinases whilst showing little affinity for other receptors and show functional activity as inhibitors. They should be well absorbed from the gastrointestinal tract, be metabolically stable and possess favourable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

The compounds of the invention show a certain level of selectivity against the different paralogs PI3K α, β, γ and δ. In particular, show a certain level of selectivity for the isoforms PI3Kδ and PI3Kγ over the PI3Kα isoform.

The compounds of the present invention are therefore potentially useful in the treatment of a wide range of disorders, particularly disorders including but not limited to autoimmune disorders, autoinflammatory and inflammatory diseases, allergic diseases, disease or infection associated immunopathologies, airway diseases, such as asthma and COPD, transplant rejection, cancers eg of hematopoietic origin or solid tumors.

Various embodiments of the invention are described herein.

Within certain aspects, provided herein is a compound of formula (I) or a pharmaceutically acceptable salt thereof:

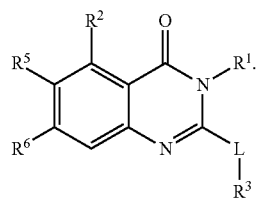

(I)

In another embodiment, the invention provides a pharmaceutical composition comprising a therapeutically effective amount of a compound according to the definition of formula (I), or a pharmaceutically acceptable salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae thereof and one or more therapeutically active agent.

In another embodiment, the invention also relates to the treatment, either alone or in combination, with one or more other pharmacologically active compounds, including methods of treating conditions, diseases or disorders in which one or more of the functions of B cells such as antibody production, antigen presentation, cytokine production or lymphoid organogenesis are abnormal or are undesirable including rheumatoid arthritis and related diseases (such as ankylosing spondylarthritis, psoriatic arthritis, juvenile arthritis), pemphigus vulgaris and related diseases, idiopathic thrombocytopenic purpura, systemic lupus erythematosus, multiple sclerosis, myasthenia gravis, Sjögren's syndrome (such as primary Sjögren's syndrome (pSS)), Graft versus host disease, autoimmune hemolytic anemia, ANCA-associated vasculitides (such as Wegener disease, microscopic polyangiitis or Churg-Strauss syndrome), cryoglobulinemia, thrombotic thrombocytopenic purpura, ischemia-reperfusion injury, chronic autoimmune urticaria, allergy (atopic dermatitis, contact dermatitis, allergic rhinitis, allergic asthma, asthma associated with allergic rhinitis), asthma, Goodpasture's syndrome, different types of glomerulonephritides, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease as well as in disease or infection associated immunopathology.

DETAILED DESCRIPTION OF THE INVENTION

Figure 1:
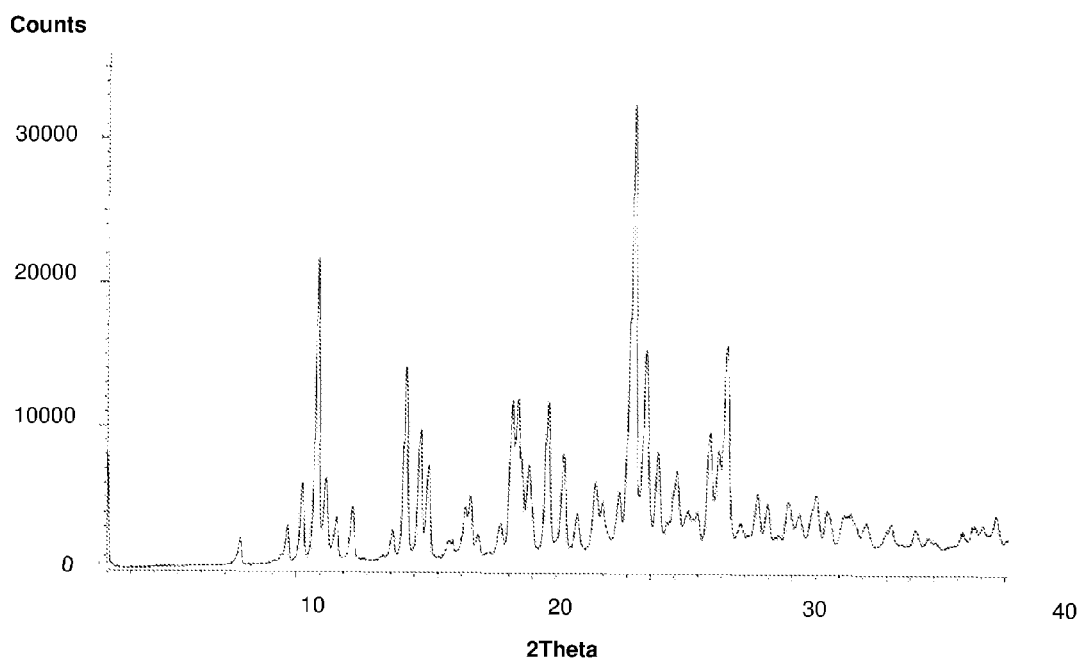
FIG. 1 is the X-ray Powder Diffraction Pattern of the crystalline form of Example 7
Figure 2:
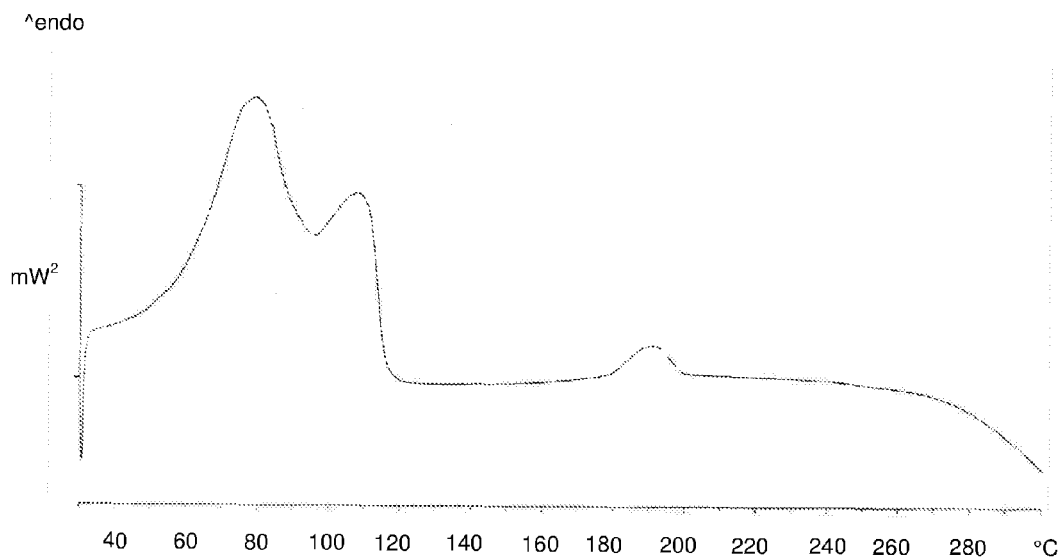
FIG. 2 is the Differential scanning calorimetry (DSC) thermogram of the crystalline form of Example 7

The invention provides substituted quinazolin-4-one compounds of the formula (I) and/or pharmaceutically acceptable salts and/or solvates thereof,

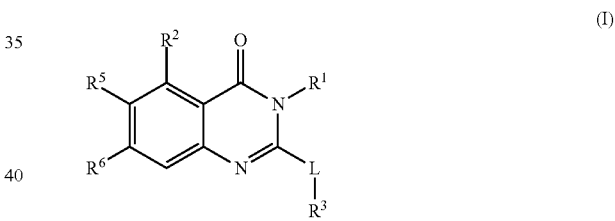

(I)

wherein,
$R^1$ is selected from
phenyl, which is unsubstituted or substituted by 1, 2 or 3 substituents independently selected from
  methyl, ethyl, difluoromethyl, methoxy, difluoromethoxy, cyclopropyl, chloro or fluoro;
pyridyl, which is unsubstituted or substituted by 1, 2 or 3 substituents independently selected from
  methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein C$_4$-C$_7$-heteroaryl is unsubstituted or substituted by 1-3 substituents independently selected from
  C$_1$-C$_4$-alkyl,
  C$_1$-C$_4$-fluoroalkyl,
  hydroxy-C$_1$-C$_4$-alkyl,
  hydroxy-C$_1$-C$_4$-fluoroalkyl,
  C$_1$-C$_4$-alkoxy,
  C$_1$-C$_4$-fluoroalkoxy,
  C$_3$-C$_6$-cycloalkyl, which is unsubstituted or substituted by 1-3 substituents independently selected from methyl, or fluoro,
  C$_3$-C$_6$-heterocycloalkyl, which is unsubstituted or substituted by 1-3 substituents independently selected from methyl, or fluoro,
  cyano,
  fluoro,
  amino,
  C$_1$-C$_4$-alkylamino, or
  C$_1$-C$_4$-dialkylamino;
or
C$_2$-C$_5$-alkynyl, which is unsubstituted or substituted by 1-2 substituents independently selected from
  C$_1$-C$_4$-fluoroalkyl,
  C$_3$-C$_6$-cycloalkyl, which is unsubstituted or substituted by 1-3 substituents independently selected from methyl, or fluoro,
  C$_3$-C$_6$-heterocycloalkyl, which is unsubstituted or substituted by 1-3 substituents independently selected from methyl, or fluoro,
  C$_1$-C$_4$-alkoxy,
  C$_1$-C$_4$-fluoroalkoxy,
  hydroxyl,
  cyano,
  fluoro,
  amino,
  C$_1$-C$_4$-alkylamino, or
  C$_1$-C$_4$-dialkylamino;
R$^5$ and R$^6$ are independently selected from hydrogen, deuterium or fluoro;
-L-R$^3$ is selected from

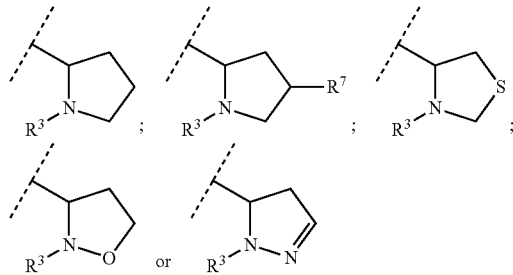

wherein
R$^7$ is selected from methoxy, difluoromethoxy, trifluoromethoxy, hydroxy, fluoro or methylsulfonylamine; and
R$^3$ is selected from

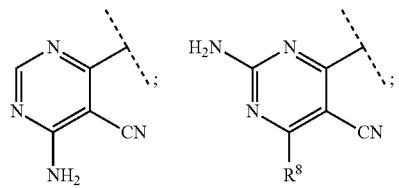

-continued

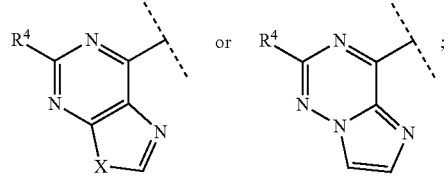

wherein
R$^4$ is selected from hydrogen or amino,
R$^8$ is selected from hydrogen, methyl, fluoromethyl, difluoromethyl, trideuteromethyl or amino, and
X is selected from NH, NMe or S.

Unless specified otherwise, the term "compounds of the present invention" refers to compounds of formula (I) and subformulae thereof, salts of the compound, as well as all stereoisomers (including diastereoisomers and enantiomers), rotamers, tautomers and isotopically labeled compounds (including deuterium substitutions, as well as inherently formed moieties). Where compounds of formula (I) are mentioned, this is meant to include also the tautomers and N-oxides of the compounds of formula (I).

The invention may be more fully appreciated by reference to the following description, including the following glossary of terms and the concluding examples. As used herein, the terms "including", "containing" and "comprising" are used herein in their open, non-limiting sense.

Tautomers, such as tautomers between purine forms can be present for example in the R$^3$ portion of compounds of formula (I). Nitrogen containing heterocyclyl and heteroaryl residues may form N-oxides, for examples in the R$^2$ position of compounds of formula (I).

Where the plural form is used for compounds, salts, and the like, this is taken to mean also a single compound, salt, or the like.

The general terms used hereinbefore and hereinafter preferably have within the context of this disclosure the following meanings, unless otherwise indicated:

As used herein, the term "C$_3$-C$_6$-cycloalkyl" refers to a 3 to 6 membered monocyclic saturated ring.

In the context of R$^1$, examples of C$_3$-C$_6$-cycloalkyl include cyclopropyl; cyclobutyl; cyclopentyl and cyclohexyl;

in the context of R$^1$, examples of C$_3$-C$_6$-cycloalkyl which is substituted in the 1 position by methyl include 1-methylcyclopropyl; 1-methylcyclobutyl; 1-methylcyclopentyl and 1-methylcyclohexyl;

in the context of R$_2$, examples of C$_3$-C$_6$-cycloalkyl as substituent on heteroaryl or alkynyl includes cyclopropyl and cyclobutyl.

As used herein, the term "C$_3$-C$_6$-heterocycloalkyl" refers to a 3 to 6 membered monocyclic saturated ring containing 1, 2 or 3 heteroatoms selected from N, O or S.

In the context of R$_2$, examples of C$_3$-C$_6$-heterocycloalkyl as substituent on heteroaryl or alkynyl includes oxetan, aziridine and morpholine.

As used herein, the term "C$_4$-C$_7$-heteroaryl" refers to a 4 to 7 membered monocyclic ring with maximum saturation containing one nitrogen atom and additional 0, 1, 2 or 3 heteroatoms independently selected from N, O or S.

In the context of R$^2$, examples of C$_4$-C$_7$-heteroaryl include pyrazole, imidazole, pyridine, pyrimidine, isoxazole, thiazole, pyridazine, pyrazine, oxazole, isothiazole, thiophene, furan, triazole, tetrazole.

As used herein, the term "$C_1$-$C_4$-dialkylamino" is amino substituted with two alkyl groups which are independently selected from $C_1$-$C_4$-alkyl.

As used herein, the term "$C_1$-$C_4$-fluoroalkyl" refers to $C_1$-$C_4$-alkyl which is partially or fully fluorinated.

As used herein, the term "$C_1$-$C_4$-fluoroalkoxy" refers to $C_1$-$C_4$-alkoxy which is partially or fully fluorinated.

As used herein, all substituents are written in a way to show the order of functional groups (groups) they are composed of. The functional groups are defined herein above.

Various embodiments of the invention are described herein. It will be recognized that features specified in each embodiment may be combined with other specified features to provide further embodiments of the present invention.

In one embodiment, the invention provides a compound of the formula (I) and/or a pharmaceutically acceptable salt thereof, selected from a compound of the formula (I')

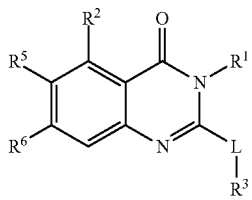

(I')

wherein,
$R^1$ is selected from
phenyl, which is unsubstituted or substituted by 1, 2 or 3 substituents independently selected from
  methyl, ethyl, difluoromethyl, methoxy, difluoromethoxy, cyclopropyl, chloro or fluoro;
pyridyl, which is unsubstituted or substituted by 1, 2 or 3 substituents independently selected from
  methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is $C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
  $C_1$-$C_4$-alkyl,
  $C_1$-$C_4$-fluoroalkyl,
  hydroxy-$C_1$-$C_4$-alkyl,
  hydroxy-$C_1$-$C_4$-fluoroalkyl,
  $C_1$-$C_4$-alkoxy,
  $C_1$-$C_4$-fluoroalkoxy,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  cyano,
  fluoro,
  amino,
  $C_1$-$C_4$-alkylamino, or
  $C_1$-$C_4$-dialkylamino;
$R^5$ and $R^6$ are independently selected from hydrogen, deuterium or fluoro;
-L-$R^3$ is selected from

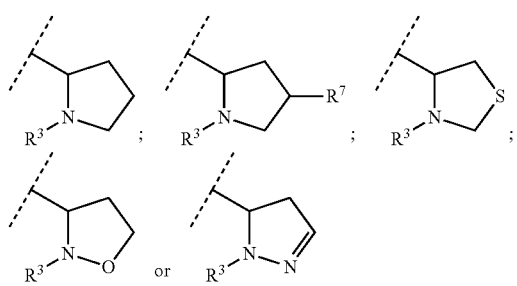

wherein
$R^7$ is selected from methoxy, difluoromethoxy, trifluoromethoxy, hydroxy, fluoro or methylsulfonylamine; and
$R^3$ is selected from

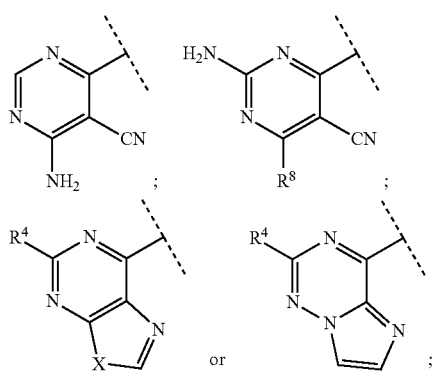

wherein
$R^4$ is selected from hydrogen or amino,
$R^8$ is selected from hydrogen, methyl, fluoromethyl, difluoromethyl, trideuteromethyl or amino, and
X is selected from NH, NMe or S.

In another embodiment, the invention provides a compound of the formula (I) and/or a pharmaceutically acceptable salt thereof, selected from a compound of the formula (I")

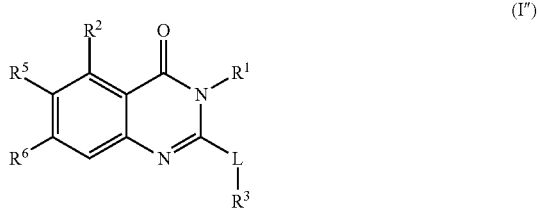

(I")

wherein,

R¹ is selected from phenyl, which is unsubstituted or substituted by 1, 2 or 3 substituents independently selected from
- methyl, ethyl, difluoromethyl, methoxy, difluoromethoxy, cyclopropyl, chloro or fluoro;

pyridyl, which is unsubstituted or substituted by 1, 2 or 3 substituents independently selected from
- methyl, ethyl, difluoromethyl, methoxy, difluoromethoxy, cyclopropyl, chloro or fluoro;

1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;

R² is
$C_2$-$C_5$-alkynyl, which is unsubstituted or substituted by 1-2 substituents independently selected from
- $C_1$-$C_4$-fluoroalkyl,
- $C_3$-$C_6$-cycloalkyl, which is unsubstituted or substituted by 1-3 substituents independently selected from methyl, or fluoro,
- $C_3$-$C_6$-heterocycloalkyl, which is unsubstituted or substituted by 1-3 substituents independently selected from methyl, or fluoro,
- $C_1$-$C_4$-alkoxy,
- $C_1$-$C_4$-fluoroalkoxy,
- hydroxy,
- cyano,
- fluoro,
- amino,
- $C_1$-$C_4$-alkylamino, or
- $C_1$-$C_4$-dialkylamino;

R⁵ and R⁶ are independently selected from hydrogen, deuterium or fluoro;

-L-R³ is selected from

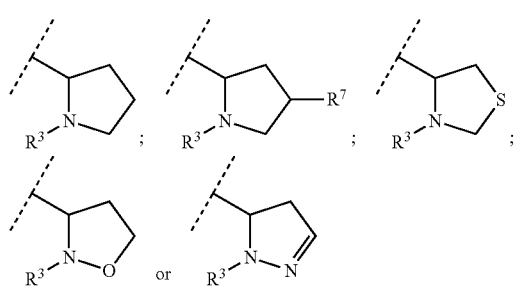

wherein
R⁷ is selected from methoxy, difluoromethoxy, trifluoromethoxy, hydroxy, fluoro or methylsulfonylamine; and R³ is selected from

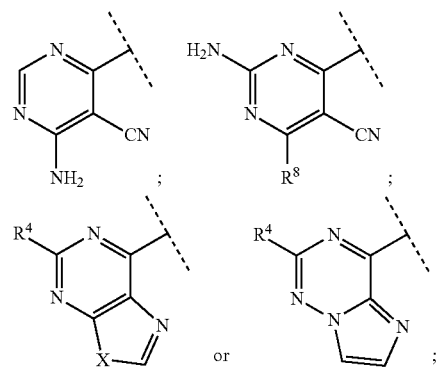

wherein
R⁴ is selected from hydrogen or amino,
R⁸ is selected from hydrogen, methyl, fluoromethyl, difluoromethyl, trideuteromethyl or amino, and
X is selected from NH, NMe or S.

In another embodiment, the invention provides a compound of the formula (I) and/or a pharmaceutically acceptable salt thereof, selected from a compound of the formula (Ia)

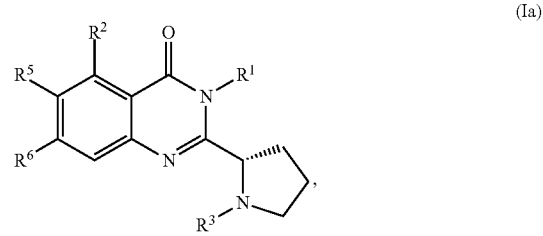

(Ia)

wherein
R¹ is selected from
phenyl, which is unsubstituted or substituted by 1, 2 or 3 substituents independently selected from
- methyl, ethyl, difluoromethyl, methoxy, difluoromethoxy, cyclopropyl, chloro or fluoro;

pyridyl, which is unsubstituted or substituted by 1, 2 or 3 substituents independently selected from
- methyl, ethyl, difluoromethyl, methoxy, difluoromethoxy, cyclopropyl, chloro or fluoro;

1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;

R² is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
- $C_1$-$C_4$-alkyl,
- $C_1$-$C_4$-fluoroalkyl,
- hydroxy-$C_1$-$C_4$-alkyl, hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
cyano,
fluoro,
amino,
$C_1$-$C_4$-alkylamino, or
$C_1$-$C_4$-dialkylamino;
or
$C_2$-$C_5$-alkynyl, which is unsubstituted or substituted by 1-2 substituents independently selected from
$C_1$-$C_4$-fluoroalkyl,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
$C_1$-$C_4$-alkoxy,
$C_1$-$C_4$-fluoroalkoxy,
hydroxy,
cyano,
fluoro,
amino,
$C_1$-$C_4$-alkylamino, or
$C_1$-$C_4$-dialkylamino;
$R^5$ and $R^6$ are independently selected from hydrogen, deuterium or fluoro; and
$R^3$ is selected from

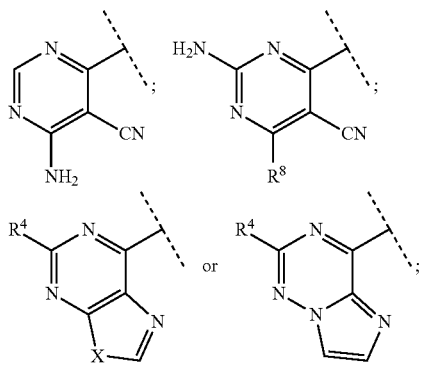

wherein
$R^4$ is selected from hydrogen or amino,
$R^8$ is selected from hydrogen, methyl, fluoromethyl, difluoromethyl, trideuteromethyl or amino, and
X is selected from NH, NMe or S.

In another embodiment, the invention provides a compound of the formula (I) and/or a pharmaceutically acceptable salt thereof, selected from a compound of the formula (Ib)

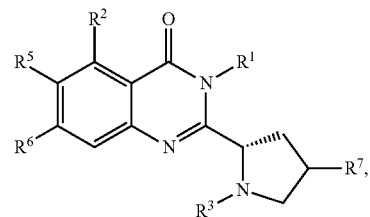

(Ib)

wherein
$R^1$ is selected from
phenyl, which is unsubstituted or substituted by 1, 2 or 3 substituents independently selected from
methyl, ethyl, difluoromethyl, methoxy, difluoromethoxy, cyclopropyl, chloro or fluoro;
pyridyl, which is unsubstituted or substituted by 1, 2 or 3 substituents independently selected from
methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
cyano,
fluoro,
amino,
$C_1$-$C_4$-alkylamino, or
$C_1$-$C_4$-dialkylamino;
or
$C_2$-$C_5$-alkynyl, which is unsubstituted or substituted by 1-2 substituents independently selected from
$C_1$-$C_4$-fluoroalkyl,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
$C_1$-$C_4$-alkoxy,
$C_1$-$C_4$-fluoroalkoxy, hydroxy,
cyano,
fluoro,
amino,
$C_1$-$C_4$-alkylamino, or
$C_1$-$C_4$-dialkylamino;
$R^5$ and $R^6$ are independently selected from hydrogen, deuterium or fluoro;
$R^7$ is selected from methoxy, difluoromethoxy, trifluoromethoxy, hydroxy, fluoro or methylsulfonylamine; and
$R^3$ is selected from

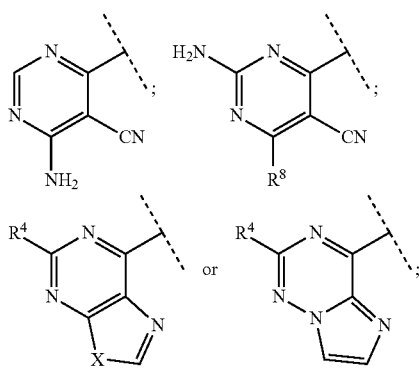

wherein
$R^4$ is selected from hydrogen or amino,
$R^8$ is selected from hydrogen, methyl, fluoromethyl, difluoromethyl, trideuteromethyl or amino, and
X is selected from NH, NMe or S.

In one embodiment, the invention provides a compound of the formula (I) and/or a pharmaceutically acceptable salt thereof, selected from a compound of the formula (IA)

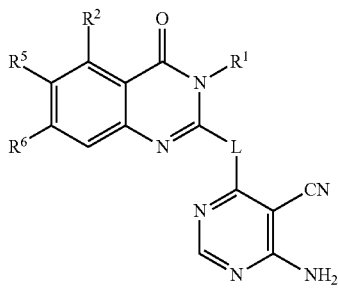

(IA)

wherein,
$R^1$ is selected from
phenyl, which is unsubstituted or substituted by 1, 2 or 3 substituents independently selected from
  methyl, ethyl, difluoromethyl, methoxy, difluoromethoxy, cyclopropyl, chloro or fluoro;
pyridyl, which is unsubstituted or substituted by 1, 2 or 3 substituents independently selected from
  methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
  $C_1$-$C_4$-alkyl,
  $C_1$-$C_4$-fluoroalkyl,
  hydroxy-$C_1$-$C_4$-alkyl,
  hydroxy-$C_1$-$C_4$-fluoroalkyl,
  $C_1$-$C_4$-alkoxy,
  $C_1$-$C_4$-fluoroalkoxy,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  cyano,
  fluoro,
  amino,
  $C_1$-$C_4$-alkylamino, or
  $C_1$-$C_4$-dialkylamino;
or
$C_2$-$C_5$-alkynyl, which is unsubstituted or substituted by 1-2 substituents independently selected from
  $C_1$-$C_4$-fluoroalkyl,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  $C_1$-$C_4$-alkoxy,
  $C_1$-$C_4$-fluoroalkoxy,
  hydroxy,
  cyano,
  fluoro,
  amino,
  $C_1$-$C_4$-alkylamino, or
  $C_1$-$C_4$-dialkylamino;
$R^5$ and $R^6$ are independently selected from hydrogen, deuterium or fluoro;
-L-$R^3$ is selected from

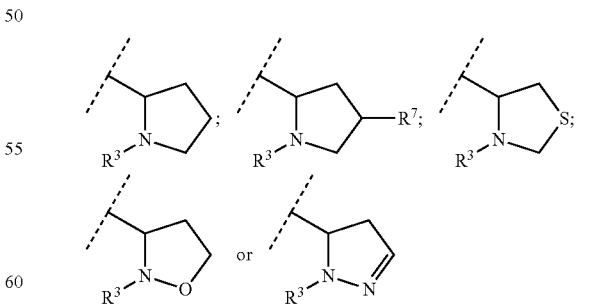

wherein
$R^7$ is selected from methoxy, difluoromethoxy, trifluoromethoxy, hydroxy, fluoro or methylsulfonylamine; and
$R^3$ is attached to L via the trivalent nitrogen atom.

In another embodiment, the invention provides a compound of the formula (I) and/or a pharmaceutically acceptable salt thereof, selected from a compound of the formula (IB)

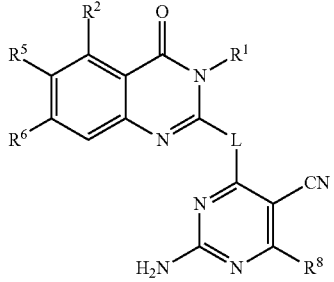

(IB)

wherein,
R¹ is selected from
phenyl, which is unsubstituted or substituted by 1, 2 or 3 substituents independently selected from
   methyl, ethyl, difluoromethyl, methoxy, difluoromethoxy, cyclopropyl, chloro or fluoro;
pyridyl, which is unsubstituted or substituted by 1, 2 or 3 substituents independently selected from
   methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
R² is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
   $C_1$-$C_4$-alkyl,
   $C_1$-$C_4$-fluoroalkyl,
   hydroxy-$C_1$-$C_4$-alkyl,
   hydroxy-$C_1$-$C_4$-fluoroalkyl,
   $C_1$-$C_4$-alkoxy,
   $C_1$-$C_4$-fluoroalkoxy,
   $C_3$-$C_6$-cycloalkyl, which is unsubstituted or substituted by 1-3 substituents independently selected from methyl, or fluoro,
   $C_3$-$C_6$-heterocycloalkyl, which is unsubstituted or substituted by 1-3 substituents independently selected from methyl, or fluoro,
   cyano,
   fluoro,
   amino,
   $C_1$-$C_4$-alkylamino, or
   $C_1$-$C_4$-dialkylamino;
or
$C_2$-$C_5$-alkynyl, which is unsubstituted or substituted by 1-2 substituents independently selected from
   $C_1$-$C_4$-fluoroalkyl,
   $C_3$-$C_6$-cycloalkyl, which is unsubstituted or substituted by 1-3 substituents independently selected from methyl, or fluoro,
   $C_3$-$C_6$-heterocycloalkyl, which is unsubstituted or substituted by 1-3 substituents independently selected from methyl, or fluoro,
   $C_1$-$C_4$-alkoxy,
   $C_1$-$C_4$-fluoroalkoxy,
   hydroxy,
   cyano,
   fluoro,
   amino,
   $C_1$-$C_4$-alkylamino, or
   $C_1$-$C_4$-dialkylamino;
R⁵ and R⁶ are independently selected from hydrogen, deuterium or fluoro;
R⁸ is selected from hydrogen, methyl, fluoromethyl, difluoromethyl, trideuteromethyl or amino;
-L-R³ is selected from

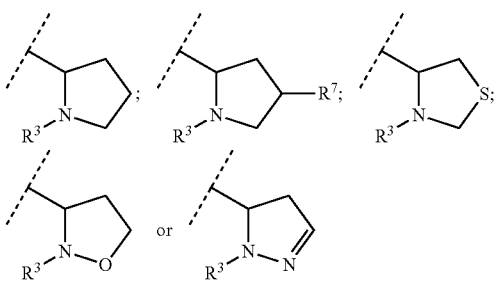

wherein
R⁷ is selected from methoxy, difluoromethoxy, trifluoromethoxy, hydroxy, fluoro or methylsulfonylamine; and
R³ is attached to L via the trivalent nitrogen atom.

In another embodiment, the invention provides a compound of the formula (I) and/or a pharmaceutically acceptable salt thereof, selected from a compound of the formula (IC)

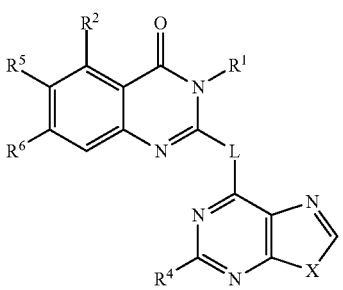

(IC)

wherein,
R¹ is selected from
phenyl, which is unsubstituted or substituted by 1, 2 or 3 substituents independently selected from
   methyl, ethyl, difluoromethyl, methoxy, difluoromethoxy, cyclopropyl, chloro or fluoro;
pyridyl, which is unsubstituted or substituted by 1, 2 or 3 substituents independently selected from
   methyl, ethyl, difluoromethyl, methoxy, difluoromethoxy, cyclopropyl, chloro or fluoro;

1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
  $C_1$-$C_4$-alkyl,
  $C_1$-$C_4$-fluoroalkyl,
  hydroxy-$C_1$-$C_4$-alkyl,
  hydroxy-$C_1$-$C_4$-fluoroalkyl,
  $C_1$-$C_4$-alkoxy,
  $C_1$-$C_4$-fluoroalkoxy,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  cyano,
  fluoro,
  amino,
  $C_1$-$C_4$-alkylamino, or
  $C_1$-$C_4$-dialkylamino;
or
$C_2$-$C_5$-alkynyl, which is unsubstituted or substituted by 1-2 substituents independently selected from
  $C_1$-$C_4$-fluoroalkyl,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  $C_1$-$C_4$-alkoxy,
  $C_1$-$C_4$-fluoroalkoxy,
  hydroxy,
  cyano,
  fluoro,
  amino,
  $C_1$-$C_4$-alkylamino, or
  $C_1$-$C_4$-dialkylamino;
$R^5$ and $R^6$ are independently selected from hydrogen, deuterium or fluoro;
$R^4$ is selected from hydrogen or amino;
X is selected from NH, NMe or S;
-L- is selected from

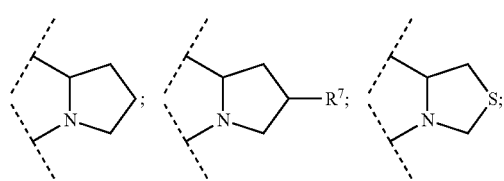

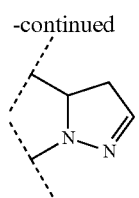

wherein
$R^7$ is selected from methoxy, difluoromethoxy, trifluoromethoxy, hydroxy, fluoro or methylsulfonylamine; and
$R^3$ is attached to L via the trivalent nitrogen atom.

In one embodiment, the invention provides a compound of the formulae (I) or (I'), (I''), (IA), (IB) or (IC) and/or a pharmaceutically acceptable salt thereof, wherein
-L-$R^3$ is selected from

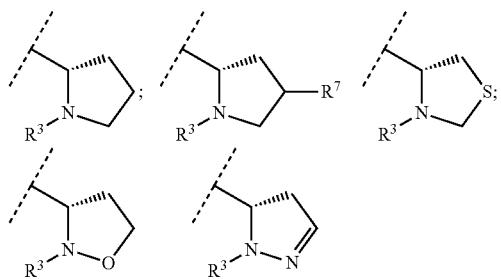

wherein
$R^7$ is selected from methoxy, difluoromethoxy, trifluoromethoxy, hydroxy, fluoro or methylsulfonylamine.

In another embodiment, the invention provides a compound of the formulae (I) or (I'), (I''), (IA), (IB) or (IC) and/or a pharmaceutically acceptable salt thereof, wherein
-L-$R^3$ is selected from

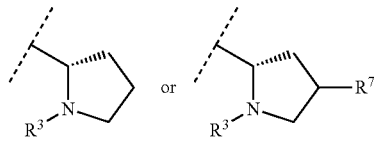

wherein
$R^7$ is selected from methoxy, hydroxyl or fluoro.

In another embodiment, the invention provides a compound of the formulae (I) or (I'), (I''), (IA), (IB) or (IC) and/or a pharmaceutically acceptable salt thereof, wherein
-L-$R^3$ is selected from

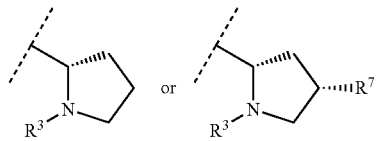

wherein
$R^7$ is selected from methoxy, hydroxyl or fluoro.

In one embodiment, the invention provides a compound of the formulae (I) or (I'), (Ia), (Ib), (IA), (IB) or (IC) and/or a pharmaceutically acceptable salt thereof, wherein $R^5$ is selected from hydrogen or fluoro; and
$R^6$ is selected from hydrogen.

In one embodiment, the invention provides a compound of the formulae (I) or (I'), (Ia), (Ib), (IA), (IB) or (IC) and/or a pharmaceutically acceptable salt thereof, wherein
$R^2$ is $C_5$-$C_6$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro.

In another embodiment, the invention provides a compound of the formulae (I) or (I'), (Ia), (Ib), (IA), (IB) or (IC) and/or a pharmaceutically acceptable salt thereof, wherein
$R^2$ is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro.

In another embodiment, the invention provides a compound of the formulae (I) or (I'), (Ia), (Ib), (IA), (IB) or (IC) and/or a pharmaceutically acceptable salt thereof, wherein
$R^2$ is selected from pyrazole, imidazole, pyridine, pyrimidine, isoxazole, thiazole, oxazole or isothiazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro.

In another embodiment, the invention provides a compound of the formulae (I) or (I'), (Ia), (Ib), (IA), (IB) or (IC) and/or a pharmaceutically acceptable salt thereof, wherein
$R^2$ is selected from pyrazole, imidazole, pyridine, pyrimidine, isoxazole or thiazole, which is unsubstituted or substituted by 1 substituent independently selected from
$C_1$-$C_4$-alkyl,
hydroxy-$C_1$-$C_4$-alkyl, or
$C_1$-$C_4$-alkoxy.

In one embodiment, the invention provides a compound of the formulae (I) or (I''), (Ia), (Ib), (IA), (IB) or (IC) and/or a pharmaceutically acceptable salt thereof, wherein
$R^2$ is $C_2$-$C_5$-alk-1-ynyl, which is unsubstituted or substituted by 1-2 substituents independently selected from
$C_1$-$C_4$-fluoroalkyl,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
$C_1$-$C_4$-alkoxy,
$C_1$-$C_4$-fluoroalkoxy,
hydroxy, or
fluoro.

In another embodiment, the invention provides a compound of the formulae (I) or (I''), (Ia), (Ib), (IA), (IB) or (IC) and/or a pharmaceutically acceptable salt thereof, wherein
$R^2$ is $C_2$-$C_5$-alk-1-ynyl, which is substituted by 1 substituent selected from hydroxy.

In another embodiment, the invention provides a compound of the formulae (I) or (I''), (Ia), (Ib), (IA), (IB) or (IC) and/or a pharmaceutically acceptable salt thereof, wherein
$R^2$ is 3-hydroxyprop-1-yn-1-yl.

In one embodiment, the invention provides a compound of the formulae (I) or (I'), (I''), (Ia), (Ib), (IA), (IB) or (IC) and/or a pharmaceutically acceptable salt thereof, wherein
$R^1$ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro.

In another embodiment, the invention provides a compound of the formulae (I) or (I'), (I''), (Ia), (Ib), (IA), (IB) or (IC) and/or a pharmaceutically acceptable salt thereof, wherein
$R^1$ is phenyl, which is unsubstituted or substituted by 1 or 2 substituents independently selected from
methyl, ethyl, difluoromethyl, methoxy, difluoromethoxy, cyclopropyl, chloro or fluoro.

In another embodiment, the invention provides a compound of the formulae (I) or (I'), (I''), (Ia), (Ib), (IA), (IB) or (IC) and/or a pharmaceutically acceptable salt thereof, wherein
$R^1$ is phenyl or o-tolyl.

In one embodiment, the invention provides a compound of the formulae (I) or (I'), (I''), (Ia) or (Ib) and/or a pharmaceutically acceptable salt thereof, wherein
$R^3$ is selected from

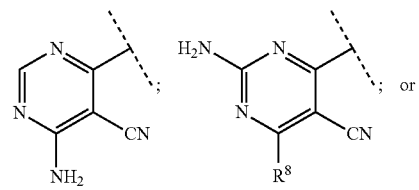

-continued

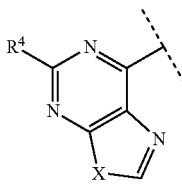

wherein
R⁴ is amino,
R⁸ is methyl, and
X is selected from NH.

In another embodiment, the invention provides a compound of the formulae (I) or (I'), (I"), (Ia) or (Ib) and/or a pharmaceutically acceptable salt thereof, wherein
R³ is selected from

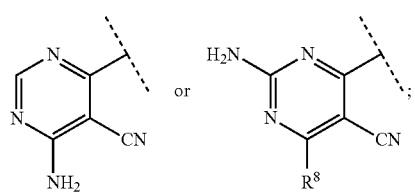

wherein
R⁸ is selected from methyl.

In one embodiment, the invention provides a compound of the formulae (I) or (I'), (Ia), (Ib), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
R² is $C_5$-$C_6$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;
R⁵ is selected from hydrogen or fluoro; and
R⁶ is selected from hydrogen.

In another embodiment, the invention provides a compound of the formulae (I) or (I'), (Ia), (Ib), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
R² is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;
R⁵ is selected from hydrogen or fluoro; and
R⁶ is selected from hydrogen.

In another embodiment, the invention provides a compound of the formulae (I) or (I'), (Ia), (Ib), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
R² is selected from pyrazole, imidazole, pyridine, pyrimidine, isoxazole, thiazole, oxazole or isothiazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;
R⁵ is selected from hydrogen or fluoro; and
R⁶ is selected from hydrogen.

In another embodiment, the invention provides a compound of the formulae (I) or (I'), (Ia), (Ib), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;

$R^2$ is selected from pyrazole, imidazole, pyridine, pyrimidine, isoxazole or thiazole, which is unsubstituted or substituted by 1 substituent independently selected from
$C_1$-$C_4$-alkyl,
hydroxy-$C_1$-$C_4$-alkyl, or
$C_1$-$C_4$-alkoxy;
$R^5$ is selected from hydrogen or fluoro; and
$R^6$ is selected from hydrogen.

In one embodiment, the invention provides a compound of the formulae (I) or (I"), (Ia), (Ib), (IA), (IB) or (IC) and/or a pharmaceutically acceptable salt thereof, wherein
$R^1$ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
$R^2$ is $C_2$-$C_5$-alk-1-ynyl, which is unsubstituted or substituted by 1-2 substituents independently selected from
$C_1$-$C_4$-fluoroalkyl,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
$C_1$-$C_4$-alkoxy,
$C_1$-$C_4$-fluoroalkoxy,
hydroxy, or
fluoro;
$R^5$ is selected from hydrogen or fluoro; and
$R^6$ is selected from hydrogen.

In another embodiment, the invention provides a compound of the formulae (I) or (I"), (Ia), (Ib), (IA), (IB) or (IC) and/or a pharmaceutically acceptable salt thereof, wherein
$R^1$ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
$R^2$ is $C_2$-$C_5$-alk-1-ynyl, which is substituted by 1 substituent selected from hydroxy;
$R^5$ is selected from hydrogen or fluoro; and
$R^6$ is selected from hydrogen.

In another embodiment, the invention provides a compound of the formulae (I) or (I"), (Ia), (Ib), (IA), (IB) or (IC) and/or a pharmaceutically acceptable salt thereof, wherein
$R^1$ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
$R^2$ is 3-hydroxyprop-1-yn-1-yl;
$R^5$ is selected from hydrogen or fluoro; and
$R^6$ is selected from hydrogen.

In one embodiment, the invention provides a compound of the formulae (I) or (I'), (Ia), (Ib), (IA), (IB) or (IC) and/or a pharmaceutically acceptable salt thereof, wherein
$R^1$ is phenyl, which is unsubstituted or substituted by 1 or 2 substituents independently selected from
methyl, ethyl, difluoromethyl, methoxy, difluoromethoxy, cyclopropyl, chloro or fluoro;
$R^2$ is $C_5$-$C_6$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;
$R^5$ is selected from hydrogen or fluoro; and
$R^6$ is selected from hydrogen.

In another embodiment, the invention provides a compound of the formulae (I) or (I'), (Ia), (Ib), (IA), (IB) or (IC) and/or a pharmaceutically acceptable salt thereof, wherein
$R^1$ is phenyl, which is unsubstituted or substituted by 1 or 2 substituents independently selected from
methyl, ethyl, difluoromethyl, methoxy, difluoromethoxy, cyclopropyl, chloro or fluoro;
$R^2$ is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;
$R^5$ is selected from hydrogen or fluoro; and
$R^6$ is selected from hydrogen.

In another embodiment, the invention provides a compound of the formulae (I) or (I'), (Ia), (Ib), (IA), (IB) or (IC) and/or a pharmaceutically acceptable salt thereof, wherein
$R^1$ is phenyl, which is unsubstituted or substituted by 1 or 2 substituents independently selected from
methyl, ethyl, difluoromethyl, methoxy, difluoromethoxy, cyclopropyl, chloro or fluoro;
$R^2$ is selected from pyrazole, imidazole, pyridine, pyrimidine, isoxazole, thiazole, oxazole or isothiazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy, $C_3$-$C_6$-cycloalkyl, which is unsubstituted or substituted by 1-3 substituents independently selected from methyl, or fluoro, $C_3$-$C_6$-heterocycloalkyl, which is unsubstituted or substituted by 1-3 substituents independently selected from methyl, or fluoro, or fluoro;

$R^5$ is selected from hydrogen or fluoro; and $R^6$ is selected from hydrogen.

In another embodiment, the invention provides a compound of the formulae (I) or (I'), (Ia), (Ib), (IA), (IB) or (IC) and/or a pharmaceutically acceptable salt thereof, wherein $R^1$ is phenyl, which is unsubstituted or substituted by 1 or 2 substituents independently selected from methyl, ethyl, difluoromethyl, methoxy, difluoromethoxy, cyclopropyl, chloro or fluoro;

$R^2$ is selected from pyrazole, imidazole, pyridine, pyrimidine, isoxazole or thiazole, which is unsubstituted or substituted by 1 substituent independently selected from $C_1$-$C_4$-alkyl, hydroxy-$C_1$-$C_4$-alkyl, or $C_1$-$C_4$-alkoxy;

$R^5$ is selected from hydrogen or fluoro; and $R^6$ is selected from hydrogen.

In one embodiment, the invention provides a compound of the formulae (I) or (I"), (Ia), (Ib), (IA), (IB) or (IC) and/or a pharmaceutically acceptable salt thereof, wherein $R^1$ is phenyl, which is unsubstituted or substituted by 1 or 2 substituents independently selected from methyl, ethyl, difluoromethyl, methoxy, difluoromethoxy, cyclopropyl, chloro or fluoro;

$R^2$ is $C_2$-$C_5$-alk-1-ynyl, which is unsubstituted or substituted by 1-2 substituents independently selected from $C_1$-$C_4$-fluoroalkyl, $C_3$-$C_6$-cycloalkyl, which is unsubstituted or substituted by 1-3 substituents independently selected from methyl, or fluoro, $C_3$-$C_6$-heterocycloalkyl, which is unsubstituted or substituted by 1-3 substituents independently selected from methyl, or fluoro, $C_1$-$C_4$-alkoxy, $C_1$-$C_4$-fluoroalkoxy, hydroxy, or fluoro;

$R^5$ is selected from hydrogen or fluoro; and $R^6$ is selected from hydrogen.

In another embodiment, the invention provides a compound of the formulae (I) or (I"), (Ia), (Ib), (IA), (IB) or (IC) and/or a pharmaceutically acceptable salt thereof, wherein $R^1$ is phenyl, which is unsubstituted or substituted by 1 or 2 substituents independently selected from methyl, ethyl, difluoromethyl, methoxy, difluoromethoxy, cyclopropyl, chloro or fluoro;

$R^2$ is $C_2$-$C_5$-alk-1-ynyl, which is substituted by 1 substituent selected from hydroxy;

$R^5$ is selected from hydrogen or fluoro; and $R^6$ is selected from hydrogen.

In another embodiment, the invention provides a compound of the formulae (I) or (I"), (Ia), (Ib), (IA), (IB) or (IC) and/or a pharmaceutically acceptable salt thereof, wherein $R^1$ is phenyl, which is unsubstituted or substituted by 1 or 2 substituents independently selected from methyl, ethyl, difluoromethyl, methoxy, difluoromethoxy, cyclopropyl, chloro or fluoro;

$R^2$ is 3-hydroxyprop-1-yn-1-yl;

$R^5$ is selected from hydrogen or fluoro; and $R^6$ is selected from hydrogen.

In one embodiment, the invention provides a compound of the formulae (I) or (I'), (Ia), (Ib), (IA), (IB) or (IC) and/or a pharmaceutically acceptable salt thereof, wherein $R^1$ is phenyl or o-tolyl;

$R^2$ is $C_5$-$C_6$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from $C_1$-$C_4$-alkyl, $C_1$-$C_4$-fluoroalkyl, hydroxy-$C_1$-$C_4$-alkyl, hydroxy-$C_1$-$C_4$-fluoroalkyl, $C_1$-$C_4$-alkoxy, $C_1$-$C_4$-fluoroalkoxy, $C_3$-$C_6$-cycloalkyl, which is unsubstituted or substituted by 1-3 substituents independently selected from methyl, or fluoro, $C_3$-$C_6$-heterocycloalkyl, which is unsubstituted or substituted by 1-3 substituents independently selected from methyl, or fluoro, or fluoro;

$R^5$ is selected from hydrogen or fluoro; and $R^6$ is selected from hydrogen.

In another embodiment, the invention provides a compound of the formulae (I) or (I'), (Ia), (Ib), (IA), (IB) or (IC) and/or a pharmaceutically acceptable salt thereof, wherein $R^1$ is phenyl or o-tolyl;

$R^2$ is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from $C_1$-$C_4$-alkyl, $C_1$-$C_4$-fluoroalkyl, hydroxy-$C_1$-$C_4$-alkyl, hydroxy-$C_1$-$C_4$-fluoroalkyl, $C_1$-$C_4$-alkoxy, $C_1$-$C_4$-fluoroalkoxy, $C_3$-$C_6$-cycloalkyl, which is unsubstituted or substituted by 1-3 substituents independently selected from methyl, or fluoro, $C_3$-$C_6$-heterocycloalkyl, which is unsubstituted or substituted by 1-3 substituents independently selected from methyl, or fluoro, or fluoro;

$R^5$ is selected from hydrogen or fluoro; and $R^6$ is selected from hydrogen.

In another embodiment, the invention provides a compound of the formulae (I) or (I'), (Ia), (Ib), (IA), (IB) or (IC) and/or a pharmaceutically acceptable salt thereof, wherein $R^1$ is phenyl or o-tolyl;

$R^2$ is selected from pyrazole, imidazole, pyridine, pyrimidine, isoxazole, thiazole, oxazole or isothiazole, which is unsubstituted or substituted by 1-2 substituents independently selected from $C_1$-$C_4$-alkyl, $C_1$-$C_4$-fluoroalkyl, hydroxy-$C_1$-$C_4$-alkyl, hydroxy-$C_1$-$C_4$-fluoroalkyl, $C_1$-$C_4$-alkoxy, $C_1$-$C_4$-fluoroalkoxy, $C_3$-$C_6$-cycloalkyl, which is unsubstituted or substituted by 1-3 substituents independently selected from methyl, or fluoro, C₃-C₆-heterocycloalkyl, which is unsubstituted or substituted by 1-3 substituents independently selected from methyl, or fluoro, or
fluoro;
R⁵ is selected from hydrogen or fluoro; and
R⁶ is selected from hydrogen.

In another embodiment, the invention provides a compound of the formulae (I) or (I'), (Ia), (Ib), (IA), (IB) or (IC) and/or a pharmaceutically acceptable salt thereof, wherein
R¹ is phenyl or o-tolyl;
R² is selected from pyrazole, imidazole, pyridine, pyrimidine, isoxazole or thiazole, which is unsubstituted or substituted by 1 substituent independently selected from
C₁-C₄-alkyl,
hydroxy-C₁-C₄-alkyl, or
C₁-C₄-alkoxy;
R⁵ is selected from hydrogen or fluoro; and
R⁶ is selected from hydrogen.

In one embodiment, the invention provides a compound of the formulae (I) or (I''), (Ia), (Ib), (IA), (IB) or (IC) and/or a pharmaceutically acceptable salt thereof, wherein
R¹ is phenyl or o-tolyl;
R² is C₂-C₅-alk-1-ynyl, which is unsubstituted or substituted by 1-2 substituents independently selected from
C₁-C₄-fluoroalkyl,
C₃-C₆-cycloalkyl, which is unsubstituted or substituted by 1-3 substituents independently selected from methyl, or fluoro,
C₃-C₆-heterocycloalkyl, which is unsubstituted or substituted by 1-3 substituents independently selected from methyl, or fluoro,
C₁-C₄-alkoxy,
C₁-C₄-fluoroalkoxy,
hydroxy, or
fluoro;
R⁵ is selected from hydrogen or fluoro; and
R⁶ is selected from hydrogen.

In another embodiment, the invention provides a compound of the formulae (I) or (I''), (Ia), (Ib), (IA), (IB) or (IC) and/or a pharmaceutically acceptable salt thereof, wherein
R¹ is phenyl or o-tolyl;
R² is C₂-C₅-alk-1-ynyl, which is substituted by 1 substituent selected from hydroxy;
R⁵ is selected from hydrogen or fluoro; and
R⁶ is selected from hydrogen.

In another embodiment, the invention provides a compound of the formulae (I) or (I''), (Ia), (Ib), (IA), (IB) or (IC) and/or a pharmaceutically acceptable salt thereof, wherein
R¹ is phenyl or o-tolyl;
R² is 3-hydroxyprop-1-yn-1-yl;
R⁵ is selected from hydrogen or fluoro; and
R⁶ is selected from hydrogen.

In one embodiment, the invention provides a compound of the formulae (I) or (I'), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
R² is C₅-C₆-heteroaryl, containing one nitrogen atom and additional 0, 1, 2 or 3 heteroatoms independently selected from N, O or S, wherein C₄-C₇-heteroaryl is unsubstituted or substituted by 1-3 substituents independently selected from
C₁-C₄-alkyl,
C₁-C₄-fluoroalkyl,
hydroxy-C₁-C₄-alkyl,
hydroxy-C₁-C₄-fluoroalkyl,
C₁-C₄-alkoxy,
C₁-C₄-fluoroalkoxy,
C₃-C₆-cycloalkyl, which is unsubstituted or substituted by 1-3 substituents independently selected from methyl, or fluoro,
C₃-C₆-heterocycloalkyl, which is unsubstituted or substituted by 1-3 substituents independently selected from methyl, or fluoro, or
fluoro;
-L-R³ is selected from

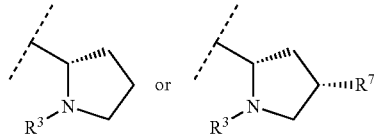

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I'), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
R² is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from
C₁-C₄-alkyl,
C₁-C₄-fluoroalkyl,
hydroxy-C₁-C₄-alkyl,
hydroxy-C₁-C₄-fluoroalkyl,
C₁-C₄-alkoxy,
C₁-C₄-fluoroalkoxy,
C₃-C₆-cycloalkyl, which is unsubstituted or substituted by 1-3 substituents independently selected from methyl, or fluoro,
C₃-C₆-heterocycloalkyl, which is unsubstituted or substituted by 1-3 substituents independently selected from methyl, or fluoro, or
fluoro;
-L-R³ is selected from

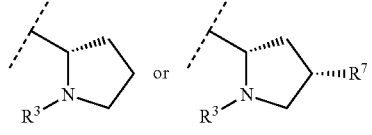

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I'), (IA), (IB) or (IC) and/or a pharmaceutically acceptable salt thereof, wherein
R¹ is phenyl, which is unsubstituted or substituted by 1, 2 or 3 substituents independently selected from
   methyl, ethyl, difluoromethyl, methoxy, difluoromethoxy, cyclopropyl, chloro or fluoro; or
pyridyl, which is unsubstituted or substituted by 1, 2 or 3 substituents independently selected from
   methyl, ethyl, difluoromethyl, methoxy, difluoromethoxy, cyclopropyl, chloro or fluoro;
R² is selected from pyrazole, imidazole, pyridine, pyrimidine, isoxazole, thiazole, oxazole or isothiazole, which is unsubstituted or substituted by 1-2 substituents independently selected from
   $C_1$-$C_4$-alkyl,
   $C_1$-$C_4$-fluoroalkyl,
   hydroxy-$C_1$-$C_4$-alkyl,
   hydroxy-$C_1$-$C_4$-fluoroalkyl,
   $C_1$-$C_4$-alkoxy,
   $C_1$-$C_4$-fluoroalkoxy,
   $C_3$-$C_6$-cycloalkyl, which is unsubstituted or substituted by 1-3 substituents independently selected from methyl, or fluoro,
   $C_3$-$C_6$-heterocycloalkyl, which is unsubstituted or substituted by 1-3 substituents independently selected from methyl, or fluoro, or
   fluoro;
-L-R³ is selected from

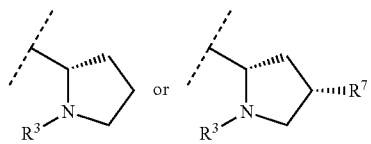

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I'), (IA), (IB) or (IC) and/or a pharmaceutically acceptable salt thereof, wherein
R¹ is phenyl, which is unsubstituted or substituted by 1, 2 or 3 substituents independently selected from
   methyl, ethyl, difluoromethyl, methoxy, difluoromethoxy, cyclopropyl, chloro or fluoro; or
pyridyl, which is unsubstituted or substituted by 1, 2 or 3 substituents independently selected from
   methyl, ethyl, difluoromethyl, methoxy, difluoromethoxy, cyclopropyl, chloro or fluoro;
R² is selected from pyrazole, imidazole, pyridine, pyrimidine, isoxazole or thiazole, which is unsubstituted or substituted by 1 substituent independently selected from
   $C_1$-$C_4$-alkyl,
   hydroxy-$C_1$-$C_4$-alkyl, or
   $C_1$-$C_4$-alkoxy;

-L-R³ is selected from

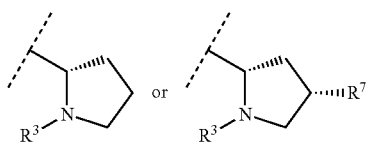

wherein
R⁷ is selected from methoxy, hydroxyl or fluoro;
R⁵ is selected from hydrogen or fluoro; and
R⁶ is selected from hydrogen.

In one embodiment, the invention provides a compound of the formulae (I) or (I"), (IA), (IB) or (IC) and/or a pharmaceutically acceptable salt thereof, wherein
R¹ is phenyl, which is unsubstituted or substituted by 1, 2 or 3 substituents independently selected from
   methyl, ethyl, difluoromethyl, methoxy, difluoromethoxy, cyclopropyl, chloro or fluoro; or
pyridyl, which is unsubstituted or substituted by 1, 2 or 3 substituents independently selected from
   methyl, ethyl, difluoromethyl, methoxy, difluoromethoxy, cyclopropyl, chloro or fluoro;
R² is $C_2$-$C_5$-alk-1-ynyl, which is unsubstituted or substituted by 1-2 substituents independently selected from
   $C_1$-$C_4$-fluoroalkyl,
   $C_3$-$C_6$-cycloalkyl, which is unsubstituted or substituted by 1-3 substituents independently selected from methyl, or fluoro,
   $C_3$-$C_6$-heterocycloalkyl, which is unsubstituted or substituted by 1-3 substituents independently selected from methyl, or fluoro,
   $C_1$-$C_4$-alkoxy,
   $C_1$-$C_4$-fluoroalkoxy,
   hydroxy, or
   fluoro;
-L-R³ is selected from

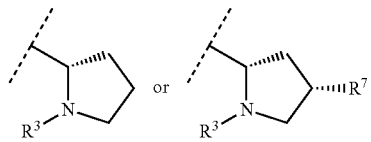

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I"), (IA), (IB) or (IC) and/or a pharmaceutically acceptable salt thereof, wherein
R¹ is phenyl, which is unsubstituted or substituted by 1, 2 or 3 substituents independently selected from
   methyl, ethyl, difluoromethyl, methoxy, difluoromethoxy, cyclopropyl, chloro or fluoro; or
pyridyl, which is unsubstituted or substituted by 1, 2 or 3 substituents independently selected from
   methyl, ethyl, difluoromethyl, methoxy, difluoromethoxy, cyclopropyl, chloro or fluoro;
R² is $C_2$-$C_5$-alk-1-ynyl, which is substituted by 1 substituent selected from hydroxy;

-L-R³ is selected from

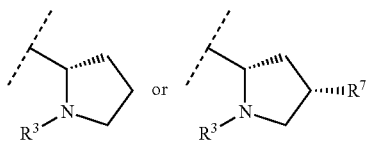

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I"), (IA), (IB) or (IC) and/or a pharmaceutically acceptable salt thereof, wherein
R¹ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro;
R² is 3-hydroxyprop-1-yn-1-yl;
-L-R³ is selected from

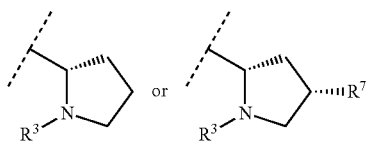

wherein
R⁷ is selected from methoxy, hydroxyl or fluoro;
R⁵ is selected from hydrogen or fluoro; and
R⁶ is selected from hydrogen.

In one embodiment, the invention provides a compound of the formulae (I) or (I'), (Ia), (IA), (IB) or (IC) and/or a pharmaceutically acceptable salt thereof, wherein
R¹ is phenyl, which is unsubstituted or substituted by 1 or 2 substituents independently selected from
methyl, ethyl, difluoromethyl, methoxy, difluoromethoxy, cyclopropyl, chloro or fluoro;
R² is $C_5$-$C_6$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;

-L-R³ is selected from

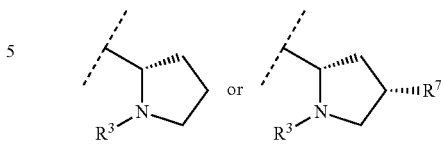

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I'), (IA), (IB) or (IC) and/or a pharmaceutically acceptable salt thereof, wherein
R¹ is phenyl, which is unsubstituted or substituted by 1 or 2 substituents independently selected from
methyl, ethyl, difluoromethyl, methoxy, difluoromethoxy, cyclopropyl, chloro or fluoro;
R² is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro, or
fluoro;
-L-R³ is selected from

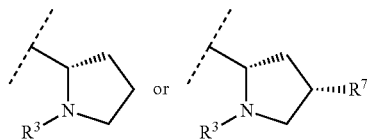

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I'), (IA), (IB) or (IC) and/or a pharmaceutically acceptable salt thereof, wherein
R¹ is phenyl, which is unsubstituted or substituted by 1 or 2 substituents independently selected from
methyl, ethyl, difluoromethyl, methoxy, difluoromethoxy, cyclopropyl, chloro or fluoro;
R² is selected from pyrazole, imidazole, pyridine, pyrimidine, isoxazole, thiazole, oxazole or isothiazole, which is unsubstituted or substituted by 1-2 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy, C$_1$-C$_4$-fluoroalkoxy,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro, or
fluoro;
-L-R$^3$ is selected from

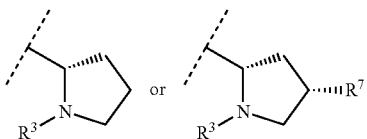

wherein
R$^7$ is selected from methoxy, hydroxyl or fluoro;
R$^5$ is selected from hydrogen or fluoro; and
R$^6$ is selected from hydrogen.

In another embodiment, the invention provides a compound of the formulae (I) or (I'), (IA), (IB) or (IC) and/or a pharmaceutically acceptable salt thereof, wherein
R$^1$ is phenyl, which is unsubstituted or substituted by 1 or 2 substituents independently selected from
methyl, ethyl, difluoromethyl, methoxy, difluoromethoxy, cyclopropyl, chloro or fluoro;
R$^2$ is selected from pyrazole, imidazole, pyridine, pyrimidine, isoxazole or thiazole, which is unsubstituted or substituted by 1 substituent independently selected from
C$_1$-C$_4$-alkyl,
hydroxy-C$_1$-C$_4$-alkyl, or
C$_1$-C$_4$-alkoxy;
-L-R$^3$ is selected from

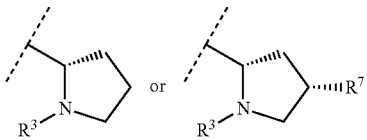

wherein
R$^7$ is selected from methoxy, hydroxyl or fluoro;
R$^5$ is selected from hydrogen or fluoro; and
R$^6$ is selected from hydrogen.

In one embodiment, the invention provides a compound of the formulae (I) or (I''), (IA), (IB) or (IC) and/or a pharmaceutically acceptable salt thereof, wherein
R$^1$ is phenyl, which is unsubstituted or substituted by 1 or 2 substituents independently selected from
methyl, ethyl, difluoromethyl, methoxy, difluoromethoxy, cyclopropyl, chloro or fluoro;
R$^2$ is C$_2$-C$_5$-alk-1-ynyl, which is unsubstituted or substituted by 1-2 substituents independently selected from
C$_1$-C$_4$-fluoroalkyl,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro,
C$_1$-C$_4$-alkoxy,
C$_1$-C$_4$-fluoroalkoxy,
hydroxy, or
fluoro;
-L-R$^3$ is selected from

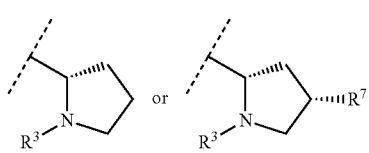

wherein
R$^7$ is selected from methoxy, hydroxyl or fluoro;
R$^5$ is selected from hydrogen or fluoro; and
R$^6$ is selected from hydrogen.

In another embodiment, the invention provides a compound of the formulae (I) or (I''), (IA), (IB) or (IC) and/or a pharmaceutically acceptable salt thereof, wherein
R$^1$ is phenyl, which is unsubstituted or substituted by 1 or 2 substituents independently selected from
methyl, ethyl, difluoromethyl, methoxy, difluoromethoxy, cyclopropyl, chloro or fluoro;
R$^2$ is C$_2$-C$_5$-alk-1-ynyl, which is substituted by 1 substituent selected from hydroxy;
-L-R$^3$ is selected from

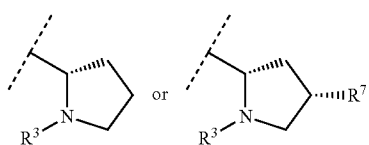

wherein
R$^7$ is selected from methoxy, hydroxyl or fluoro;
R$^5$ is selected from hydrogen or fluoro; and
R$^6$ is selected from hydrogen.

In another embodiment, the invention provides a compound of the formulae (I) or (I''), (IA), (IB) or (IC) and/or a pharmaceutically acceptable salt thereof, wherein
R$^1$ is phenyl, which is unsubstituted or substituted by 1 or 2 substituents independently selected from
methyl, ethyl, difluoromethyl, methoxy, difluoromethoxy, cyclopropyl, chloro or fluoro;
R$^2$ is 3-hydroxyprop-1-yn-1-yl;
-L-R$^3$ is selected from

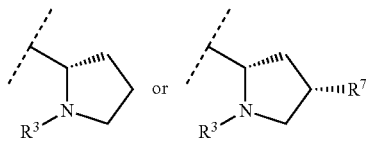

wherein
R$^7$ is selected from methoxy, hydroxyl or fluoro;
R$^5$ is selected from hydrogen or fluoro; and
R$^6$ is selected from hydrogen.

In one embodiment, the invention provides a compound of the formulae (I) or (I'), (IA), (IB) or (IC) and/or a pharmaceutically acceptable salt thereof, wherein
R$^1$ is phenyl or o-tolyl;
R$^2$ is C$_5$-C$_6$-heteroaryl, containing one nitrogen atom and additional 0, 1, 2 or 3 heteroatoms independently selected from N, O or S, wherein C$_4$-C$_7$-heteroaryl is unsubstituted or substituted by 1-3 substituents independently selected from C$_1$-C$_4$-alkyl,
C$_1$-C$_4$-fluoroalkyl,
hydroxy-C$_1$-C$_4$-alkyl,
hydroxy-C$_1$-C$_4$-fluoroalkyl,
C$_1$-C$_4$-alkoxy,
C$_1$-C$_4$-fluoroalkoxy,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro, or
fluoro;
-L-R$^3$ is selected from

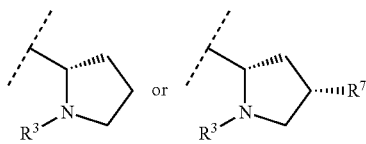

wherein
R$^7$ is selected from methoxy, hydroxyl or fluoro;
R$^5$ is selected from hydrogen or fluoro; and
R$^6$ is selected from hydrogen.

In another embodiment, the invention provides a compound of the formulae (I) or (I'), (IA), (IB) or (IC) and/or a pharmaceutically acceptable salt thereof, wherein
R$^1$ is phenyl or o-tolyl;
R$^2$ is selected from pyrazole, imidazole, pyridine, pyrimidine, isoxazole, thiazole, pyridazine, pyrazine, oxazole, isothiazole, thiophene, furan, triazole or tetrazole, which is unsubstituted or substituted by 1-2 substituents independently selected from
C$_1$-C$_4$-alkyl,
C$_1$-C$_4$-fluoroalkyl,
hydroxy-C$_1$-C$_4$-alkyl,
hydroxy-C$_1$-C$_4$-fluoroalkyl,
C$_1$-C$_4$-alkoxy,
C$_1$-C$_4$-fluoroalkoxy,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro, or
fluoro;
-L-R$^3$ is selected from

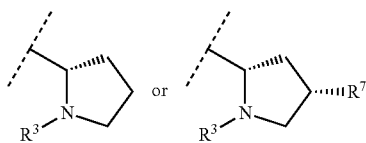

wherein
R$^7$ is selected from methoxy, hydroxyl or fluoro;
R$^5$ is selected from hydrogen or fluoro; and
R$^6$ is selected from hydrogen.

In another embodiment, the invention provides a compound of the formulae (I) or (I'), (IA), (IB) or (IC) and/or a pharmaceutically acceptable salt thereof, wherein
R$^1$ is phenyl or o-tolyl;

R$^2$ is selected from pyrazole, imidazole, pyridine, pyrimidine, isoxazole, thiazole, oxazole or isothiazole, which is unsubstituted or substituted by 1-2 substituents independently selected from
C$_1$-C$_4$-alkyl,
C$_1$-C$_4$-fluoroalkyl,
hydroxy-C$_1$-C$_4$-alkyl,
hydroxy-C$_1$-C$_4$-fluoroalkyl,
C$_1$-C$_4$-alkoxy,
C$_1$-C$_4$-fluoroalkoxy,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro, or
fluoro;
-L-R$^3$ is selected from

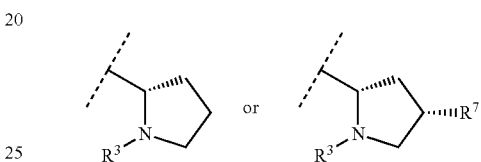

wherein
R$^7$ is selected from methoxy, hydroxyl or fluoro;
R$^5$ is selected from hydrogen or fluoro; and
R$^6$ is selected from hydrogen.

In another embodiment, the invention provides a compound of the formulae (I) or (I'), (IA), (IB) or (IC) and/or a pharmaceutically acceptable salt thereof, wherein
R$^1$ is phenyl or o-tolyl;
R$^2$ is selected from pyrazole, imidazole, pyridine, pyrimidine, isoxazole or thiazole, which is unsubstituted or substituted by 1 substituent independently selected from
C$_1$-C$_4$-alkyl,
hydroxy-C$_1$-C$_4$-alkyl, or
C$_1$-C$_4$-alkoxy;
-L-R$^3$ is selected from

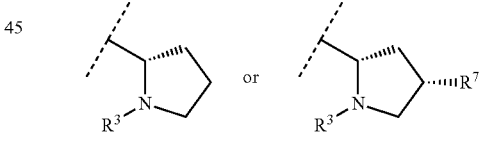

wherein
R$^7$ is selected from methoxy, hydroxyl or fluoro;
R$^5$ is selected from hydrogen or fluoro; and
R$^6$ is selected from hydrogen.

In one embodiment, the invention provides a compound of the formulae (I) or (I"), (IA), (IB) or (IC) and/or a pharmaceutically acceptable salt thereof, wherein
R$^1$ is phenyl or o-tolyl;
R$^2$ is C$_2$-C$_5$-alk-1-ynyl, which is unsubstituted or substituted by 1-2 substituents independently selected from
C$_1$-C$_4$-fluoroalkyl,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro, C₁-C₄-alkoxy,
C₁-C₄-fluoroalkoxy,
hydroxy, or
fluoro;
-L-R³ is selected from

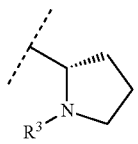 or 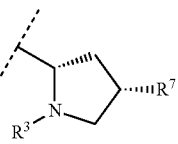

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I"), (IA), (IB) or (IC) and/or a pharmaceutically acceptable salt thereof, wherein
R¹ is phenyl or o-tolyl;
R² is C₂-C₅-alk-1-ynyl, which is substituted by 1 substituent selected from hydroxy;
-L-R³ is selected from

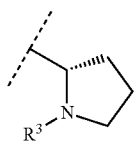 or 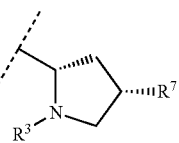

wherein
R⁷ is selected from methoxy, hydroxyl or fluoro;
R⁵ is selected from hydrogen or fluoro; and
R⁶ is selected from hydrogen.

In another embodiment, the invention provides a compound of the formulae (I) or (I"), (IA), (IB) or (IC) and/or a pharmaceutically acceptable salt thereof, wherein
R¹ is phenyl or o-tolyl;
R² is 3-hydroxyprop-1-yn-1-yl;
-L-R³ is selected from

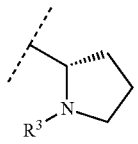 or 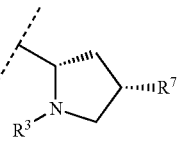

wherein
R⁷ is selected from methoxy, hydroxyl or fluoro;
R⁵ is selected from hydrogen or fluoro; and
R⁶ is selected from hydrogen.

In one embodiment, the invention provides a compound of the formula (I), selected from
2-Amino-4-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)-6-methylpyrimidine-5-carbonitrile,
(S)-4-Amino-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile,
(S)-4-Amino-6-(2-(5-(2-methoxypyrimidin-5-yl)-4-oxo-3-phenyl-3,4-dihydroquinazolin-2-yl)pyrrolidin-1-yl)pyrimidine-5-carbonitrile,
(S)-2-Amino-4-(2-(5-(2-methoxypyrimidin-5-yl)-4-oxo-3-phenyl-3,4-dihydroquinazolin-2-yl)pyrrolidin-1-yl)-6-methylpyrimidine-5-carbonitrile,
(S)-4-Amino-6-(2-(6-fluoro-5-(1-methyl-1H-pyrazol-4-yl)-4-oxo-3-phenyl-3,4-dihydroquinazolin-2-yl)pyrrolidin-1-yl)pyrimidine-5-carbonitrile,
(S)-2-Amino-4-(2-(6-fluoro-5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
2-Amino-4-((2S,4S)-2-(6-fluoro-5-(2-methoxypyrimidin-5-yl)-4-oxo-3-phenyl-3,4-dihydroquinazolin-2-yl)-4-hydroxypyrrolidin-1-yl)-6-methylpyrimidine-5-carbonitrile,
4-Amino-6-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)pyrimidine-5-carbonitrile,
2-Amino-4-((2S,4S)-2-(6-fluoro-5-(2-methoxythiazol-5-yl)-4-oxo-3-phenyl-3,4-dihydroquinazolin-2-yl)-4-hydroxypyrrolidin-1-yl)-6-methylpyrimidine-5-carbonitrile,
2-Amino-4-((2S,4S)-4-methoxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
2-((2S,4S)-1-(2-Amino-9H-purin-6-yl)-4-methoxypyrrolidin-2-yl)-5-(1-methyl-1H-pyrazol-4-yl)-3-phenylquinazolin-4(3H)-one,
(S)-2-Amino-4-methyl-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile,
(S)-4-Amino-6-(2-(5-(1-methyl-1H-pyrazol-4-yl)-4-oxo-3-(o-tolyl)-3,4-dihydroquinazolin-2-yl)pyrrolidin-1-yl)pyrimidine-5-carbonitrile,
(S)-4-Amino-6-(2-(5-(1-methyl-1H-imidazol-4-yl)-4-oxo-3-phenyl-3,4-dihydroquinazolin-2-yl)pyrrolidin-1-yl)pyrimidine-5-carbonitrile,
2-Amino-4-((2S,4S)-4-hydroxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
(S)-2-Amino-4-methyl-6-(2-(4-oxo-3-phenyl-5-(pyrimidin-5-yl)-3,4-dihydroquinazolin-2-yl)pyrrolidin-1-yl)pyrimidine-5-carbonitrile,
(S)-2-Amino-4-(2-(5-(5-methoxypyridin-3-yl)-4-oxo-3-phenyl-3,4-dihydroquinazolin-2-yl)pyrrolidin-1-yl)-6-methylpyrimidine-5-carbonitrile,
(S)-2-Amino-4-methyl-6-(2-(5-(2-methylpyrimidin-5-yl)-4-oxo-3-phenyl-3,4-dihydroquinazolin-2-yl)pyrrolidin-1-yl)pyrimidine-5-carbonitrile,
(S)-2-Amino-4-methyl-6-(2-(4-oxo-3-phenyl-5-(pyridin-3-yl)-3,4-dihydroquinazolin-2-yl)pyrrolidin-1-yl)pyrimidine-5-carbonitrile,
(S)-2-Amino-4-(2-(5-(6-methoxypyridin-3-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(5-(2-methylpyrimidin-5-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(4-oxo-3-phenyl-5-(pyridin-3-yl)-3,4-dihydroquinazolin-2-yl)pyrrolidin-1-yl)-6-methylpyrimidine-5-carbonitrile,
2-Amino-4-((2S,4S)-4-hydroxy-2-(5-(5-methoxypyridin-3-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(4-oxo-3-phenyl-5-(pyrimidin-5-yl)-3,4-dihydroquinazolin-2-yl)pyrrolidin-1-yl)-6-methylpyrimidine-5-carbonitrile, 2-Amino-4-((2S,4S)-4-hydroxy-2-(5-(4-methoxypyridin-3-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(5-(1-(2-hydroxyethyl)-1H-pyrazol-4-yl)-4-oxo-3-phenyl-3,4-dihydroquinazolin-2-yl)pyrrolidin-1-yl)-6-methylpyrimidine-5-carbonitrile,
2-Amino-4-((2S,4S)-2-(5-(2-ethoxypyrimidin-5-yl)-6-fluoro-4-oxo-3-phenyl-3,4-dihydroquinazolin-2-yl)-4-hydroxypyrrolidin-1-yl)-6-methylpyrimidine-5-carbonitrile,
2-Amino-4-((2S,4S)-4-fluoro-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
2-Amino-4-((2S,4S)-2-(6-fluoro-5-(1-methyl-1H-imidazol-4-yl)-4-oxo-3-phenyl-3,4-dihydroquinazolin-2-yl)-4-hydroxypyrrolidin-1-yl)-6-methylpyrimidine-5-carbonitrile,
(S)-2-Amino-4-(2-(5-(2-ethoxypyrimidin-5-yl)-4-oxo-3-phenyl-3,4-dihydroquinazolin-2-yl)pyrrolidin-1-yl)-6-methylpyrimidine-5-carbonitrile,
(S)-4-Amino-6-(2-(5-(3-hydroxyprop-1-yn-1-yl)-4-oxo-3-phenyl-3,4-dihydroquinazolin-2-yl)pyrrolidin-1-yl)pyrimidine-5-carbonitrile, or
2-Amino-4-((2S,4S)-4-methoxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile,
and/or a pharmaceutically acceptable salt thereof.

In another embodiment individual compounds according to the invention are those listed in the Examples section below.

The following enumerated embodiments are also embodiments of the present invention:

Embodiment 1

A compound of formula (I)

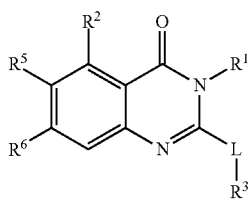

(I)

or a pharmaceutically acceptable salt thereof wherein
$R^1$ is selected from
phenyl, which is unsubstituted or substituted by 1, 2 or 3 substituents independently selected from
   methyl, ethyl, difluoromethyl, methoxy, difluoromethoxy, cyclopropyl, chloro or fluoro;
pyridyl, which is unsubstituted or substituted by 1, 2 or 3 substituents independently selected from
   methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
   $C_1$-$C_4$-alkyl,
   $C_1$-$C_4$-fluoroalkyl,
   hydroxy-$C_1$-$C_4$-alkyl,
   hydroxy-$C_1$-$C_4$-fluoroalkyl,
   $C_1$-$C_4$-alkoxy,
   $C_1$-$C_4$-fluoroalkoxy,
   $C_3$-$C_6$-cycloalkyl, which is unsubstituted or substituted by 1-3 substituents independently selected from methyl, or fluoro,
   $C_3$-$C_6$-heterocycloalkyl, which is unsubstituted or substituted by 1-3 substituents independently selected from methyl, or fluoro,
   cyano,
   fluoro,
   amino,
   $C_1$-$C_4$-alkylamino, or
   $C_1$-$C_4$-dialkylamino;
or
$C_2$-$C_5$-alkynyl, which is unsubstituted or substituted by 1-2 substituents independently selected from
   $C_1$-$C_4$-fluoroalkyl,
   $C_3$-$C_6$-cycloalkyl, which is unsubstituted or substituted by 1-3 substituents independently selected from methyl, or fluoro,
   $C_3$-$C_6$-heterocycloalkyl, which is unsubstituted or substituted by 1-3 substituents independently selected from methyl, or fluoro,
   $C_1$-$C_4$-alkoxy,
   $C_1$-$C_4$-fluoroalkoxy,
   hydroxyl,
   cyano,
   fluoro,
   amino,
   $C_1$-$C_4$-alkylamino, or
   $C_1$-$C_4$-dialkylamino;
$R^5$ and $R^6$ are independently selected from hydrogen, deuterium or fluoro;
-L-$R^3$ is selected from

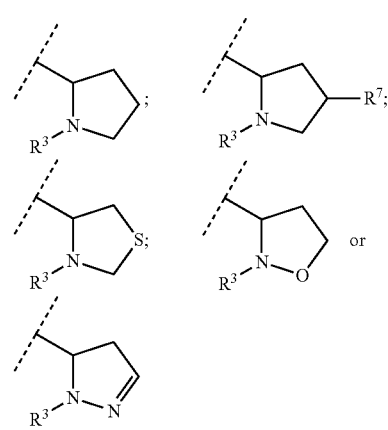

wherein
$R^7$ is selected from methoxy, difluoromethoxy, trifluoromethoxy, hydroxy, fluoro or methylsulfonylamine;
and R³ is selected from

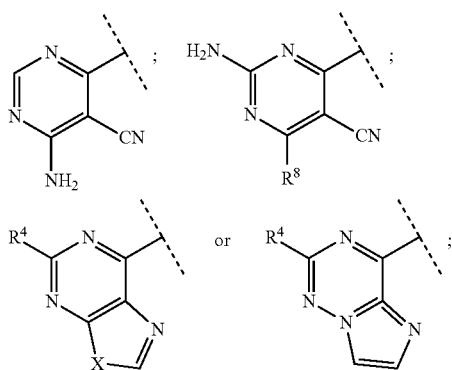

wherein
R⁴ is selected from hydrogen or amino,
R⁸ is selected from hydrogen, methyl, fluoromethyl, difluoromethyl, trideuteromethyl or amino, and
X is selected from NH, NMe or S.

Embodiment 2

A compound according to embodiment 1 or a pharmaceutically acceptable salt thereof, of the formula (I')

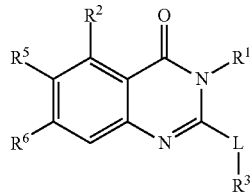

(I')

wherein,
R¹ is selected from
phenyl, which is unsubstituted or substituted by 1, 2 or 3 substituents independently selected from
methyl, ethyl, difluoromethyl, methoxy, difluoromethoxy, cyclopropyl, chloro or fluoro;
pyridyl, which is unsubstituted or substituted by 1, 2 or 3 substituents independently selected from
methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
R² is $C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
cyano,
fluoro,
amino,
$C_1$-$C_4$-alkylamino, or
$C_1$-$C_4$-dialkylamino;
R⁵ and R⁶ are independently selected from hydrogen, deuterium or fluoro;
-L-R³ is selected from

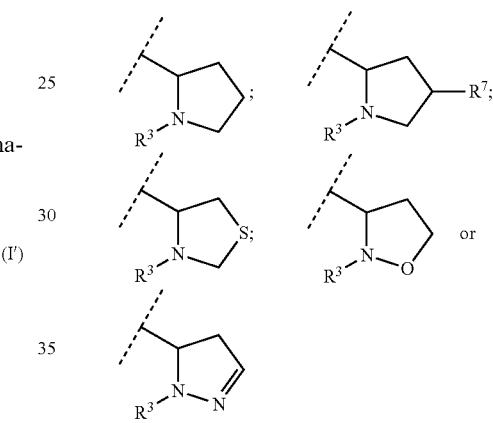

wherein
R⁷ is selected from methoxy, difluoromethoxy, trifluoromethoxy, hydroxy, fluoro or methylsulfonylamine; and
R³ is selected from

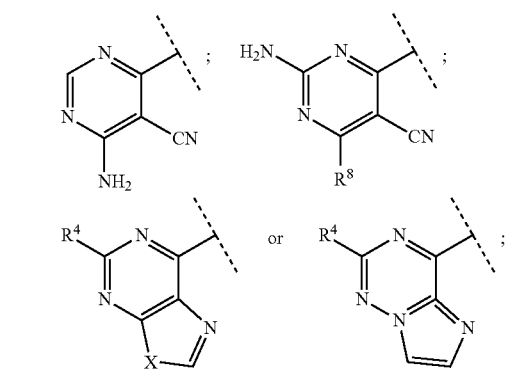

wherein
R⁴ is selected from hydrogen or amino,
R⁸ is selected from hydrogen, methyl, fluoromethyl, difluoromethyl, trideuteromethyl or amino, and
X is selected from NH, NMe or S.

Embodiment 3

A compound according to embodiment 1 or 2 or a pharmaceutically acceptable salt thereof, of the formula (Ia)

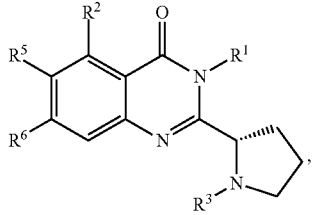

(Ia)

wherein
$R^1$ is selected from
phenyl, which is unsubstituted or substituted by 1, 2 or 3 substituents independently selected from
  methyl, ethyl, difluoromethyl, methoxy, difluoromethoxy, cyclopropyl, chloro or fluoro;
pyridyl, which is unsubstituted or substituted by 1, 2 or 3 substituents independently selected from
  methyl, ethyl, difluoromethyl, methoxy, difluoromethoxy, cyclopropyl, chloro or fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
  $C_1$-$C_4$-alkyl,
  $C_1$-$C_4$-fluoroalkyl,
  hydroxy-$C_1$-$C_4$-alkyl,
  hydroxy-$C_1$-$C_4$-fluoroalkyl,
  $C_1$-$C_4$-alkoxy,
  $C_1$-$C_4$-fluoroalkoxy,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  cyano,
  fluoro,
  amino,
  $C_1$-$C_4$-alkylamino, or
  $C_1$-$C_4$-dialkylamino;
or
$C_2$-$C_5$-alkynyl, which is unsubstituted or substituted by 1-2 substituents independently selected from
  $C_1$-$C_4$-fluoroalkyl,
  $C_3$-$C_6$-cycloalkyl, which is unsubstituted or substituted by 1-3 substituents independently selected from methyl, or fluoro,
  $C_3$-$C_6$-heterocycloalkyl, which is unsubstituted or substituted by 1-3 substituents independently selected from methyl, or fluoro,
  $C_1$-$C_4$-alkoxy,
  $C_1$-$C_4$-fluoroalkoxy,
  hydroxy,
  cyano,
  fluoro,
  amino,
  $C_1$-$C_4$-alkylamino, or
  $C_1$-$C_4$-dialkylamino;
$R^5$ and $R^6$ are independently selected from hydrogen, deuterium or fluoro; and
$R^3$ is selected from

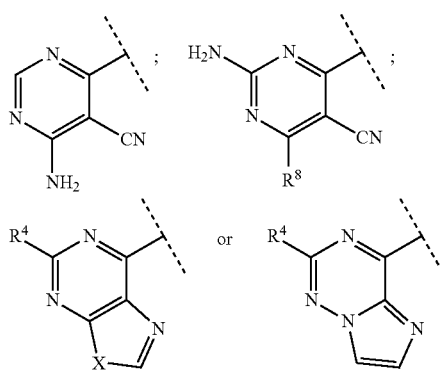

wherein
$R^4$ is selected from hydrogen or amino,
$R^8$ is selected from hydrogen, methyl, fluoromethyl, difluoromethyl, trideuteromethyl or amino, and
X is selected from NH, NMe or S.

Embodiment 4

A compound according to embodiment 1 or 2 or a pharmaceutically acceptable salt thereof, of the formula (Ib)

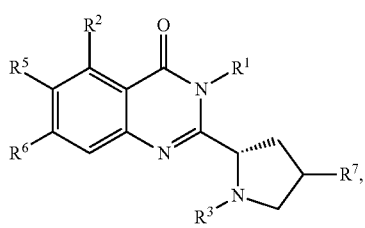

(Ib)

wherein
$R^1$ is selected from
phenyl, which is unsubstituted or substituted by 1, 2 or 3 substituents independently selected from
  methyl, ethyl, difluoromethyl, methoxy, difluoromethoxy, cyclopropyl, chloro or fluoro;
pyridyl, which is unsubstituted or substituted by 1, 2 or 3 substituents independently selected from
  methyl, ethyl, difluoromethyl, methoxy, difluoromethoxy, cyclopropyl, chloro or fluoro;

1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;
pyrolidin-3-yl, which is unsubstituted or substituted in the 1 position by a substituent which is selected from methoxycarbonyl, methylsulfonyl, methyl or methylcarbonyl; or
dimethylamine;
$R^2$ is selected from
$C_4$-$C_7$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
cyano,
fluoro,
amino,
$C_1$-$C_4$-alkylamino, or
$C_1$-$C_4$-dialkylamino;
or
$C_2$-$C_5$-alkynyl, which is unsubstituted or substituted by 1-2 substituents independently selected from
$C_1$-$C_4$-fluoroalkyl,
$C_3$-$C_6$-cycloalkyl, which is unsubstituted or substituted by 1-3 substituents independently selected from methyl, or fluoro,
$C_3$-$C_6$-heterocycloalkyl, which is unsubstituted or substituted by 1-3 substituents independently selected from methyl, or fluoro,
$C_1$-$C_4$-alkoxy,
$C_1$-$C_4$-fluoroalkoxy,
hydroxy,
cyano,
fluoro,
amino,
$C_1$-$C_4$-alkylamino, or
$C_1$-$C_4$-dialkylamino;
$R^5$ and $R^6$ are independently selected from hydrogen, deuterium or fluoro;
$R^7$ is selected from methoxy, difluoromethoxy, trifluoromethoxy, hydroxy, fluoro or methylsulfonylamine; and
$R^3$ is selected from

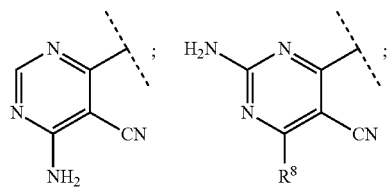

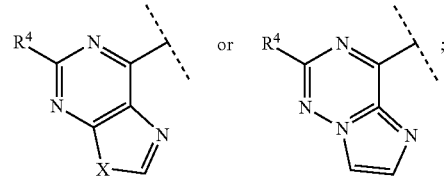

wherein
$R^4$ is selected from hydrogen or amino,
$R^8$ is selected from hydrogen, methyl, fluoromethyl, difluoromethyl, trideuteromethyl or amino, and
X is selected from NH, NMe or S.

Embodiment 5

A compound according to any one of Embodiments 1 to 4 or a pharmaceutically acceptable salt thereof which is a compound of formula (IA), (IB) or (IC),

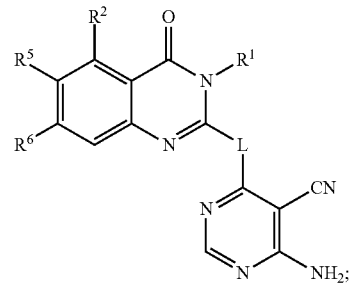

(IA)

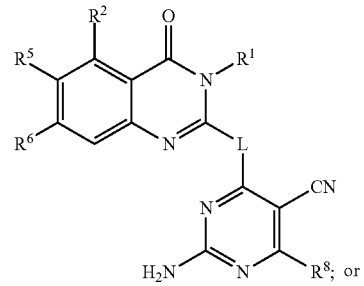

(IB)

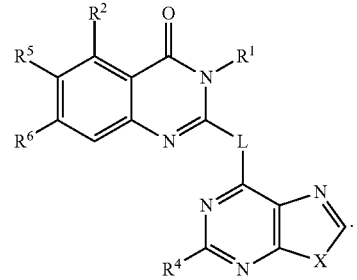

(IC)

Embodiment 6

A compound according to any one of embodiments 1 to 5 or a pharmaceutically acceptable salt thereof wherein
$R^2$ is $C_5$-$C_6$-heteroaryl, containing one nitrogen atom and additional 0, 1, 2 or 3 heteroatoms independently selected from N, O or S, wherein $C_4$-$C_7$-heteroaryl is unsubstituted or substituted by 1-3 substituents independently selected from

49

C$_1$-C$_4$-alkyl,
C$_1$-C$_4$-fluoroalkyl,
hydroxy-C$_1$-C$_4$-alkyl,
hydroxy-C$_1$-C$_4$-fluoroalkyl,
C$_1$-C$_4$-alkoxy,
C$_1$-C$_4$-fluoroalkoxy,
C$_3$-C$_6$-cycloalkyl, which is unsubstituted or substituted by 1-3 substituents independently selected from methyl, or fluoro,
C$_3$-C$_6$-heterocycloalkyl, which is unsubstituted or substituted by 1-3 substituents independently selected from methyl, or fluoro, or
fluoro.

Embodiment 7

A compound according to any one of embodiments 1 to 6 or a pharmaceutically acceptable salt thereof wherein
R$^1$ is phenyl, which is unsubstituted or substituted by 1, 2 or 3 substituents independently selected from
methyl, ethyl, difluoromethyl, methoxy, difluoromethoxy, cyclopropyl, chloro or fluoro; or
pyridyl, which is unsubstituted or substituted by 1, 2 or 3 substituents independently selected from
methyl, ethyl, difluoromethyl, methoxy, difluoromethoxy, cyclopropyl, chloro or fluoro.

Embodiment 8

A compound according to embodiment 1, selected from
2-Amino-4-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)-6-methylpyrimidine-5-carbonitrile,
(S)-4-Amino-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile,
(S)-4-Amino-6-(2-(5-(2-methoxypyrimidin-5-yl)-4-oxo-3-phenyl-3,4-dihydroquinazolin-2-yl)pyrrolidin-1-yl)pyrimidine-5-carbonitrile,
(S)-2-Amino-4-(2-(5-(2-methoxypyrimidin-5-yl)-4-oxo-3-phenyl-3,4-dihydroquinazolin-2-yl)pyrrolidin-1-yl)-6-methylpyrimidine-5-carbonitrile,
(S)-4-Amino-6-(2-(6-fluoro-5-(1-methyl-1H-pyrazol-4-yl)-4-oxo-3-phenyl-3,4-dihydroquinazolin-2-yl)pyrrolidin-1-yl)pyrimidine-5-carbonitrile,
(S)-2-Amino-4-(2-(6-fluoro-5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
2-Amino-4-((2S,4S)-2-(6-fluoro-5-(2-methoxypyrimidin-5-yl)-4-oxo-3-phenyl-3,4-dihydroquinazolin-2-yl)-4-hydroxypyrrolidin-1-yl)-6-methylpyrimidine-5-carbonitrile,
4-Amino-6-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)pyrimidine-5-carbonitrile,
2-Amino-4-((2S,4S)-2-(6-fluoro-5-(2-methoxythiazol-5-yl)-4-oxo-3-phenyl-3,4-dihydroquinazolin-2-yl)-4-hydroxypyrrolidin-1-yl)-6-methylpyrimidine-5-carbonitrile,
2-Amino-4-((2S,4S)-4-methoxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
2-((2S,4S)-1-(2-Amino-9H-purin-6-yl)-4-methoxypyrrolidin-2-yl)-5-(1-methyl-1H-pyrazol-4-yl)-3-phenylquinazolin-4(3H)-one,
(S)-2-Amino-4-methyl-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile,

50

(S)-4-Amino-6-(2-(5-(1-methyl-1H-pyrazol-4-yl)-4-oxo-3-(o-tolyl)-3,4-dihydroquinazolin-2-yl)pyrrolidin-1-yl)pyrimidine-5-carbonitrile,
(S)-4-Amino-6-(2-(5-(1-methyl-1H-imidazol-4-yl)-4-oxo-3-phenyl-3,4-dihydroquinazolin-2-yl)pyrrolidin-1-yl)pyrimidine-5-carbonitrile,
2-Amino-4-((2S,4S)-4-hydroxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
(S)-2-Amino-4-methyl-6-(2-(4-oxo-3-phenyl-5-(pyrimidin-5-yl)-3,4-dihydroquinazolin-2-yl)pyrrolidin-1-yl)pyrimidine-5-carbonitrile,
(S)-2-Amino-4-(2-(5-(5-methoxypyridin-3-yl)-4-oxo-3-phenyl-3,4-dihydroquinazolin-2-yl)pyrrolidin-1-yl)-6-methylpyrimidine-5-carbonitrile,
(S)-2-Amino-4-methyl-6-(2-(5-(2-methylpyrimidin-5-yl)-4-oxo-3-phenyl-3,4-dihydroquinazolin-2-yl)pyrrolidin-1-yl)pyrimidine-5-carbonitrile,
(S)-2-Amino-4-methyl-6-(2-(4-oxo-3-phenyl-5-(pyridin-3-yl)-3,4-dihydroquinazolin-2-yl)pyrrolidin-1-yl)pyrimidine-5-carbonitrile,
(S)-2-Amino-4-(2-(5-(6-methoxypyridin-3-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(5-(2-methylpyrimidin-5-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(4-oxo-3-phenyl-5-(pyridin-3-yl)-3,4-dihydroquinazolin-2-yl)pyrrolidin-1-yl)-6-methylpyrimidine-5-carbonitrile,
2-Amino-4-((2S,4S)-4-hydroxy-2-(5-(5-methoxypyridin-3-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(4-oxo-3-phenyl-5-(pyrimidin-5-yl)-3,4-dihydroquinazolin-2-yl)pyrrolidin-1-yl)-6-methylpyrimidine-5-carbonitrile,
2-Amino-4-((2S,4S)-4-hydroxy-2-(5-(4-methoxypyridin-3-yl)-4-oxo-3-phenyl-3,4-dihydroquinazolin-2-yl)pyrrolidin-1-yl)-6-methylpyrimidine-5-carbonitrile,
2-Amino-4-((2S,4S)-4-hydroxy-2-(5-(1-(2-hydroxyethyl)-1H-pyrazol-4-yl)-4-oxo-3-phenyl-3,4-dihydroquinazolin-2-yl)pyrrolidin-1-yl)-6-methylpyrimidine-5-carbonitrile,
2-Amino-4-((2S,4S)-2-(5-(2-ethoxypyrimidin-5-yl)-6-fluoro-4-oxo-3-phenyl-3,4-dihydroquinazolin-2-yl)-4-hydroxypyrrolidin-1-yl)-6-methylpyrimidine-5-carbonitrile,
2-Amino-4-((2S,4S)-4-fluoro-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile,
2-Amino-4-((2S,4S)-2-(6-fluoro-5-(1-methyl-1H-imidazol-4-yl)-4-oxo-3-phenyl-3,4-dihydroquinazolin-2-yl)-4-hydroxypyrrolidin-1-yl)-6-methylpyrimidine-5-carbonitrile,
(S)-2-Amino-4-(2-(5-(2-ethoxypyrimidin-5-yl)-4-oxo-3-phenyl-3,4-dihydroquinazolin-2-yl)pyrrolidin-1-yl)-6-methylpyrimidine-5-carbonitrile,
(S)-4-Amino-6-(2-(5-(3-hydroxyprop-1-yn-1-yl)-4-oxo-3-phenyl-3,4-dihydroquinazolin-2-yl)pyrrolidin-1-yl)pyrimidine-5-carbonitrile, or 2-Amino-4-((2S,4S)-4-methoxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile, or a pharmaceutically acceptable salt thereof.

Embodiment 9

A pharmaceutical composition comprising a therapeutically effective amount of a compound according to any one of embodiments 1 to 8 or a pharmaceutically acceptable salt thereof and one or more pharmaceutically acceptable carriers.

Embodiment 10

A combination comprising a therapeutically effective amount of a compound according to any one of embodiments 1 to 8 or a pharmaceutically acceptable salt thereof and one or more therapeutically active co-agents.

Embodiment 11

A method of modulating the activity of the class I PI3 kinases, in a subject, wherein the method comprises administering to the subject a therapeutically effective amount of a compound according to any one of embodiments 1 to 8 or a pharmaceutically acceptable salt thereof.

Embodiment 12

A method of treating a disorder or a disease selected from rheumatoid arthritis (RA), pemphigus vulgaris (PV), endemic form of Brazilian pemphigus (Fogo selvagem), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection, cancers of haematopoietic origin, severe and cerebral malaria, trypanosomiasis, leishmaniasis, toxoplasmosis and neurocysticercosis comprising administering to a subject a therapeutically effective amount of a compound according to any one of embodiments 1 to 8 or a pharmaceutically acceptable salt thereof.

Embodiment 13

A compound according to any one of embodiments 1 to 8 or a pharmaceutically acceptable salt thereof, for use as a medicament.

Embodiment 14

A compound according to any one of embodiments 1 to 8 or a pharmaceutically acceptable salt thereof, for use in the treatment of a disorder or a disease selected from rheumatoid arthritis (RA), pemphigus vulgaris (PV), endemic form of Brazilian pemphigus (Fogo selvagem), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection, cancers of haematopoietic origin, severe and cerebral malaria, trypanosomiasis, leishmaniasis, toxoplasmosis and neurocysticercosis.

Embodiment 15

Use of a compound according to anyone of embodiments 1 to 8 or a pharmaceutically acceptable salt thereof in the manufacture of a medicament for the treatment of a disorder or a disease selected from rheumatoid arthritis (RA), pemphigus vulgaris (PV), endemic form of Brazilian pemphigus (Fogo selvagem), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection, cancers of haematopoietic origin, severe and cerebral malaria, trypanosomiasis, leishmaniasis, toxoplasmosis and neurocysticercosis.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula (I) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, DMSO-d6.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by class I PI3 kinases or (ii) associated with class I PI3 kinase activity, or (iii) characterized by activity (normal or abnormal) of class I PI3 kinases or (2) reduce or inhibit the activity of class I PI3 kinases or (3) reduce or inhibit the expression of class I PI3 kinases. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of class I PI3 kinases; or at least partially reducing or inhibiting the expression of class I PI3 kinases. The meaning of the term "a therapeutically effective amount" as illustrated in the above embodiment for class I PI3 kinases also applies by the same means to any other relevant proteins/peptides/enzymes.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. Diastereomeric atropisomers may be present in certain compounds of formula (I) e.g. with respect to hindered rotation around bond N—$R^1$.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Typically, the compounds of formula (I) can be prepared according to the methods provided infra.

Scheme A

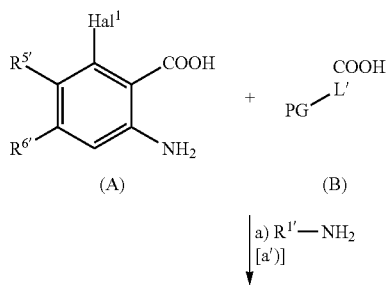

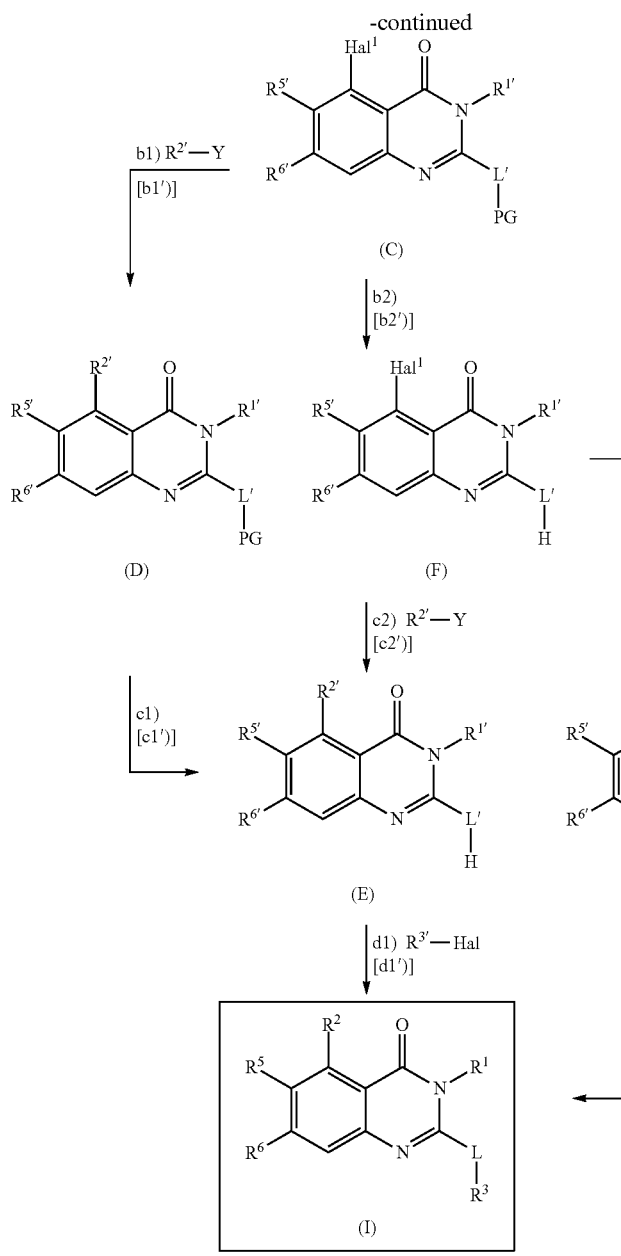

In one embodiment, the invention relates to a process for manufacturing a compound of formula (I) according to steps a, a', b1, b1', c1, c1', d1 and d1' (Scheme A), wherein a', b1', c1' and d1' denote optional functionalization steps or functional group adjustment steps, as required.

In another embodiment, the invention relates to a process for manufacturing a compound of formula (I) according to steps a, a', b2, b2', c2, c2', d1 and d1' (Scheme A), wherein a', b2', c2' and d1' denote optional functionalization steps or functional group adjustment steps, as required.

In another embodiment, the invention relates to a process for manufacturing a compound of formula (I) according to steps a, a', b2, b2', c3, c3', d2 and d2' (Scheme A), wherein a', b2', c3' and d2' denote optional functionalization steps or functional group adjustment steps, as required.

In one embodiment, the compound of formula (I) is obtained via the coupling reaction step d1 of a compound of formula (E),

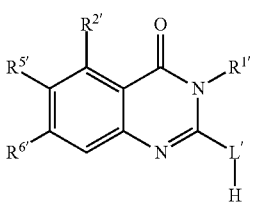

wherein
$R^{1'}$ is $R^1$, as defined above for a compound of formula (I), or a substituent that can be transferred into $R^1$ via functionalization steps or functional group adjustment steps;
$R^{2'}$ is $R^2$, as defined above for a compound of formula (I), or a substituent that can be transferred into $R^2$ via functionalization steps or functional group adjustment steps;

R<sup>5'</sup> is R<sup>5</sup>, as defined above for a compound of formula (I), or a substituent that can be transferred into R<sup>5</sup> via functionalization steps or functional group adjustment steps;
R<sup>6'</sup> is R<sup>6</sup>, as defined above for a compound of formula (I), or a substituent that can be transferred into R<sup>6</sup> via functionalization steps or functional group adjustment steps; and
L' is L, as defined above for a compound of formula (I), or a substituent that can be transferred into L via functionalization steps or functional group adjustment steps;
with R<sup>3'</sup>-Hal wherein
R<sup>3'</sup> is R<sup>3</sup>, as defined above for a compound of formula (I), or a substituent that can be transferred into R<sup>3</sup> via functionalization steps or functional group adjustment steps; and
Hal represents halogen, such as chloro, bromo or iodo;
wherein in one embodiment, the coupling reaction is carried out in the presence of an amine base such as N,N-diisopropylethylamine. The reaction is carried out in the presence of an organic solvent such as an alcohol under microwave heating for 30 minutes to 8 hours or conventional heating in an oil bath for 30 minutes to 6 days at temperature ranges 120-160° C.;
Alternatively, the reaction is carried out under customary Buchwald-Hartwig conditions using a suitable Pd catalyst/ligand combination such as Pd$_2$(dba)$_3$/2-(dicyclohexylphosphino)biphenyl or Pd$_2$(dba)$_3$/2-dicyclohexylphosphino-2',4',6'-triisopropyl-biphenyl, Pd$_2$(dba)$_3$/XPhos, Pd$_2$(dba)$_3$/(rac)-BINAP, Pd(OAc)$_2$/(rac)-BINAP or bis(tri-t-butylphosphine) palladium and a suitable base, such as NaOtBu, Cs$_2$CO$_3$ or K$_3$PO$_4$ and organic solvent such as toluene, dioxane or THF. The reaction is stirred at a temperature of approximately 60-140° C., for example at 100° C. to 110° C. and is optionally performed in a microwave reactor. The reaction is preferably carried out under an inert gas such as nitrogen or argon;
optionally followed by functionalization steps or functional group adjustment steps d1'.
The compound of formula (E) is obtained via step c1 of deprotecting PG from the compound of formula (D),

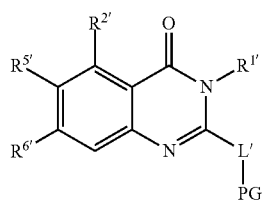

(D)

wherein PG represents a suitable protecting group, such as a Boc group, and the other substituents are as defined above;
wherein in one embodiment, where PG is a Boc group, the deprotection reaction is carried out in an organic solvent such as THF or DCM in the presence of an organic acid, such as trifluoroacetic acid at room temperature for 1-18 hours; or in the presence of an inorganic acid such as HCl or H$_3$PO$_4$, optionally in the presence of water at room temperature for 24 hours to 6 days;
optionally followed by functionalization steps or functional group adjustment steps c1'.
The compound of formula (D) is obtained via coupling step b1 of the compound of formula (C),

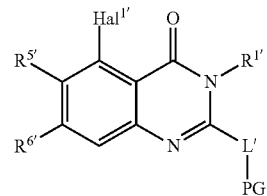

(C)

wherein PG represents a suitable protecting group, such as a Boc group, Hal<sup>1</sup> represents a halogen, such as a bromide or a chloride or a pseudohalogen such as a triflate, and the other substituents are as defined above;
with R<sup>2'</sup>—Y wherein when R<sup>2'</sup> is C$_4$-C$_7$-heteroaryl, as defined above as R<sup>2</sup> for a compound of formula (I), or a substituent that can be transferred into C$_4$-C$_7$-heteroaryl, via functionalization steps or functional group adjustment steps
Y represents a boronic acid residue or a cyclic or acyclic borolanyl, such as —B(OH)$_2$ or pinaccolato-boron; or an alkylstannyl, such as tributylstannyl
wherein when R<sup>2'</sup> is C$_2$-C$_5$-alkynyl, as defined above as R<sup>2</sup> for a compound of formula (I), or a substituent that can be transferred into C$_2$-C$_5$-alkynyl, via functionalization steps or functional group adjustment steps
Y is H (for a terminal alkyne) or Y represents an alkylstannyl (non terminal alkyne) under customary reaction conditions of the Suzuki reaction (Y is boronic acid residue or a cyclic or acyclic boronate ester), the Stille reaction (Y is alkylstannyl) or the Sonogashira coupling (Y is H of a terminal alkyne), typical reaction conditions are known in the field and may applied to the present process.
Typical conditions for the Suzuki reaction involve for example the presence of a Palladium catalyst, such as a Pd(0) catalyst, e.g. Pd(PPh$_3$)$_4$, or a Pd(II) catalyst such as PdCl$_2$(PPh$_3$)$_2$; Pd(OAc)$_2$ optionally in the presence of a phosphine ligand such a BrettPhos; or Brettphos palladacycle optionally in the presence of one or more reaction aids, such as a base, e.g. NaOEt, Na$_2$CO$_3$ solid or in aqueous solution, optionally in the presence of one or more diluents, particularly apolar solvents, e.g. benzene or toluene, or polar solvents, e.g. acetonitrile or N-methyl-2-pyrrolidon. The reaction is stirred at a temperature of approximately 100-180° C. e.g. in a microwave oven. The reaction may be carried out under an inert gas such as nitrogen or argon.
Typical conditions for the Stille reaction involve for example the presence of a Palladium catalyst, such as a Pd(0) catalyst, e.g. bis(tri-t-butylphosphine) palladium or Pd$_2$(dba)$_3$ optionally in the presence of one or more reaction aids, such as lithium chloride, in the presence of a solvent, e.g. dioxane or DMF. The reaction is stirred at a temperature of approximately 80160° C., typically 80-100° C. The reaction is carried out under an inert gas such as nitrogen or argon.
Typical conditions for the Sonogashira coupling involve the presence of a Palladium catalyst, such as a Pd(0) catalyst, e.g. Pd(PPh$_3$)$_4$ or Pd$_2$(dba)$_3$ and a copper(I) salt such as a copper halide such as CuI optionally in the presence of one or more reaction aids, such as a base, typically an amine base such as diethylamine or triethylamine or potassium carbonate or cesium carbonate, optionally in the presence of a solvent, e.g. DMF or an ether solvent. The reaction is stirred at a temperature of approximately room temperature –130°

C., typically 80° C. The reaction may be carried out under an inert gas such as nitrogen or argon.

Step b1 is optionally followed by functionalization steps or functional group adjustment steps b1'.

The compound of formula (C) is obtained via step a of reacting a compound of formula (A),

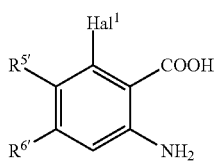
(A)

wherein the substituents are as defined above;
with a compound of formula (B),

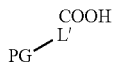
(B)

wherein the substituents are as defined above;
followed by reaction with R$^{1'}$—NH$_2$
wherein R$^{1'}$ is as defined above;
wherein in one embodiment, step a is carried out in the presence of pyridine and triphenylphosphite at elevated temperatures, such as 50-100° C., typically 70° C. for 0.5 to 30 h, for example for 2 to 18 h;
optionally followed by functionalization steps or functional group adjustment steps a'.

In another embodiment, the compound of formula (I) is obtained via the coupling reaction step d1 of a compound of formula (E),

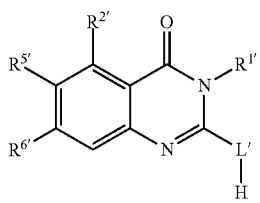
(E)

wherein
R$^{1'}$ is R$^1$, as defined above for a compound of formula (I), or a substituent that can be transferred into R$^1$ via functionalization steps or functional group adjustment steps;
R$^{2'}$ is R$^2$, as defined above for a compound of formula (I), or a substituent that can be transferred into R$^2$ via functionalization steps or functional group adjustment steps;
R$^{5'}$ is R$^5$, as defined above for a compound of formula (I), or a substituent that can be transferred into R$^5$ via functionalization steps or functional group adjustment steps;
R$^{6'}$ is R$^6$, as defined above for a compound of formula (I), or a substituent that can be transferred into R$^6$ via functionalization steps or functional group adjustment steps; and
L' is L, as defined above for a compound of formula (I), or a substituent that can be transferred into L via functionalization steps or functional group adjustment steps;
with R$^{3'}$-Hal wherein
R$^{3'}$ is R$^3$, as defined above for a compound of formula (I), or a substituent that can be transferred into R$^3$ via functionalization steps or functional group adjustment steps; and
Hal represents halogen, such as chloro, bromo or iodo;
wherein in one embodiment, the coupling reaction is carried out in the presence of an amine base such as N,N-diisopropylethylamine. The reaction is carried out in the presence of an organic solvent such as an alcohol under microwave heating or conventional heating in an oil bath at a temperature range from 120-160° C. for 30 minutes to 6 days;
Alternatively, the reaction is carried out under customary Buchwald-Hartwig conditions using a suitable Pd catalyst/ligand combination such as Pd$_2$(dba)$_3$/2-(dicyclohexylphosphino)biphenyl or Pd$_2$(dba)$_3$/2-dicyclohexylphosphino-2',4',6'-triisopropyl-biphenyl, Pd$_2$(dba)$_3$/XPhos, Pd$_2$(dba)$_3$/(rac)-BINAP, Pd(OAc)$_2$/(rac)-BINAP or bis(tri-t-butylphosphine)palladium and a suitable base, such as NaOtBu, Cs$_2$CO$_3$ or K$_3$PO$_4$ and organic solvent such as toluene, dioxane or THF. The reaction is stirred at a temperature of approximately 60-140° C., for example at 100° C. to 110° C. and is optionally performed in a microwave reactor. The reaction is preferably carried out under an inert gas such as nitrogen or argon;
optionally followed by functionalization steps or functional group adjustment steps d1'.

The compound of formula (E) is obtained via coupling step c2 of the compound of formula (F),

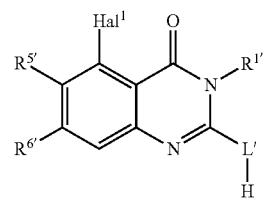
(F)

wherein Hal$^1$ represents a halogen, such as a bromide or a chloride or a pseudohalogen such as a triflate, and the other substituents are as defined above;
with

R$^{2'}$—Y wherein when R$^{2'}$ is C$_4$-C$_7$-heteroaryl, as defined above as R$^2$ for a compound of formula (I), or a substituent that can be transferred into C$_4$-C$_7$-heteroaryl, via functionalization steps or functional group adjustment steps
Y represents a boronic acid residue or a cyclic or acyclic borolanyl, such as —B(OH)$_2$ or pinaccolato-boron; or an alkylstannyl, such as tributylstannyl
wherein when R$^{2'}$ is C$_2$-C$_5$-alkynyl, as defined above as R$^2$ for a compound of formula (I), or a substituent that can be transferred into C$_2$-C$_5$-alkynyl, via functionalization steps or functional group adjustment steps
Y is H (for a terminal alkyne) or Y represents an alkylstannyl (non terminal alkyne) under customary reaction conditions of the Suzuki reaction (Y is boronic acid residue or a cyclic or acyclic borolanyl), the Stille reaction (Y is alkylstannyl) or the Sonogashira coupling (Y is H of a terminal alkyne), typical reaction conditions are known in the field and may applied to the present process. Typical conditions for the Suzuki reaction involve for example the presence of a Palladium catalyst, such as a Pd(0) catalyst, e.g. Pd(PPh$_3$)$_4$, or a Pd(II) catalyst such as PdCl$_2$(PPh$_3$)$_2$; Pd(OAc)$_2$ optionally in the presence of a phosphine ligand such a BrettPhos; or Brettphos palladacycle optionally in the presence of one or more reaction aids, such as a base, e.g. NaOEt, Na₂CO₃ solid or in aqueous solution, optionally in the presence of one or more diluents, particularly polar solvents, e.g. benzene, toluene, acetonitrile or N-methyl-2-pyrrolidon. The reaction is stirred at a temperature of approximately 100-180° C. e.g. in a microwaves oven. The reaction may be carried out under an inert gas such as nitrogen or argon. Typical conditions for the Stille reaction involve for example the presence of a Palladium catalyst, such as a Pd(0) catalyst, e.g. bis(tri-t-butylphosphine) palladium or Pd₂(dba)₃ optionally in the presence of one or more reaction aids, such as lithium chloride, in the presence of a solvent, e.g. DMF. The reaction is stirred at a temperature of approximately 100-160° C. The reaction is carried out under an inert gas such as nitrogen or argon. Typical conditions for the Sonogashira coupling involve the presence of a Palladium catalyst, such as a Pd(0) catalyst, e.g. Pd(PPh₃)₄ or Pd₂(dba)₃ and a copper(I) salt such as a copper halide such as CuI optionally in the presence of one or more reaction aids, such as a base, typically an amine base such as diethylamine or triethylamine or potassium carbonate or cesium carbonate, optionally in the presence of a solvent, e.g. DMF or an ether solvent. The reaction is stirred at a temperature of approximately 60-130° C. The reaction may be carried out under an inert gas such as nitrogen or argon.

Step c2 is optionally followed by functionalization steps or functional group adjustment steps c2'.

The compound of formula (F) is obtained via step b2 of deprotecting PG from the compound of formula (C),

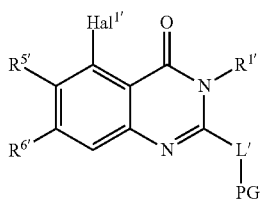

(C)

wherein PG represents a suitable protecting group, such as a Boc group, and the other substituents are as defined above; wherein in one embodiment, where PG is a Boc group, the deprotection reaction is carried out in an organic solvent such as THF or DCM in the presence of an organic acid, such as trifluoroacetic acid or in the presence of an inorganic acid such as HCl or H₃PO₄, optionally in the presence of water. The reaction is stirred at room temperature for approximately 60-140° C., for example at 100° C. to 110° C.;

optionally followed by functionalization steps or functional group adjustment steps b2'.

The compound of formula (C) is obtained via step a of reacting a compound of formula (A),

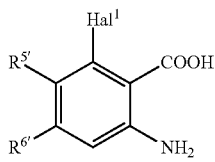

(A)

wherein the substituents are as defined above;

with a compound of formula (B),

(B)

wherein the substituents are as defined above;
followed by reaction with R¹'—NH₂
wherein R¹' is as defined above;
wherein in one embodiment, step a is carried out in the presence of pyridine and triphenylphosphite at elevated temperatures, such as 50-100° C. for 0.5 to 30 h, for example for 2 to 18 h;
optionally followed by functionalization steps or functional group adjustment steps a'.

In another embodiment, the compound of formula (I) is obtained via the coupling reaction step d2 of a compound of formula (G),

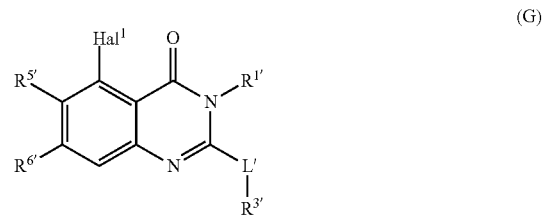

(G)

wherein
Hal¹ represents a halogen, such as a bromide or a chloride or a pseudohalogen such as a triflate;
R¹' is R¹, as defined above for a compound of formula (I), or a substituent that can be transferred into R¹ via functionalization steps or functional group adjustment steps;
R⁵' is R⁵, as defined above for a compound of formula (I), or a substituent that can be transferred into R⁵ via functionalization steps or functional group adjustment steps;
R⁶' is R⁶, as defined above for a compound of formula (I), or a substituent that can be transferred into R⁶ via functionalization steps or functional group adjustment steps; and
L' is L, as defined above for a compound of formula (I), or a substituent that can be transferred into L via functionalization steps or functional group adjustment steps;
with

R²'—Y wherein when R²' is C₄-C₇-heteroaryl, as defined above as R² for a compound of formula (I), or a substituent that can be transferred into C₄-C₇-heteroaryl, via functionalization steps or functional group adjustment steps
Y represents a boronic acid residue or a cyclic or acyclic borolanyl, such as —B(OH)₂ or pinaccolato-boron; or an alkylstannyl, such as tributylstannyl
wherein when R²' is C₂-C₅-alkynyl, as defined above as R² for a compound of formula (I), or a substituent that can be transferred into C₂-C₅-alkynyl, via functionalization steps or functional group adjustment steps
Y is H (for a terminal alkyne) or Y represents an alkylstannyl (non terminal alkyne) under customary reaction conditions of the Suzuki reaction (Y is boronic acid residue or a cyclic or acyclic borolanyl), the Stille reaction (Y is alkylstannyl) or the Sonogashira coupling (Y is H of a terminal alkyne), typical reaction conditions are known in the field and may applied to the present process. Typical conditions for the Suzuki reaction involve for example the presence of a Palladium catalyst, such as a Pd(0) catalyst, e.g. Pd(PPh$_3$)$_4$, or a Pd(II) catalyst such as PdCl$_2$(PPh$_3$)$_2$; Pd(OAc)$_2$ optionally in the presence of a phosphine ligand such a BrettPhos/ or Brettphos palladacycle optionally in the presence of one or more reaction aids, such as a base, e.g. NaOEt, Na$_2$CO$_3$ solid or in aqueous solution, optionally in the presence of one or more diluents, particularly polar solvents, e.g. benzene, toluene, acetonitrile or N-methyl-2-pyrrolidon. The reaction is stirred at a temperature of approximately 100-180° C. e.g. in a microwaves oven. The reaction may be carried out under an inert gas such as nitrogen or argon. Typical conditions for the Stille reaction involve for example the presence of a Palladium catalyst, such as a Pd(0) catalyst, e.g. bis(tri-t-butylphosphine) palladium or Pd$_2$(dba)$_3$ optionally in the presence of one or more reaction aids, such as lithium chloride, in the presence of a solvent, e.g. DMF. The reaction is stirred at a temperature of approximately 100-160° C. The reaction is carried out under an inert gas such as nitrogen or argon. Typical conditions for the Sonogashira coupling involve the presence of a Palladium catalyst, such as a Pd(0) catalyst, e.g. Pd(PPh$_3$)$_4$ or Pd$_2$(dba)$_3$ and a copper(I) salt such as a copper halide such as CuI optionally in the presence of one or more reaction aids, such as a base, typically an amine base such as diethylamine or triethylamine or potassium carbonate or cesium carbonate, optionally in the presence of a solvent, e.g. DMF or an ether solvent. The reaction is stirred at a temperature of approximately 60-130° C. The reaction may be carried out under an inert gas such as nitrogen or argon.

Step c2 is optionally followed by functionalization steps or functional group adjustment steps d2'.

The compound of formula (G) is obtained via coupling step c3 from the compound of formula (F),

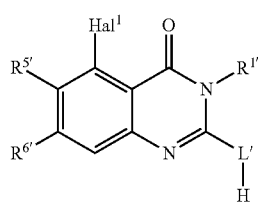

(F)

wherein the substituents are as defined above; with

R$^{3'}$-Hal wherein
R$^{3'}$ is R$^3$, as defined above for a compound of formula (I), or a substituent that can be transferred into R$^3$ via functionalization steps or functional group adjustment steps; and
Hal represents halogen, such as chloro, bromo or iodo;
wherein in one embodiment, the coupling reaction is carried out in the presence of an amine base such as N,N-diisopropylethylamine. The reaction is carried out in the presence of an organic solvent such as an alcohol under microwave heating or conventional heating in an oil bath at a temperature range from 120-160° C. for 30 minutes to 6 days;
Alternatively, the reaction is carried out under customary Buchwald-Hartwig conditions using a suitable Pd catalyst/ligand combination such as Pd$_2$(dba)$_3$/2-(dicyclohexylphosphino)biphenyl or Pd$_2$(dba)$_3$/2-dicyclohexylphosphino-2',4',6'-triisopropyl-biphenyl, Pd$_2$(dba)$_3$/XPhos, Pd$_2$(dba)$_3$/(rac)-BINAP, Pd(OAc)$_2$/(rac)-BINAP or bis(tri-t-butylphosphine) palladium and a suitable base, such as NaOtBu, Cs$_2$CO$_3$ or K$_3$PO$_4$ and organic solvent such as toluene, dioxane or THF. The reaction is stirred at a temperature of approximately 60-140° C., for example at 100° C. to 110° C. and is optionally performed in a microwave reactor. The reaction is preferably carried out under an inert gas such as nitrogen or argon;
optionally followed by functionalization steps or functional group adjustment steps c3'.

The compound of formula (F) is obtained via step b2 of deprotecting PG from the compound of formula (C),

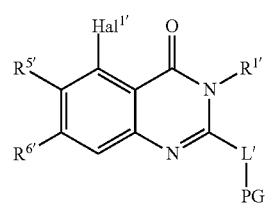

(C)

wherein PG represents a suitable protecting group, such as a Boc group, and the other substituents are as defined above;
wherein in one embodiment, where PG is a Boc group, the deprotection reaction is carried out in an organic solvent such as THF or DCM in the presence of an organic acid, such as trifluoroacetic acid or in the presence of an inorganic acid such as HCl or H$_3$PO$_4$, optionally in the presence of water. The reaction is stirred at room temperature for approximately 60-140° C., for example at 100° C. to 110° C.;
optionally followed by functionalization steps or functional group adjustment steps b2'.

The compound of formula (C) is obtained via step a of reacting a compound of formula (A),

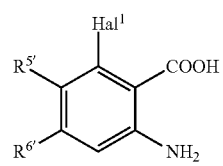

(A)

wherein the substituents are as defined above;
with a compound of formula (B),

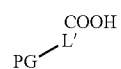

(B)

wherein the substituents are as defined above;
followed by reaction with R$^{1'}$—NH$_2$
wherein R$^{1'}$ is as defined above;
wherein in one embodiment, step a is carried out in the presence of pyridine and triphenylphosphite at elevated temperatures, such as 50-100° C. for 0.5 to 30 h, for example for 2 to 18 h;
optionally followed by functionalization steps or functional group adjustment steps a'.

The term "protecting group" as used herein relates to a group that protects a functional group which is present in the starting materials and is not intended to take part in the reaction. In additional process steps, carried out as desired, functional groups of the starting compounds which should not take part in the reaction may be present in unprotected form or may be protected for example by one or more protecting groups. The protecting groups are then wholly or partly removed according to one of the known methods. Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein above.

The solvents from which those solvents that are suitable for any particular reaction may be selected include those mentioned specifically or, for example, water, esters, such as $C_1$-$C_8$-alkyl-$C_1$-$C_8$-alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as $C_1$-$C_8$-alkanoic acid anhydrides, for example acetic anhydride, cyclic, linear or branched hydrocarbons, such as cyclohexane, hexane or isopentane, methylcyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

In another aspect, the present invention provides a intermediate of formula (E)

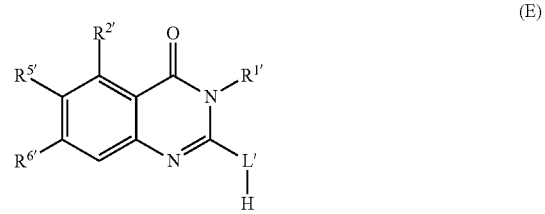

wherein
$R^{1'}$ is $R^1$, as defined above for a compound of formula (I), or a substituent that can be transferred into $R^1$ via functionalization steps or functional group adjustment steps;
$R^{2'}$ is $R^2$, as defined above for a compound of formula (I), or a substituent that can be transferred into $R^2$ via functionalization steps or functional group adjustment steps;
$R^{5'}$ is $R^5$, as defined above for a compound of formula (I), or a substituent that can be transferred into $R^5$ via functionalization steps or functional group adjustment steps;
$R^{6'}$ is $R^6$, as defined above for a compound of formula (I), or a substituent that can be transferred into $R^6$ via functionalization steps or functional group adjustment steps; and
L' is L, as defined above for a compound of formula (I), or a substituent that can be transferred into L via functionalization steps or functional group adjustment steps.

In another aspect, the present invention provides a intermediate of formula (D)

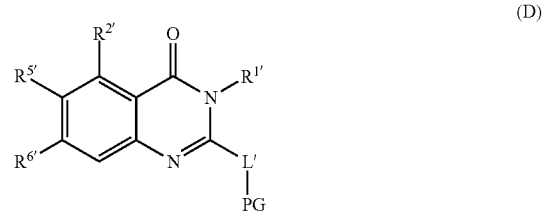

wherein PG represents a suitable protecting group, such as a Boc group, and the other substituents are as defined above.

In another aspect, the present invention provides a intermediate of formula (C)

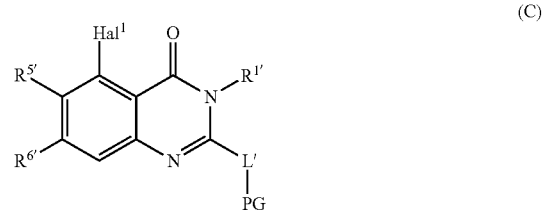

wherein Hal$^1$ represents a halogen, such as a bromide or a chloride or a pseudohalogen such as a triflate, and the other substituents are as defined above.

In another aspect, the present invention provides a intermediate of formula (F)

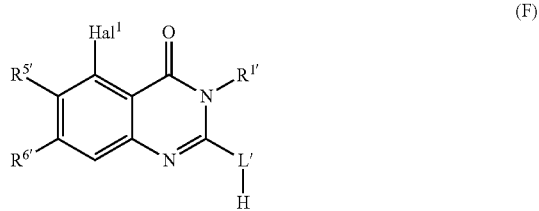

wherein the substituents are as defined above.

In another aspect, the present invention provides a intermediate of formula (G)

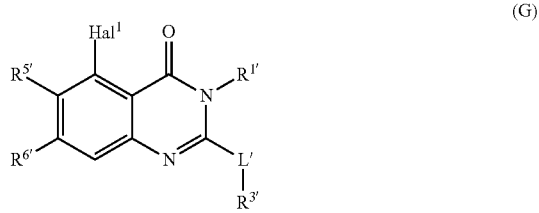

wherein the substituents are as defined above.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula (I) in free form or in pharmaceutically acceptable salt form, exhibit valuable pharmacological properties, e.g. class I PI3 kinase modulating properties, e.g. as indicated in in vitro and in vivo tests as provided in the next sections, and are therefore indicated for therapy or for use as research chemicals, e.g. as tool compounds.

Compounds of the invention may be useful in the treatment of conditions, diseases or disorders including disease or infection associated immunopathology in which one or more of the functions of B cells such as antibody production, antigen presentation, cytokine production or lymphoid organogenesis are abnormal or are undesirable including rheumatoid arthritis and related diseases (such as ankylosing spondylarthritis, psoriatic arthritis, juvenile arthritis), pemphigus vulgaris and related diseases, idiopathic thrombocytopenia purpura, systemic lupus erythematosus, multiple sclerosis, myasthenia gravis, Sjögren's syndrome (such as primary Sjögren's syndrom (pSS)), Graft versus host disease, autoimmune hemolytic anemia, ANCA-associated vasculitides (such as Wegener disease, microscopic polyangiitis or Churg-Strauss syndrome), cryoglobulinemia, thrombotic thrombocytopenic purpura, ischemia-reperfusion injury, chronic autoimmune urticaria, allergy (atopic dermatitis, contact dermatitis, allergic rhinitis, allergic asthma, asthma associated with allergic rhinitis), Goodpasture's syndrome, different types of glomerulonephritides, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

The invention includes methods of treating conditions, diseases or disorders in which one or more of the functions of neutrophils, such as superoxide release, stimulated exocytosis, or chemoatractic migration are abnormal or are undesirable including rheumatoid arthritis, pulmonary or respiratory disorders such as asthma, inflammatory dermatoses such as psoriasis, as well as in disease or infection associated immunopathology and others.

The invention includes methods of treating conditions, diseases or disorders in which one or more of the functions of basophil and mast cells such as chemoatractic migration or allergen-IgE-mediated degranulation are abnormal or are undesirable including allergic diseases (atopic dermatitis, contact dermatitis, allergic rhinitis, allergic asthma, asthma associated with allergic rhinitis, chronic allergic urticaria) as well as other disorders such as COPD, asthma or emphysema.

The invention includes methods of treating conditions, diseases or disorders in which one or more of the functions of T cells such as cytokine production or cell-mediated cytotoxicity abnormal or are undesirable including rheumatoid arthritis, multiple sclerosis, acute or chronic rejection of cell tissue or organ grafts or cancers of haematopoietic origin as well as in disease or infection associated immunopathology.

Further, the invention includes methods of treating neurodegenerative diseases, cardiovascular diseases and platelet aggregation.

Further, the invention includes methods of treating skin diseases such as porphyria cutanea tarda, polymorphous light eruption, dermatomyositis, solar urticaria, oral lichen planus, panniculitis, scleroderma, urticarial vasculitis.

Further, the invention includes methods of treating chronic inflammatory diseases such as sarcoidosis, granuloma annulare.

In other embodiments, the condition or disorder (e.g. class I PI3 kinase-mediated) is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine ophthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy.

In another embodiment, the compounds of the present invention are useful in the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which compounds of the invention may be employed include autoimmune haematological disorders (including e.g. hemolytic anaemia, aplastic anaemia, pure red cell anaemia and idiopathic thrombocytopenia), acquired hemophilia A, cold agglutinin disease, cryoglobulinemia, thrombotic thrombocytopenic purpura, Sjögren's syndrome, systemic lupus erythematosus, inflammatory muscle disorders, polychondritis, sclerodoma, antineutrophil cytoplasmic antibody-associated vasculitis, IgM mediated neuropathy, opsoclonus myoclonus syndrome, Wegener granulomatosis, dermatomyositis, chronic active hepatitis, myasthenia gravis, psoriasis, Steven-Johnson syndrome, pemphigus vulgaris, pemphigus foliacius, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis, ancylosing spondylitis and glomerulonephritis (with and without nephrotic syndrome, e.g. including idiopathic nephrotic syndrome or minimal change nephropathy), tumors, inflammatory disease of skin and cornea, myositis, loosening of bone implants, metabolic disorders, such as atherosclerosis, diabetes, and dislipidemia.

In another embodiment, the compounds of the present invention are useful in the treatment of conditions or disorders selected from the group consisting of, primary cutaneous B-cell lymphoma, immunobullous disease, pemphigus vulgaris, pemphigus foliaceus, endemic form of Brazilian pemphigus (Fogo selvagem), paraneoplastic pemphigus, bullous pemphigoid, mucous membrane pemphigoid, epidermolysis bullosa acquisita, chronic graft versus host disease, dermatomyositis, systemic lupus erythematosus, vasculitis, small vessel vasculitis, hypocomplementemic urticarial vasculitis, antineutrophil cytoplasmic antibody-vasculitis, cryoglobulinemia, Schnitzler syndrome, Waldenstrom's macroglobulinemia, angioedema, vitiligo, systemic lupus erythematosus, idiopathic thrombocytopenic purpura, multiple sclerosis, cold agglutinin disease, autoimmune hemolytic anemia, antineutrophil cytoplasmic antibody-associated vasculitis, graft versus host disease, cryoglobulinemia and thrombotic thrombocytopenic.

Thus, as a further embodiment, the present invention provides the use of a compound of the formulae (I) or (I'), (I"), (Ia), (Ib), (IA), (IB) or (IC) in therapy. In a further embodiment, the therapy is selected from a disease which may be treated by inhibition of class I PI3 kinases. In another embodiment, the disease is selected from the afore-mentioned list, suitably from autoimmune disorders, autoinflammatory and inflammatory diseases, allergic diseases, airway diseases, such as asthma and COPD, transplant rejection; antibody production, antigen presentation, cytokine production or lymphoid organogenesis are abnormal or are undesirable including rheumatoid arthritis and related diseases (such as ankylosing spondylarthritis, psoriatic arthritis, juvenile arthritis), pemphigus vulgaris and related diseases, idiopathic thrombocytopenia purpura, systemic lupus erythematosus, multiple sclerosis, myasthenia gravis, Sjögren's syndrome (such as primary Sjögren's syndrom (pSS)), Graft versus host disease, autoimmune hemolytic anemia, ANCA-associated vasculitides (such as Wegener disease, microscopic polyangiitis or Churg-Strauss syndrome), cryoglobulinemia, thrombotic thrombocytopenic purpura, ischemia-reperfusion injury, chronic autoimmune urticaria, allergy (atopic dermatitis, contact dermatitis, allergic rhinitis, allergic asthma, asthma associated with allergic rhinitis), Goodpasture's syndrome, different types of glomerulonephritides, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS) (such as primary Sjögren's syndrom (pSS)), ANCA-associated vasculitides (such as Wegener disease, microscopic polyangiitis or Churg-Strauss syndrome), cryoglobulinemia, ischemia-reperfusion injury, chronic autoimmune urticaria (CAU), allergy (atopic dermatitis, contact dermatitis, allergic rhinitis, allergic asthma, asthma associated with allergic rhinitis), Goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

Thus, as a further embodiment, the present invention provides a compound of the formulae (I) or (I'), (I"), (Ia), (Ib), (IA), (IB) or (IC) for use in therapy. In a further embodiment, the therapy is selected from a disease which may be treated by inhibition of class I PI3 kinases.

In another embodiment, the disease is selected from the afore-mentioned list, suitably from autoimmune disorders, autoinflammatory and inflammatory diseases, allergic diseases, airway diseases, such as asthma and COPD, transplant rejection; antibody production, antigen presentation, cytokine production or lymphoid organogenesis are abnormal or are undesirable including rheumatoid arthritis and related diseases (such as ankylosing spondylarthritis, psoriatic arthritis, juvenile arthritis), pemphigus vulgaris and related diseases, idiopathic thrombocytopenia purpura, systemic lupus erythematosus, multiple sclerosis, myasthenia gravis, Sjögren's syndrome (such as primary Sjögren's syndrom (pSS)), Graft versus host disease, autoimmune hemolytic anemia, ANCA-associated vasculitides (such as Wegener disease, microscopic polyangiitis or Churg-Strauss syndrome), cryoglobulinemia, thrombotic thrombocytopenic purpura, ischemia-reperfusion injury, chronic autoimmune urticaria, allergy (atopic dermatitis, contact dermatitis, allergic rhinitis, allergic asthma, asthma associated with allergic rhinitis), Goodpasture's syndrome, different types of glomerulonephritides, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS) (such as primary Sjögren's syndrom (pSS)), ANCA-associated vasculitides (such as Wegener disease, microscopic polyangiitis or Churg-Strauss syndrome), cryoglobulinemia, ischemia-reperfusion injury, chronic autoimmune urticaria (CAU), allergy (atopic dermatitis, contact dermatitis, allergic rhinitis, allergic asthma, asthma associated with allergic rhinitis), Goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

In another embodiment, the invention provides a method of treating a disease which is treated by inhibition of class I PI3 kinases comprising administration of a therapeutically acceptable amount of a compound of the formulae (I) or (I'), (I''), (Ia), (Ib), (IA), (IB) or (IC). In a further embodiment, the disease is selected from the afore-mentioned list, suitably from autoimmune disorders, autoinflammatory and inflammatory diseases, allergic diseases, airway diseases, such as asthma and COPD, transplant rejection; antibody production, antigen presentation, cytokine production or lymphoid organogenesis are abnormal or are undesirable including rheumatoid arthritis and related diseases (such as ankylosing spondylarthritis, psoriatic arthritis, juvenile arthritis), pemphigus vulgaris and related diseases, idiopathic thrombocytopenia purpura, systemic lupus erythematosus, multiple sclerosis, myasthenia gravis, Sjögren's syndrome (such as primary Sjögren's syndrom (pSS)), Graft versus host disease, autoimmune hemolytic anemia, ANCA-associated vasculitides (such as Wegener disease, microscopic polyangiitis or Churg-Strauss syndrome), cryoglobulinemia, thrombotic thrombocytopenic purpura, ischemia-reperfusion injury, chronic autoimmune urticaria, allergy (atopic dermatitis, contact dermatitis, allergic rhinitis, allergic asthma, asthma associated with allergic rhinitis), Goodpasture's syndrome, different types of glomerulonephritides, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS) (such as primary Sjögren's syndrom (pSS)), ANCA-associated vasculitides (such as Wegener disease, microscopic polyangiitis or Churg-Strauss syndrome), cryoglobulinemia, ischemia-reperfusion injury, chronic autoimmune urticaria (CAU), allergy (atopic dermatitis, allergic rhinitis, allergic asthma, asthma associated with allergic rhinitis), Goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

Thus, as a further embodiment, the present invention provides the use of a compound of the formulae (I) or (I'), (I''), (Ia), (Ib), (IA), (IB) or (IC) for the manufacture of a medicament. In a further embodiment, the medicament is for treatment of a disease which may be treated inhibition of class I PI3 kinases. In another embodiment, the disease is selected from the afore-mentioned list, suitably from autoimmune disorders, autoinflammatory and inflammatory diseases, allergic diseases, airway diseases, such as asthma and COPD, transplant rejection; antibody production, antigen presentation, cytokine production or lymphoid organogenesis are abnormal or are undesirable including rheumatoid arthritis arthritis and related diseases (such as ankylosing spondylarthritis, psoriatic arthritis, juvenile arthritis), pemphigus vulgaris and related diseases, idiopathic thrombocytopenia purpura, systemic lupus erythematosus, multiple sclerosis, myasthenia gravis, Sjögren's syndrome (such as primary Sjögren's syndrom (pSS)), Graft versus host disease, autoimmune hemolytic anemia, ANCA-associated vasculitides (such as Wegener disease, microscopic polyangiitis or Churg-Strauss syndrome), cryoglobulinemia, thrombotic thrombocytopenic purpura, ischemia-reperfusion injury, chronic autoimmune urticaria, allergy (atopic dermatitis, contact dermatitis, allergic rhinitis, allergic asthma, asthma associated with allergic rhinitis), Goodpasture's syndrome, different types of glomerulonephritides, AMR (antibody-mediated transplant rejection), B cell-mediated hyperacute, acute and chronic transplant rejection and cancers of haematopoietic origin including but not limited to multiple myeloma; a leukaemia; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease; more suitably from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS) (such as primary Sjögren's syndrom (pSS)), ANCA-associated vasculitides (such as Wegener disease, microscopic polyangiitis or Churg-Strauss syndrome), cryoglobulinemia, ischemia-reperfusion injury, chronic autoimmune urticaria (CAU), allergy (atopic dermatitis, contact dermatitis, allergic rhinitis, allergic asthma, asthma associated with allergic rhinitis), Goodpasture's syndrome, transplant rejection and cancers of haematopoietic origin as well as in disease or infection associated immunopathology, for example in severe and cerebral malaria, trypanosomiasis, leishmaniasis, toxoplasmosis and neurocysticercosis.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by the activity of the class I PI3 kinases. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the activity of the class I PI3 kinases, wherein the medicament is prepared for administration with another therapeutic agent. The invention also provides the use of another therapeutic agent for treating a disease or condition mediated by the activity of the class I PI3 kinases, wherein the medicament is administered with a compound of formula (I).

The invention also provides a compound of formula (I) for use in a method of treating a disease or condition mediated by the activity of the class I PI3 kinases enzymes, wherein the compound of formula (I) is prepared for administration with another therapeutic agent. The invention also provides another therapeutic agent for use in a method of treating a disease or condition mediated by the activity of the class I PI3 kinases, wherein the other therapeutic agent is prepared for administration with a compound of formula (I). The invention also provides a compound of formula (I) for use in a method of treating a disease or condition mediated by the activity of the class I PI3 kinases wherein the compound of formula (I) is administered with another therapeutic agent. The invention also provides another therapeutic agent for use in a method of treating a disease or condition mediated by the activity of class I PI3 kinases wherein the other therapeutic agent is administered with a compound of formula (I).

The invention also provides the use of a compound of formula (I) for treating a disease or condition mediated by the activity of the class I PI3 kinases, wherein the patient has previously (e.g. within 24 hours) been treated with another therapeutic agent. The invention also provides the use of another therapeutic agent for treating a disease or condition mediated by the activity of the class I PI3 kinases, wherein the patient has previously (e.g. within 24 hours) been treated with a compound of formula (I).

The compounds of formula (I) may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell antiproliferative agent. For example, the compounds of formula (I) may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, TAFA-93, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690, 550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

Where the compounds of formula (I) are administered in conjunction with other immunosuppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth.

A compound of the formula (I) may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds, which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901.

The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term "topoisomerase II inhibitor", as used herein, includes, but is not limited to, the anthracyclines, such as doxorubicin, including liposomal formulation, e.g., CAELYX; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel). Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN. The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the IGF-IR receptor, such as those compounds disclosed in WO 02/092599;

d) compounds targeting, decreasing or inhibiting the activity of the Trk receptor tyrosine kinase family;

e) compounds targeting, decreasing or inhibiting the activity of the Axl receptor tyrosine kinase family;

f) compounds targeting, decreasing or inhibiting the activity of the c-Met receptor;

g) compounds targeting, decreasing or inhibiting the activity of the Kit/SCFR receptor tyrosine kinase;

h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;

i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;

j) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352; or QAN697 (a P13K inhibitor);

k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemaloniirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG957 and adaphostin (4-{[(2,5-dihydroxyphenyl)methyl]amino}-benzoic acid adamantyl ester, NSC 680410, adaphostin; and l) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0 564 409; WO 99/03854; EP 0520722; EP 0 566 226; EP 0 787 722; EP 0 837 063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d]pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID) and TNP-470.

Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid or lumiracoxib.

The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL. "Clodronic acid" can be administered, e.g., in the form as it is marketed, e.g., under the trademark BONEFOS. "Tiludronic acid" can be administered, e.g., in the form as it is marketed, e.g., under the trademark SKELID. "Pamidronic acid" can be administered, e.g., in the form as it is marketed, e.g., under the trademark AREDIA™. "Alendronic acid" can be administered, e.g., in the form as it is marketed, e.g., under the trademark FOSAMAX. "Ibandronic acid" can be administered, e.g., in the form as it is marketed, e.g., under the trademark BONDRANAT. "Risedronic acid" can be administered, e.g., in the form as it is marketed, e.g., under the trademark ACTONEL. "Zoledronic acid" can be administered, e.g., in the form as it is marketed, e.g., under the trademark ZOMETA.

The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88.

The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R115777 (Zarnestra).

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransylcytosine (ara-c) and bisulfan; and ALK inhibitors, e.g., compounds which target, decrease or inhibit anaplastic lymphoma kinase. Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (Herceptin™), Trastuzumab-DM1, erlotinib (Tarceva™), bevacizumab (Avastin™), rituximab (Rituxan®), PRO64553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

A compound of the formula (I) may also be used to advantage in combination with each other or in combination with other therapeutic agents, especially other anti-malarial agents. Such anti-malarial agents include, but are not limited to proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, inhaled NO, L-arginine, Dipropylenetri-amine NONOate (NO donor), Rosiglitzone (PPARγ agonist), activated charcoal, Erythropoietin, Levamisole, and pyronaridine.

A compound of the formula (I) may also be used to advantage in combination with each other or in combination with other therapeutic agents, such as used for the treatment of Leishmaniosis, Trypanosomiasis, Toxoplasmosis and Neurocysticercosis. Such agents include, but are not limited to chloroquine sulfate, atovaquone-proguanil, artemether-lumefantrine, quinine-sulfate, artesunate, quinine, doxycycline, clindamycin, meglumine antimoniate, sodium stibogluconate, miltefosine, ketoconazole, pentamidine, amphotericin B (AmB), liposomal-AmB, paromomycine, eflornithine, nifurtimox, suramin, melarsoprol, prednisolone, benznidazole, sulfadiazine, pyrimethamine, clindamycin, trimetropim, sulfamethoxazole, azitromycin, atovaquone, dexamethasone, praziquantel, albendazole, beta-lactams, fluoroquinolones, macrolides, aminoglycosides, sulfadiazine and pyrimethamine.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound of the formula (I), can be prepared and administered as described in the art, such as in the documents cited above.

A compound of the formula (I) may also be used to advantage in combination with known therapeutic processes, e.g., the administration of hormones or especially radiation.

A compound of formula (I) may in particular be used as a radiosensitizer, especially for the treatment of tumors which exhibit poor sensitivity to radiotherapy.

EXAMPLES

Experimental Details

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Abbreviations
ACN acetonitrile
aq. aqueous
Boc tert-butoxycarbonyl
br. broad
Brettphos 2-(dicyclohexylphosphino)-3,6-dimethoxy-2',4', 6'-triisopropyl-1, 1'-biphenyl
Brettphos Palladacycle chloro[2-(dicyclohexylphosphino)-3,6-dimethoxy-2',4',6'-triisopropyl-1,1'-biphenyl][2-(2-aminoethyl)phenyl]palladium(II)
CuI copper (I) iodide
$CuSO_4$ copper (II) sulfate
d day(s), doublet
DCM dichloromethane
DIPEA diisopropylethylamine
DMF dimethylformamide
DMSO dimethylsulfoxide
eq. equivalent(s)
ESI electrospray ionisation
$Et_3N$ triethylamine
EtOAc ethyl acetate
EtOH ethanol
h hour(s)
$HNO_3$ nitric acid
HPLC high performance liquid chromatography
$H_3PO_4$ phosphoric acid
$H_2SO_4$ sulfuric acid
$K_2CO_3$ potassium carbonate
LCMS liquid chromatography with mass spectrometry
MeOH methanol
m multiplet
min minute(s)
MS mass spectrometry
mw microwave
$Na_2CO_3$ sodium carbonate
$NaHCO_3$ sodium bicarbonate
$Na_2SO_4$ sodium sulfate
nBuOH n-butanol
NMP N-Methyl-2-pyrrolidone
NMR nuclear magnetic resonance spectrometry
$Pd(OAc)_2$ palladium diacetate
$Pd(PPh_3)_4$ tetrakis(triphenylphosphine)palladium(0)
$PdCl_2(PPh_3)_2$ bis(triphenylphosphine)palladium(II) dichloride
RP reversed phase
rpm revolutions per minute
Rt retention time
rt room temperature
sat. saturated
SFC supercritical fluid chromatography
soln. solution
t-butyl tert-butyl
TFA trifluoroacetic acid
THF tetrahydrofuran
UPLC ultra performance liquid chromatography
Microwave equipment used is a Biotage Initiator®
All compounds are named using ChemDraw® Ultra software or commercial names have been used.
General Chromatography Information
LCMS Method Used for all Examples
HPLC column dimensions: 2.1×50 mm
HPLC column type: Acquity UPLC HSS T3, 1.8 μm
HPLC eluent: A) water+0.05 vol % formic acid+3.75 mM ammonium acetate B) ACN+0.04 vol % formic acid HPLC gradient: 5-98% B in 1.4 min, 98% B 0.4 min, flow=1.0 ml/min
HPLC column temperature: 60° C.
X-ray Powder Diffraction
Instrumentation and Method

| Instrument | Bruker D8 advantage |
|---|---|
| Geometry | Reflection |
| Detector | Vantec |
| Scan range | 2°-40° (2-Theta) |
| Irradiation | CuKα (40 kV, 40 mA) |
| Measurment at | Room temperature |

Differential Scanning Calorimetry
Instrumentation and Method
Instrument: Mettler Toledo DSC Star System
Temperature range: 30-300° C.
Scan rate: 10° C./min
Nitrogen flow: 45 ml/min Preparation of Examples Where it is stated that compounds were prepared in the manner described for an earlier example, the skilled person will appreciate that reaction times, number of equivalents of reagents and reaction temperatures may be modified for each specific reaction, and that it may nevertheless be necessary or desirable to employ different work-up or purification conditions. Compounds that show atropisomerism around bond N—R1 may be obtained as mixtures of diastereomeric atropisomers that may be separated by chromatographic conditions. These compounds are exemplified as mixtures and, if applicable, in addition as separated diastereomeric atropisomers, detailing the separation conditions in each case.

Example 1: 2-Amino-4-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)-6-methylpyrimidine-5-carbonitrile

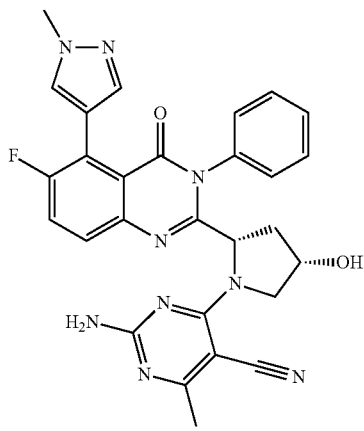

a) 2-Bromo-3-fluoro-6-nitrobenzoic Acid

A solution of 2-bromo-3-fluorobenzoic acid (CAS registry 132715-69-6) (5 g, 22.83 mmol) in $H_2SO_4$ conc. (15.82 ml, 297 mmol) was cooled to 0° C. and was treated dropwise with fuming $HNO_3$ (1.36 ml, 27.4 mmol). A white precipitate was formed. The resulting suspension was stirred at 0° C. for 1.5 h. The mixture was poured onto ice water and stirred for 30 min. The resulting mixture was diluted with water and extracted with DCM. Then, the organic phases were dried over $Na_2SO_4$ and concentrated under reduced pressure. This afforded an off-white solid (5.67 g, 94%) of a mixture of 2-bromo-3-fluoro-6-nitrobenzoic acid (regioisomer 1) and 2-bromo-3-fluoro-5-nitrobenzoic acid (regioisomer 2) in a ratio of ca. 2:1, which was used without separation for the next step.

HPLC $1^{st}$ regioisomer (69%) Rt=0.33 min; HPLC $2^{nd}$ regioisomer (30%) Rt=0.52 min.

b) 6-Amino-2-bromo-3-fluorobenzoic Acid

A mixture of 2-bromo-3-fluoro-6-nitrobenzoic acid and 2-bromo-3-fluoro-5-nitrobenzoic acid (5.60 g, 21.21 mmol, ratio ca. 2:1) was dissolved in THF (140 ml) and successively degassed and purged with nitrogen (5×). Then, the yellow solution was treated with 10% palladium on carbon (1.13 g, 1.06 mmol). The black mixture was purged, then backfilled with hydrogen gas and allowed to stir under hydrogen atmosphere at rt for 18 h. The reaction mixture was filtered through hyflo and the pad was rinsed with EtOAc (2×). The collected filtrates were evaporated in vacuo to afford a light brown solid (5.4 g, 90%) as a ca. 2:1 mixture of 6-amino-2-bromo-3-fluorobenzoic acid (regioisomer 1) and 5-amino-2-bromo-3-fluorobenzoic acid (regioisomer 2). The crude mixture was used without further purification for the next step.

HPLC $1^{st}$ regioisomer (67%) Rt=0.50 min; ESIMS: 234, 236 [(M+H)$^+$]
HPLC $2^{nd}$ regioisomer (33%) Rt=0.51 min; ESIMS: 234, 236 [(M+H)$^+$]

c) (2S,4S)-tert-Butyl 2-(5-bromo-6-fluoro-4-oxo-3-phenyl-3,4-dihydroquinazolin-2-yl)-4-((tert-butyldimethylsilyl)oxy)pyrrolidine-1-carboxylate A dry solution of a mixture of 6-amino-2-bromo-3-fluorobenzoic acid and 5-amino-2-bromo-3-fluorobenzoic acid (5.4 g, 13.84 mmol, ratio ca. 2:1) and (2S,4S)-1-(tert-butoxycarbonyl)-4-((tert-butyldimethylsilyl)oxy)pyrrolidine-2-carboxylic acid (CAS registry 401564-17-8) (7.97 g, 60% content, 13.84 mmol) in pyridine (25 ml) was treated with triphenylphosphite (CAS registry 101-02-0) (9.1 ml, 34.6 mmol). The light brown solution was stirred at 70° C. for 18 h and then aniline (CAS registry 62-53-3) (1.69 ml, 18.55 mmol) was added dropwise. After stirring the reaction mixture for another 3 h at 70° C., the pyridine was removed under reduced pressure and then the residue was diluted with EtOAc, washed with sat. aq. $NaHCO_3$ soln. (2×) and brine. The organic phases were dried over $Na_2SO_4$ and concentrated under reduced pressure. The crude product was purified by chromatography on silica gel (0 to 15% EtOAc/heptane) to provide the title compound as orange oil (1.70 g, 17% yield, 85% purity) which was used without further purification for the next step.

HPLC Rt=1.60 min; ESIMS: 618, 620 [(M+H)$^+$].

d) (2S,4S)-tert-Butyl 4-((tert-butyldimethylsilyl)oxy)-2-(6-fluoro-5-(1-methyl-1H-pyrazol-4-yl)-4-oxo-3-phenyl-3,4-dihydroquinazolin-2-yl)pyrrolidine-1-carboxylate A solution of (2S,4S)-tert-butyl 2-(5-bromo-6-fluoro-4-oxo-3-phenyl-3,4-dihydroquinazolin-2-yl)-4-((tert-butyldimethylsilyl)oxy)pyrrolidine-1-carboxylate (160 mg, 0.22 mmol, 85% content) in DMF (2 ml) was treated with 1-methyl-4-(tributylstannyl)-1H-pyrazole (CAS registry 179055-21-1) (93 μl, 0.27 mmol). Then, the reaction mixture was degassed with argon for 5 min and treated with bis(tri-t-butylphosphine)palladium(0) (CAS registry 53199-31-8) (11.24 mg, 0.022 mmol). The reaction mixture was stirred in a sealed vessel under argon atmosphere at 80° C. for 18 h, then diluted with EtOAc, filtered through a Biotage Universal Phase Separator cartridge and the combined organic phases were concentrated under reduced pressure. The crude product was purified by chromatography on silica gel (0 to 15% MeOH/DCM) to provide the title compound as yellow gum (127 mg, 75% yield, 80% purity) which was used without further purification for the next step.

HPLC Rt=1.51 min; ESIMS: 620 [(M+H)$^+$].

e) 6-Fluoro-2-((2S,4S)-4-hydroxypyrrolidin-2-yl)-5-(1-methyl-1H-pyrazol-4-yl)-3-phenylquinazolin-4(3H)-one At rt, a solution of (2S,4S)-tert-butyl 4-((tert-butyldimethylsilyl)oxy)-2-(6-fluoro-5-(1-methyl-1H-pyrazol-4-yl)-4-oxo-3-phenyl-3,4-dihydroquinazolin-2-yl)pyrrolidine-1-carboxylate (127 mg, 0.16 mmol, 80% purity) in THF (0.7 ml) was treated with aq. H$_3$PO$_4$ soln. (0.8 ml, 85 wt %). The mixture was stirred for 18 h at rt. Water was added and the mixture was basified with a sat. aq. NaHCO$_3$ soln. to pH~9. The mixture was extracted with EtOAc (2×) and DCM (2×), then the combined organic layers were dried over Na$_2$SO$_4$ and concentrated in vacuo to afford a yellow gum (80 mg, 96% yield, 80% purity) which was used without further purification for the next step).

HPLC Rt=0.49 min; ESIMS: 406 [(M+H)$^+$].

f) 2-Amino-4-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)-6-methylpyrimidine-5-carbonitrile A solution of 6-fluoro-2-((2S,4S)-4-hydroxypyrrolidin-2-yl)-5-(1-methyl-1H-pyrazol-4-yl)-3-phenylquinazolin-4(3H)-one (25 mg, 0.062 mmol) and 2-amino-4-chloro-6-methylpyrimidine-5-carbonitrile (CAS registry 99586-66-0) (10.40 mg, 0.062 mmol) in EtOH (1 ml) was treated with DIPEA (0.022 ml, 0.12 mmol) and was irradiated at 120° C. for 45 min in a mw.

The reaction mixture was evaporated under reduced pressure. The oil was taken up in DCM and washed with sat. aq. NaHCO$_3$ soln., the organic layer was dried over Na$_2$SO$_4$ and concentrated in vacuo. The crude was purified over RP-HPLC (column SunFire C18, 100×30 mm, 5 μm, flow at 30 ml/min; gradient of ACN+0.1% TFA in H$_2$O+0.1% TFA/ from 12% to 32% in 16 min, total run time: 20 min) to afford the title compound as a free base obtained by elution through a Varian ipe PL-HCO3 MP cartridge (22.2 mg, 67% yield) and subsequent evaporation.

HPLC Rt=0.81 min; ESIMS: 538 [(M+H)$^+$].

1H NMR (400 MHz, DMSO-d6): δ 7.75-7.83 (m, 1H) 7.62-7.74 (m, 2H) 7.46-7.60 (m, 4H) 7.34-7.45 (m, 2H) 6.33-7.18 (br. m, 2H) 5.09-5.40 (m, 1H) 4.47-4.76 (m, 1H) 4.15 (d, 2H) 3.81 (s, 3H) 3.61-3.75 (m, 1H) 2.27 (s, 3H) 1.94-2.09 (m, 1H) 1.80-1.93 (m, 1H).

Examples 2 to 33

The compounds listed in Tables 1-3 were prepared by a procedure analogous to that used in Example 1. The cross coupling of the R$^2$ moiety can be performed as second, third or fourth step of the sequence (see Scheme 1, 2 and 3, respectively)

Alternative for Example 7: 2-Amino-4-((2S,4S)-2-(6-fluoro-5-(2-methoxypyrimidin-5-yl)-4-oxo-3-phenyl-3,4-dihydroquinazolin-2-yl)-4-hydroxypyrrolidin-1-yl)-6-methylpyrimidine-5-carbonitrile a) 2-Bromo-3-fluoro-6-nitrobenzoic Acid A solution of 2-bromo-3-fluorobenzoic acid (CAS registry 132715-69-6) (155 g, 0.672 mol) in H$_2$SO$_4$ conc. (750 ml, 14 mol) was cooled to 0° C. and fuming HNO$_3$ (39 ml, 0.864 mol) was added dropwise over a period of 1 hour, keeping the temperature between 0-5° C. A white precipitate was formed. The resulting suspension was allowed to warm to ambient temperature and stirred for 3 h. The mixture was poured onto ice water (3 L), stirred for 30 min and extracted with 3×1 L DCM. The organic phases were combined, washed with brine and dried over sodium sulfate. After evaporation of the solvent, 160 g of an off-white solid was obtained as a mixture of 2-bromo-3-fluoro-6-nitrobenzoic acid (regioisomer 1) and 2-bromo-3-fluoro-5-nitrobenzoic acid (regioisomer 2) in a ratio of ca. 2:1. The crude product was dissolved in 2N NaOH (2 L) and the pH was adjusted to 2 by adding HCl conc. Extraction with 4×2 L ethyl acetate led to separation of regioisomer 2 in the organic phase, whereas regioisomer 1 mainly remained in the aqueous phase. After the removal of regioisomer 2, the aqueous phase was set to pH1 by adding more HCl conc. and extracted a second time with 2×1 L ethyl acetate. The organic phase was washed with brine, dried over sodium sulfate and evaporated to give a beige solid (92 g, 47%) which contained 91% of regioisomer 1 and 6% of regioisomer 2.

HPLC 1$^{st}$ regioisomer (91%) Rt=0.33 min; HPLC 2$^{nd}$ regioisomer (6%) Rt=0.52 min. 1H NMR (600 MHz, DMSO-d6): δ 8.34-8.37 (dd, 1H) 7.73-7.76 (t, 1H)

b) 6-Amino-2-bromo-3-fluorobenzoic Acid 2-bromo-3-fluoro-6-nitrobenzoic acid (87 g, 0.3 mol, 91% regioisomer 1) was dissolved in THF (870 ml) and successively degassed and purged with nitrogen (5×). Then, the yellow solution was treated with 10% palladium on carbon (26 g). The black mixture was purged, then backfilled with hydrogen gas and allowed to stir under hydrogen atmosphere at rt for 16 h. The reaction mixture was filtered through hyflo and the pad was rinsed with THF (2×). The collected filtrates were evaporated in vacuo to afford a beige solid (76 g) which was suspended in diethyl ether (300 ml) and stirred for 1 h at 0° C. The suspension was filtered and the solid was dried in vacuo to give 60 g (85%) of 6-Amino-2-bromo-3-fluorobenzoic acid as a single isomer.

HPLC (100%) Rt=0.47 min; ESIMS: 234, 236 [(M+H)$^+$] 1H NMR (600 MHz, DMSO-d6): δ 7.14-7.17 (t, 1H) 6.74-6.77 (dd, 1H)

c) (2S,4S)-tert-Butyl 2-(5-bromo-6-fluoro-4-oxo-3-phenyl-3,4-dihydroquinazolin-2-yl)-4-((tert-butyldimethylsilyl)oxy)pyrrolidine-1-carboxylate A dry solution of a mixture of 6-amino-2-bromo-3-fluorobenzoic acid (63 g, 242 mmol) and (2S,4S)-1-(tert-butoxycarbonyl)-4-((tert-butyldimethylsilyl)oxy)pyrrolidine-2-carboxylic acid (CAS registry 401564-17-8) (120 g, 70% content, 243 mmol) in pyridine (370 ml) was treated with triphenylphosphite (CAS registry 101-02-0) (159 ml, 606 mmol). The light brown solution was stirred at 80° C. for 4 h and then aniline (CAS registry 62-53-3) (26.5 ml, 291 mmol) was added dropwise. After stirring the reaction mixture for another 1 h at 80° C., the pyridine was removed under reduced pressure and then the residue was diluted with EtOAc, washed with 1N NaOH (2×1 L) and brine. The organic phases were dried over $Na_2SO_4$ and concentrated under reduced pressure. The crude product was purified by chromatography on silica gel (0 to 15% EtOAc/heptane) to provide the title compound as a yellow foam (53 g, 35% yield, >90% purity) which was used without further purification for the next step.

HPLC Rt=1.57 min; ESIMS: 618, 620 [(M+H)$^+$].

d) (2S,4S)-tert-Butyl 4-((tert-butyldimethylsilyl)oxy)-2-(6-fluoro-5-(2-methoxypyrimidin-5-yl)-4-oxo-3-phenyl-3,4-dihydroquinazolin-2-yl)pyrrolidine-1-carboxylate To a solution of (2S,4S)-tert-butyl 2-(5-bromo-6-fluoro-4-oxo-3-phenyl-3,4-dihydroquinazolin-2-yl)-4-((tert-butyldimethylsilyl)oxy)pyrrolidine-1-carboxylate (53 g, 86 mmol, >90% content) in NMP (600 ml) was added (2-methoxypyridin-5-yl)boronic acid (CAS registry 628692-15-9) (19.8 g, 129 mmol), Palladium(II)-acetate (CAS registry 3375-31-3) (1.92 g, 8.6 mmol), sodium carbonate (27.2 g, 257 mmol) and X-Phos (CAS registry 564483-18-7) (8.17 g, 17.1 mmol). The reaction mixture was heated to 140° C. and stirred for 1 h. After cooling to ambient temperature, the mixture was partitioned between ethyl acetate (1 L) and water (1 L). The water phase was extracted with ethyl acetate (1 L) and the combined organic phases were washed with brine (1 L), dried over sodium sulfate and evaporated. The crude product was purified by chromatography on silica gel (0 to 40% ethyl acetate/hexane) to provide a yellow foam (37 g) which was dissolved again in DCM (300 ml) and treated with PL-TMT MP resin (0.66 mmol/g) for 18 h. After filtration and evaporation in vacuo the title compound was obtained as white foam (35 g, 63% yield).

HPLC Rt=1.52 min; ESIMS: 648 [(M+H)+].

e) 6-Fluoro-2-((2S,4S)-4-hydroxypyrrolidin-2-yl)-5-(2-methoxypyrimidin-5-yl)-3-phenylquinazolin-4(3H)-one At rt, a solution of (2S,4S)-tert-butyl 4-((tert-butyldimethylsilyl)oxy)-2-(6-fluoro-5-(2-methoxypyrimidin-5-yl)-4-oxo-3-phenyl-3,4-dihydroquinazolin-2-yl)pyrrolidine-1-carboxylate (35 g, 54 mmol) in THF (400 ml) was treated with aq. $H_3PO_4$ soln. (600 ml, 85 wt %). The mixture was stirred for 3 h at rt. Water was added and the mixture was basified with a sat. aq. $Na_2CO_3$ soln. to pH~10. The mixture was extracted with EtOAc (2×5 L) and DCM (2×5 L), then the combined organic layers were dried over $Na_2SO_4$ and concentrated in vacuo to afford a pale yellow solid (22.3 g, 90% yield) which was used without further purification for the next step.

HPLC Rt=0.60 min; ESIMS: 434 [(M+H)$^+$].

f) 2-Amino-4-((2S,4S)-2-(6-fluoro-5-(2-methoxypyrimidin-5-yl)-4-oxo-3-phenyl-3,4-dihydroquinazolin-2-yl)-4-hydroxypyrrolidin-1-yl)-6-methylpyrimidine-5-carbonitrile A solution of 6-fluoro-2-((2S,4S)-4-hydroxypyrrolidin-2-yl)-5-(2-methoxypyrimidin-5-yl)-3-phenylquinazolin-4 (3H)-one (22 g, 50.8 mmol) and 2-amino-4-chloro-6-methylpyrimidine-5-carbonitrile (CAS registry 99586-66-0) (9 g, 50.8 mmol) in EtOH (600 ml) was treated with DIPEA (17.7 ml, 102 mmol) and was irradiated at 120° C. for 60 min in a mw. The reaction mixture was evaporated under reduced pressure. The oil was taken up in DCM and washed with sat. aq. $NaHCO_3$ soln., the organic layer was dried over $Na_2SO_4$ and concentrated in vacuo. The crude product was purified by chromatography on silica gel (10 to 100% ethyl acetate/hexane) to provide 18 g (63% yield) of the title compound as a colorless solid.

HPLC Rt=0.85 min; ESIMS: 566 [(M+H)$^+$].

$^1$H NMR (600 MHz, DMSO-d$_6$) δ 8.55 (br. s, 2H), 7.83-7.78 (m, 2H), 7.73 (dd, 1H), 7.58-7.52 (m, 2H), 7.52-7.48 (t, 1H), 7.41 (d, 1H), 7.05 (br. s, 1H), 6.65 (br. s., 1H), 5.32 (br. s., 1H), 4.61 (br. s., 1H), 4.18 (m, 2H), 3.93 (s, 3H), 3.73 (br. s, 1H), 2.29 (s, 3H), 2.04 (br. s, 1H), 1.91-1.85 (m, 1H).

Crystallization of Example 7

21 g of amorphous Example 7 were weighted out into a round bottom flask and stirred at 300 rpm in 400 mL of purified water for 7 days. The water was filtered off and the collected solids were dried under vacuum at 60° C. until constant weight. The resulting material was seen to be crystalline as per X-ray powder diffraction analysis, with a melting onset temperature at 178.1° C. as measured by differential scanning calorimetry at 10° C./min (sample size 2.2.mg). The crystalline form of Example 7 was found to contain 10.7% (W/W) of water as determined by elemental analysis and is likely a tri-hydrat.

List of most significant 2-Theta peaks from X-ray Powder Diffraction Pattern with tolerances ±0.1 of the crystalline form of Example 7:

TABLE 1

| Compounds prepared according to Scheme 1 (aryl cross coupling in second step) ||
|---|---|
| Degrees 2-Theta (±0.1) | Intensity |
| 7.589 | Low |
| 10.224 | Low |
| 10.867 | Medium |
| 11.227 | Low |
| 12.353 | Low |
| 14.612 | Medium |
| 15.226 | Medium |
| 15.571 | Low |
| 18.156 | Low |
| 20.628 | Medium |
| 24.244 | High |
| 24.776 | Medium |

Scheme 1:

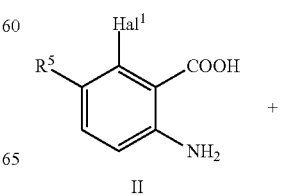

II

-continued

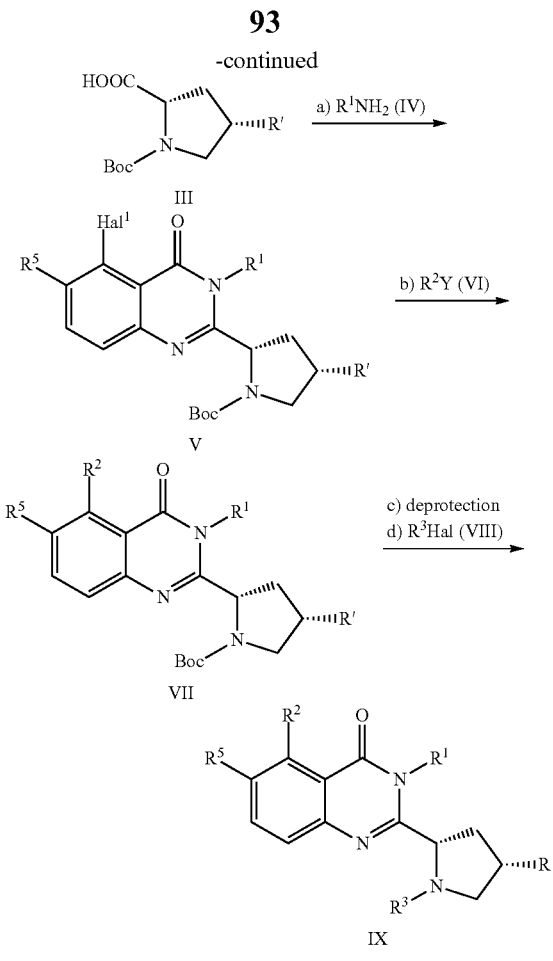

$R^1$, $R^2$, $R^3$, $R^5$ are as defined above for a compound of formula (I), $Hal^1$ is a halogen, such as a bromide or a chloride, R is H or $R^7$ as defined above for a compound of formula (I); R' is R or a substituent that can be transferred into R via one or more functionalization steps or functional group adjustment step.

a) At rt, a dry solution of anthranilic acid derivative II (1 eq.) and of enantiomerically pure cyclic amino acid derivative III (1 eq.) in pyridine (0.83 M) was treated with triphenylphosphite (2.5 eq.) and the reaction mixture was stirred at 70° C. for 2 to 18 h, then treated with an amino compound IV. The reaction mixture was stirred at 70 to 80° C. for 2 to 18 h.

b1) Stille Coupling

Under argon atmosphere, a solution of chloro or bromo intermediate V (1 eq.) in DMF (0.07 to 0.1 M) was treated with heteroaryl tributylstannane VI (1.1 to 1.5 eq.) and bis(tri-t-butylphosphine) palladium (0) (0.1 eq.). The tube was sealed and the reaction mixture was stirred at 80° C. to 100° C. for 3 h to 4 d.

Or b2) Suzuki Coupling

A solution of chloro or bromo intermediate V (1 eq.), heteroaryl boronic acid VI (2 eq.), Pd(OAc)$_2$ (0.2 eq.)/BrettPhos (0.6 eq.) or BrettPhos Palladacycle (CAS registry 1148148-01-9) (0.2 eq.) and Na$_2$CO$_3$ (3 eq.) in NMP (0.094 M) was degassed and backfilled with argon (3×). The reaction mixture was irradiated in a mw at 150° C. to 160° C. for 1 to 3 h under normal absorption with reload of catalyst and ligand if necessary.

c) At rt, a dry solution of protected intermediate VII (1 eq.) in THF or DCM (0.1 to 0.6 M) was treated with TFA (10 eq.), aq. H$_3$PO$_4$ soln. (85 wt %) or with aq. H$_3$PO$_4$ soln. followed by TFA and the reaction mixture was stirred at rt for 1 h to 5 d.

d) At rt, a solution of deprotected intermediate (1 eq.) and an aryl halogenide VIII (1 to 2.5 eq.) in alcohol (nBuOH or EtOH, 0.08M to 0.1M) was treated with DIPEA (2 to 5 eq.) and irradiated in a microwave reactor or heated in an oil bath at 120-160° C. for 0.5 h to 6 d. Purification of intermediates and final products IX was carried out by flash chromatography, HPLC or SFC.

TABLE 2

Compounds prepared according to Scheme 2 (aryl cross coupling in third step)

| Example | Compound | HPLC Rt [min] | MS [m/z; (M + 1)$^+$] |
|---|---|---|---|
| 2 | (S)-4-Amino-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile<br>Precursors: IA1, IB1, IC1, ID1, IE1<br>Conditions: CB1, CD1 | 0.93 | 490 |
| 3 | (S)-4-Amino-6-(2-(5-(2-methoxypyrimidin-5-yl)-4-oxo-3-phenyl-3,4-dihydroquinazolin-2-yl)pyrrolidin-1-yl)pyrimidine-5-carbonitrile<br>Precursors: IA1, IB1, IC1, ID1, IE6<br>Conditions: CB1, CD2 | 0.98 | 518 |

TABLE 2-continued

Compounds prepared according to Scheme 2
(aryl cross coupling in third step)

| Example | Compound | HPLC Rt [min] | MS [m/z; (M + 1)+] |
|---|---|---|---|
| 4 | (S)-2-Amino-4-(2-(5-(2-methoxypyrimidin-5-yl)-4-oxo-3-phenyl-3,4-dihydroquinazolin-2-yl)pyrrolidin-1-yl)-6-methylpyrimidine-5-carbonitrile<br>Precursors: IA1, IB1, IC1, ID2, IE6<br>Conditions: CB1, CD2 | 1.00 | 532 |
| 5 | (S)-4-Amino-6-(2-(6-fluoro-5-(1-methyl-1H-pyrazol-4-yl)-4-oxo-3-phenyl-3,4-dihydroquinazolin-2-yl)pyrrolidin-1-yl)pyrimidine-5-carbonitrile<br>Precursors: IA1, IB3, IC1, ID1, IE1<br>Conditions: CB1, CD1 | 0.93 | 508 |
| 6 | (S)-2-Amino-4-(2-(6-fluoro-5-(1-methyl-1H-pyrazol-4-yl)-4-oxo-3-phenyl-3,4-dihydroquinazolin-2-yl)pyrrolidin-1-yl)-6-methylpyrimidine-5-carbonitrile<br>Precursors: IA1, IB3, IC1, ID2, IE1<br>Conditions: CB1, CD1 | 0.96 | 522 |
| 7 | 2-Amino-4-((2S,4S)-2-(6-fluoro-5-(2-methoxypyrimidin-5-yl)-4-oxo-3-phenyl-3,4-dihydroquinazolin-2-yl)-4-hydroxypyrrolidin-1-yl)-6-methylpyrimidine-5-carbonitrile<br>Precursors: IA2, IB3, IC1, ID2, IE6<br>Conditions: CB2, CD2 | 0.87 | 566 |

TABLE 2-continued

Compounds prepared according to Scheme 2
(aryl cross coupling in third step)

| Example | Compound | HPLC Rt [min] | MS [m/z; (M + 1)+] |
|---|---|---|---|
| 8 | 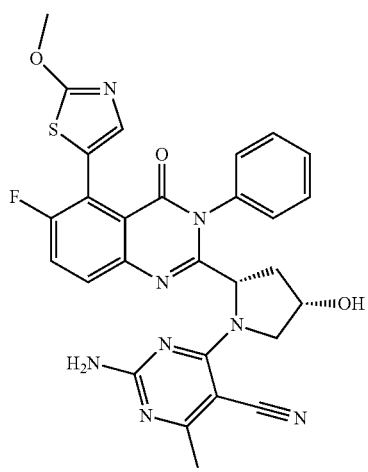 [SMILES: COc1ncc(-c2c(F)ccc3nc([C@@H]4C[C@H](O)CN4c4nc(N)nc(C)c4C#N)n(-c4ccccc4)c(=O)c23)s1]　4-Amino-6-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)pyrimidine-5-carbonitrile<br>Precursors: IA2, IB3, IC1, ID1, IE1<br>Conditions: CB2, CD1 | 0.78 | 524 |
| 10 | 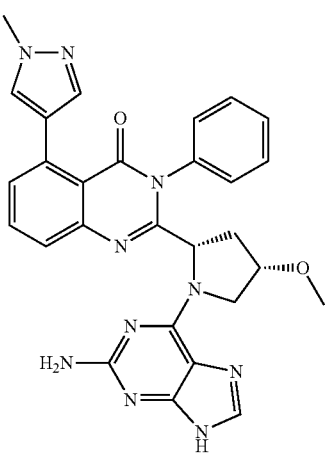　2-Amino-4-((2S,4S)-4-methoxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile<br>Precursors: IA4, IB2, IC1, ID2, IE1<br>Conditions: CB1, CD1 | 0.91 | 534 |
| 9 | 2-Amino-4-((2S,4S)-2-(6-fluoro-5-(2-methoxythiazol-5-yl)-4-oxo-3-phenyl-3,4-dihydroquinazolin-2-yl)-4-hydroxypyrrolidin-1-yl)-6-methylpyrimidine-5-carbonitrile<br>Precursors: IA2, IB3, IC1, ID2, IE4<br>Conditions: CB2, CD1 | 0.93 | 571 |
| 11 | 2-((2S,4S)-1-(2-Amino-9H-purin-6-yl)-4-methoxypyrrolidin-2-yl)-5-(1-methyl-1H-pyrazol-4-yl)-3-phenylquinazolin-4(3H)-one<br>Precursors: IA4, IB2, IC1, ID3, IE1<br>Conditions: CB1, CD1 | 0.72 | 535 |

TABLE 2-continued

Compounds prepared according to Scheme 2
(aryl cross coupling in third step)

| Example | Compound | HPLC Rt [min] | MS [m/z; (M + 1)+] |
|---|---|---|---|
| 12 | 2-Amino-4-((2S,4S)-4-methoxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile<br>Precursors: IA4, IB2, IC1, ID2, IE6<br>Conditions: CB1, CD2 | 0.97 | 562 |

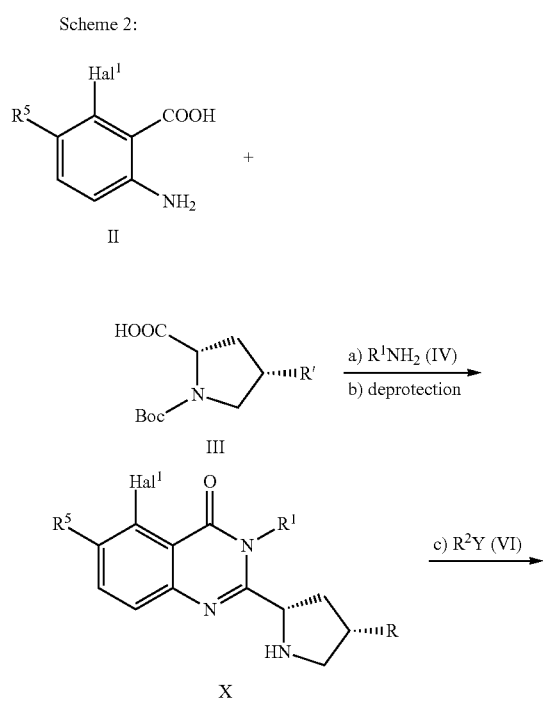

Scheme 2:

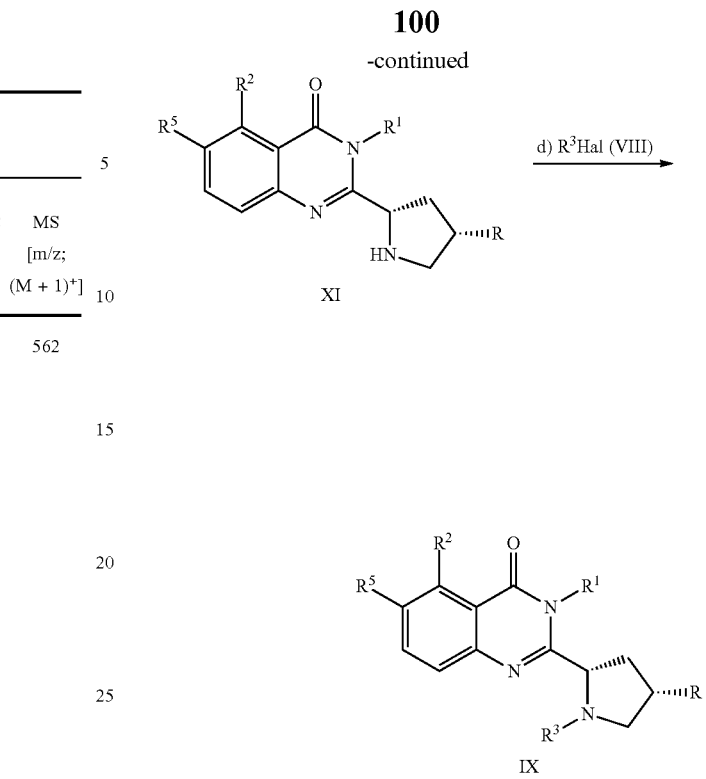

$R^1$, $R^2$, $R^3$, $R^5$ are as defined above for a compound of formula (I), $Hal^1$ is a halogen, such as a bromide or a chloride, R is H or $R^7$ as defined above for a compound of formula (I); R' is R or a substituent that can be transferred into R via one or more functionalization steps or functional group adjustment step.

a) At rt, a dry solution of anthranilic acid derivative II (1 eq.) and of enantiomerically pure cyclic amino acid derivative III (1 eq.) in pyridine (0.83 M) was treated with triphenylphosphite (2.5 eq.) and the reaction mixture was stirred at 70° C. for 2 to 18 h, then treated with an amino compound IV. The reaction mixture was stirred at 70 to 80° C. for 2 to 18 h.

b) At rt, a dry solution of protected intermediate (1 eq.) in THF or DCM (0.1 to 0.6 M) was treated with TFA (10 eq.), aq. $H_3PO_4$ soln. (85 wt %) or with aq. $H_3PO_4$ soln. followed by TFA and the reaction mixture was stirred at rt for 1 h to 5 d.

c) Stille Coupling

Under argon atmosphere, a solution of chloro or bromo intermediate X (1 eq.) in DMF (0.07 to 0.1 M) was treated with heteroaryl tributylstannane VI (1.1 to 1.5 eq.) and bis(tri-t-butylphosphine) palladium (0) (0.1 eq.). The tube was sealed and the reaction mixture was stirred at 80° C. to 100° C. for 3 h to 4 d.

d) At rt, a solution of intermediate XI (1 eq.) and an aryl halogenide VIII (1 to 2.5 eq.) in alcohol (nBuOH or EtOH, 0.08M to 0.1M) was treated with DIPEA (2 to 5 eq.) and irradiated in a microwave reactor or heated in an oil bath at 120-160° C. for 0.5 h to 6 d.

Purification of intermediates and final products IX was carried out by flash chromatography, HPLC or SFC.

TABLE 3

Compounds prepared according to Scheme 3
(aryl coupling in fourth step)

| Example | Compound | HPLC Rt [min] | MS [m/z; (M + 1)+] |
|---|---|---|---|
| 13 | (S)-2-Amino-4-methyl-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile<br>Precursors: IA1, IB1, IC1, ID2, IE1<br>Conditions: CB1, CD1 | 0.96 | 504 |
| 14 | (S)-4-Amino-6-(2-(5-(1-methyl-1H-pyrazol-4-yl)-4-oxo-3-(otolyl)-3,4-dihydroquinazolin-2-yl)pyrrolidin-1-yl)pyrimidine-5-carbonitrile<br>Precursors: IA1, IB1, IC2, ID1, IE1<br>Conditions: CB1, CD1<br>1:1 Mixture of diastereomeric atropisomers | 0.97, 0.99 | 504 |

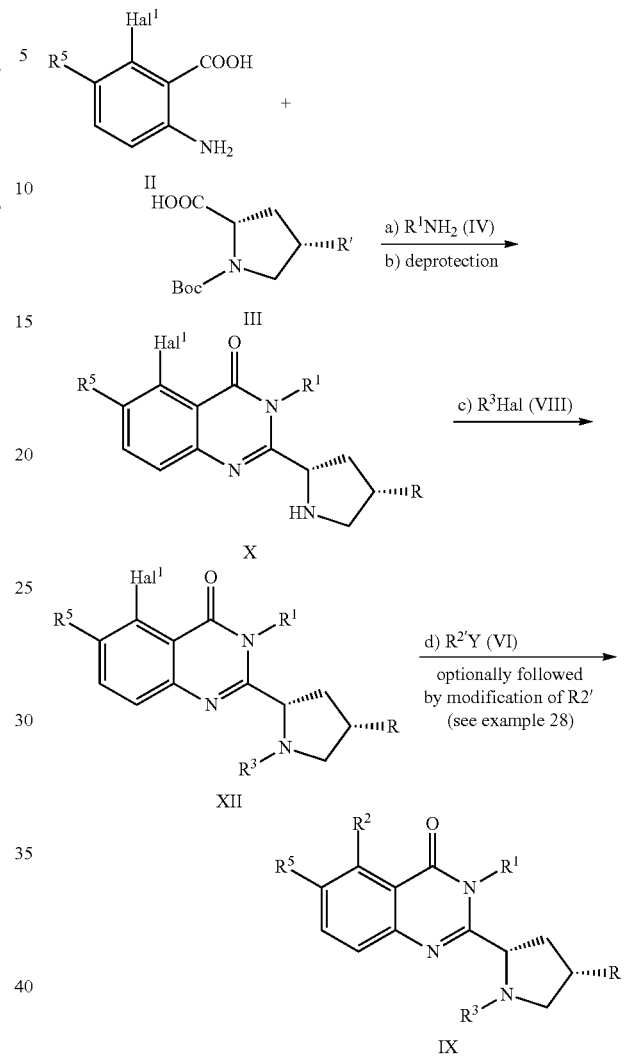

Scheme 3

$R^1$, $R^2$, $R^3$, $R^5$ are as defined above for a compound of formula (I), $Hal^1$ is a halogen, such as a bromide or a chloride, R is H or $R^7$ as defined above for a compound of formula (I); R' is R or a substituent that can be transferred into R via one or more functionalization steps or functional group adjustment step.

a) At rt, a dry solution of anthranilic acid derivative II (1 eq.) and of enantiomerically pure cyclic amino acid derivative III (1 eq.) in pyridine (0.83 M) was treated with triphenylphosphite (2.5 eq.) and the reaction mixture was stirred at 70° C. for 2 to 18 h, then treated with an amino compound IV. The reaction mixture was stirred at 70 to 80° C. for 2 to 18 h.

b) At rt, a dry solution of the protected intermediate (1 eq.) in THF or DCM (0.1 to 0.6 M) was treated with TFA (10 eq.), aq. $H_3PO_4$ soln. (85 wt %) or with aq. $H_3PO_4$ soln. followed by TFA and the reaction mixture was stirred at rt for 1 h to 5 d.

c) At rt, a solution of deprotected intermediate X (1 eq.) and an aryl halogenide VIII (1 to 2.5 eq.) in alcohol (nBuOH or EtOH, 0.08M to 0.1M) was treated with DIPEA (2 to 5 eq.) and irradiated in a microwave reactor or heated in an oil bath at 120-160° C. for 0.5 h to 6 d.

d1) Stille Coupling

Under argon atmosphere, a solution of chloro or bromo intermediate XII (1 eq.) in DMF (0.07 to 0.1 M) was treated with a heteroaryl tributylstannane VI (1.1 to 1.5 eq.) and bis(tri-t-butylphosphine) palladium (0) (0.1 eq.). The tube was sealed and the reaction mixture was stirred at 80° C. to 100° C. for 3 h to 4 d.

Or d2) Suzuki Coupling

A solution of chloro or bromo intermediate XII (1 eq.), a heteroaryl boronic acid or a heteroaryl boronate ester VI (1.2-2 eq.), Pd(OAc)$_2$ (0.2 eq.)/BrettPhos (0.6 eq.), BrettPhos Palladacycle (CAS registry 1148148-01-9) (0.2 eq.) or PdCl$_2$(PPh$_3$)$_2$ (0.07 eq.) and Na$_2$CO$_3$ (2.4-3 eq.) in NMP (0.094 M) or acetonitrile (0.125 M) was degassed and backfilled with argon (3×). The reaction mixture was irradiated in a mw at 150° C. to 160° C. for 5 min to 3 h with reload of catalyst and ligand if necessary.

Or d3) Sonogashira Coupling

A solution of bromo intermediate XII (1 eq.), an alkyne VI (3 eq.), Pd(Ph$_3$)$_4$ (0.05 eq.), CuI (0.1 eq.) and Et$_3$N (3 eq.) in DMF (0.1 M) in a closed vial was heated at 100° C. for 18 h. The same amounts of Pd(Ph$_3$)$_4$, CuI and alkyne were reloaded to complete the conversion and the reaction mixture was stirred for another 4 d at 100° C.

Any functional groups present in R$^{2'}$, may be further functionalized in additional steps as described in individual examples shown below.

Purification of intermediates and final products IX was carried out by flash chromatography, HPLC or SFC.

| Example | Compound | HPLC Rt [min] | MS [m/z; (M + 1)$^+$] |
|---|---|---|---|
| 15 | (S)-4-Amino-6-(2-(5-(1-methyl-1H-imidazol-4-yl)-4-oxo-3-phenyl-3,4-dihydroquinazolin-2-yl)pyrrolidin-1-yl)pyrimidine-5-carbonitrile<br>Precursors: IA1, IB1, IC1, ID1, IE2<br>Conditions: CB1, CD1 | 0.70 | 490 |
| 16 | 2-Amino-4-((2S,4S)-4-hydroxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile<br>Precursors: IA2, IB1, IC1, ID2, IE1<br>Conditions: CB2, CD1 | 0.79 | 520 |
| 17 | (S)-2-Amino-4-methyl-6-(2-(4-oxo-3-phenyl-5-(pyrimidin-5-yl)-3,4-dihydroquinazolin-2-yl)pyrrolidin-1-yl)pyrimidine-5-carbonitrile<br>Precursors: IA1, IB2, IC1, ID2, IE7<br>Conditions: CB1, CD2 | 0.91 | 502 |

-continued

| Example | Compound | HPLC Rt [min] | MS [m/z; (M + 1)+] |
|---|---|---|---|
| 18 | 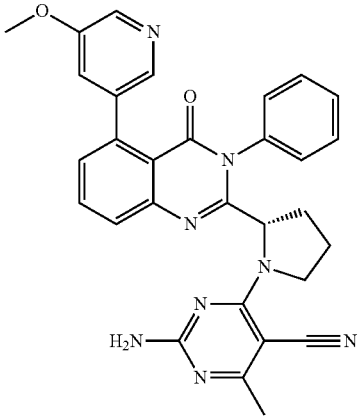 [SMILES: COc1cncc(-c2cccc3nc([C@@H]4CCCN4c4nc(N)nc(C)c4C#N)n(-c4ccccc4)c(=O)c23)c1](S)-2-Amino-4-(2-(5-(5-methoxypyridin-3-yl)-4-oxo-3-phenyl-3,4-dihydroquinazolin-2-yl)pyrrolidin-1-yl)-6-methylpyrimidine-5-carbonitrile<br>Precursors: IA1, IB2, IC1, ID2, IE8<br>Conditions: CB1, CD2 | 1.11 | 531 |
| 19 | 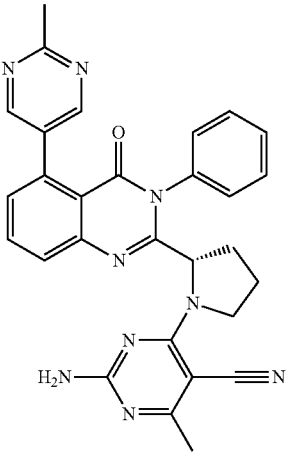 [SMILES: Cc1ncc(-c2cccc3nc([C@@H]4CCCN4c4nc(N)nc(C)c4C#N)n(-c4ccccc4)c(=O)c23)cn1](S)-2-Amino-4-methyl-6-(2-(5-(2-methylpyrimidin-5-yl)-4-oxo-3-phenyl-3,4-dihydroquinazolin-2-yl)pyrrolidin-1-yl)pyrimidine-5-carbonitrile<br>Precursors: IA1, IB2, IC1, ID2, IE9<br>Conditions: CB1, CD2 | 0.94 | 516 |
| 20 | 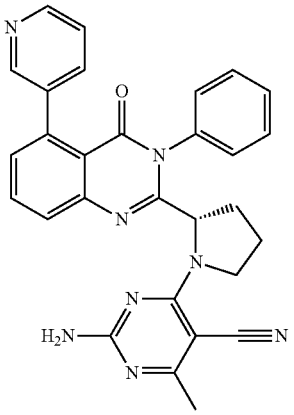(S)-2-Amino-4-methyl-6-(2-(4-oxo-3-phenyl-5-(pyridin-3-yl)-3,4-dihydroquinazolin-2-yl)pyrrolidin-1-yl)pyrimidine-5-carbonitrile<br>Precursors: IA1, IB2, IC1, ID2, IE10<br>Conditions: CB1, CD2 | 0.90 | 501 |
| 21 | 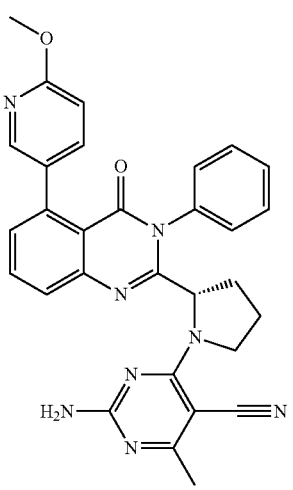 [SMILES: COc1ccc(-c2cccc3nc([C@@H]4CCCN4c4nc(N)nc(C)c4C#N)n(-c4ccccc4)c(=O)c23)cn1](S)-2-Amino-4-(2-(5-(6-methoxypyridin-3-yl)-4-oxo-3-phenyl-3,4-dihydroquinazolin-2-yl)pyrrolidin-1-yl)-6-methylpyrimidine-5-carbonitrile<br>Precursors: IA1, IB2, IC1, ID2, IE11<br>Conditions: CB1, CD2 | 1.11 | 531 |

| Example | Compound | HPLC Rt [min] | MS [m/z; (M + 1)+] |
|---|---|---|---|
| 22 | 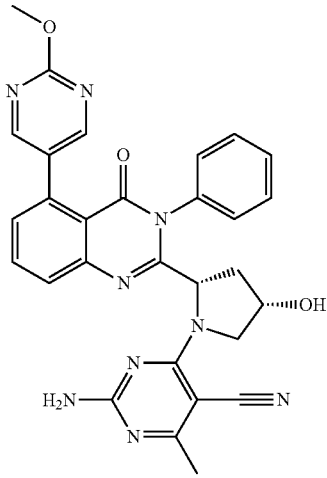 [SMILES: COc1ncc(-c2cccc3nc([C@@H]4C[C@H](O)CN4c4nc(N)nc(C)c4C#N)n(-c4ccccc4)c(=O)c23)cn1] 2-Amino-4-((2S,4S)-4-hydroxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile<br>Precursors: IA2, IB2, IC1, ID2, IE6<br>Conditions: CB3 followed by CB1, CD2 | 0.84 | 548 |
| 23 | 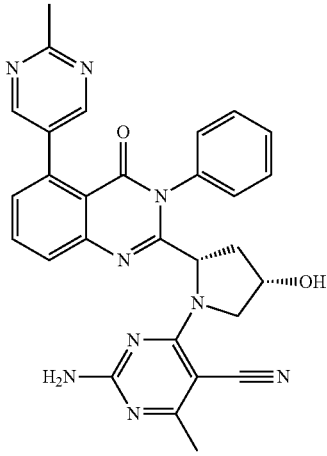 [SMILES: Cc1ncc(-c2cccc3nc([C@@H]4C[C@H](O)CN4c4nc(N)nc(C)c4C#N)n(-c4ccccc4)c(=O)c23)cn1] 2-Amino-4-((2S,4S)-4-hydroxy-2-(5-(2-methylpyrimidin-5-yl)-4-oxo-3-phenyl-3,4-dihydroquinazolin-2-yl)pyrrolidin-1-yl)-6-methylpyrimidine-5-carbonitrile<br>Precursors: IA2, IB2, IC1, ID2, IE9<br>Conditions: CB3 followed by CB1, CD2 | 0.77 | 532 |
| 24 | 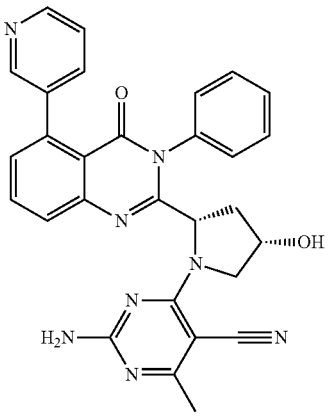 [SMILES: Cc1nc(N)nc(N2C[C@@H](O)C[C@H]2c2nc3cccc(-c4cccnc4)c3c(=O)n2-c2ccccc2)c1C#N] 2-Amino-4-((2S,4S)-4-hydroxy-2-(4-oxo-3-phenyl-5-(pyridin-3-yl)-3,4-dihydroquinazolin-2-yl)pyrrolidin-1-yl)-6-methylpyrimidine-5-carbonitrile<br>Precursors: IA2, IB2, IC1, ID2, IE10<br>Conditions: CB3 followed by CB1, CD2 | 0.72 | 517 |
| 25 | 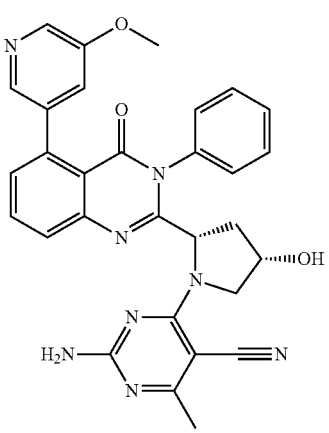 [SMILES: COc1cncc(-c2cccc3nc([C@@H]4C[C@H](O)CN4c4nc(N)nc(C)c4C#N)n(-c4ccccc4)c(=O)c23)c1] 2-Amino-4-((2S,4S)-4-hydroxy-2-(5-(5-methoxypyridin-3-yl)-4-oxo-3-phenyl-3,4-dihydroquinazolin-2-yl)pyrrolidin-1-yl)-6-methylpyrimidine-5-carbonitrile<br>Precursors: IA2, IB2, IC1, ID2, IE8<br>Conditions: CB3 followed by CB1, CD2 | 0.81 | 547 |

| Example | Compound | HPLC Rt [min] | MS [m/z; (M + 1)⁺] |
|---|---|---|---|
| 26 | 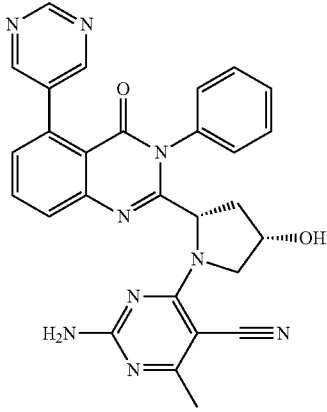<br>2-Amino-4-((2S,4S)-4-hydroxy-2-(4-oxo-3-phenyl-5-(pyrimidin-5-yl)-3,4-dihydroquinazolin-2-yl)pyrrolidin-1-yl)-6-methylpyrimidine-5-carbonitrile<br>Precursors: IA2, IB2, IC1, ID2, IE7<br>Conditions: CB3 followed by CB1, CD2 | 0.75 | 518 |
| 27 | 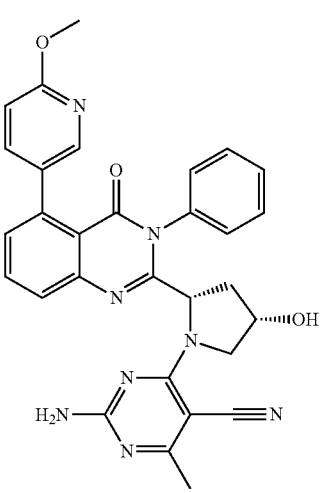 [SMILES: COc1ccc(-c2cccc3nc([C@@H]4C[C@H](O)CN4c4nc(N)nc(C)c4C#N)n(-c4ccccc4)c(=O)c23)cn1]<br>2-Amino-4-((2S,4S)-4-hydroxy-2-(5-(6-methoxypyridin-3-yl)-4-oxo-3-phenyl-3,4-dihydroquinazolin-2-yl)pyrrolidin-1-yl)-6-methylpyrimidine-5-carbonitrile<br>Precursors: IA2, IB2, IC1, ID2, IE11<br>Conditions: CB3, CD2 | 0.94 | 547 |
| 28 | 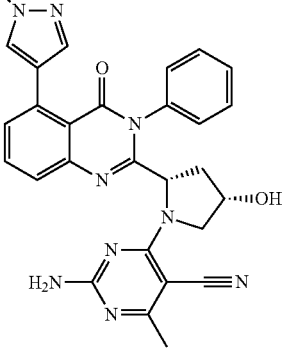<br>2-Amino-4-((2S,4S)-2-(5-(1-(2-hydroxyethyl)-1H-pyrazol-4-yl)-4-oxo-3-phenyl-3,4-dihydroquinazolin-2-yl)pyrrolidin-1-yl)-6-methylpyrimidine-5-carbonitrile<br>Precursors: IA2, IB2, IC1, ID2, IE5<br>Conditions: CB2, CD2<br>Subsequent deprotection using method CE | 0.74 | 550 |
| 29 | 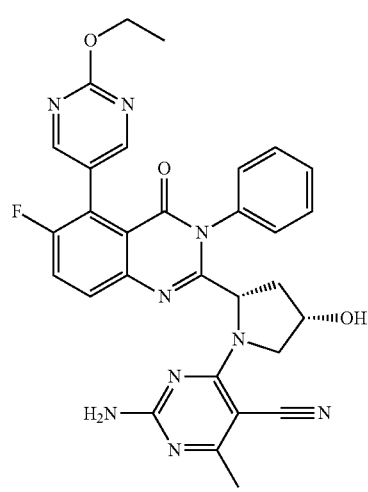 [SMILES: CCOc1ncc(-c2c(F)ccc3nc([C@@H]4C[C@H](O)CN4c4nc(N)nc(C)c4C#N)n(-c4ccccc4)c(=O)c23)cn1]<br>2-Amino-4-((2S,4S)-2-(5-(2-ethoxypyrimidin-5-yl)-6-fluoro-4-oxo-3-phenyl-3,4-dihydroquinazolin-2-yl)-4-hydroxypyrrolidin-1-yl)-6-methylpyrimidine-5-carbonitrile<br>Precursors: IA2, IB3, IC1, ID2, IE3<br>Conditions: CB2, CD1 | 0.94 | 580 |

-continued

| Example | Compound | HPLC Rt [min] | MS [m/z; (M + 1)+] |
|---|---|---|---|
| 30 | 2-Amino-4-((2S,4S)-4-fluoro-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile<br>Precursors: IA3, IB2, IC1, ID2, IE1<br>Conditions: CB2, CD1 | 0.88 | 522 |
| 31 | 2-Amino-4-((2S,4S)-2-(6-fluoro-5-(1-methyl-1H-imidazol-4-yl)-4-oxo-3-phenyl-3,4-dihydroquinazolin-2-yl)-4-hydroxypyrrolidin-1-yl)-6-methylpyrimidine-5-carbonitrile<br>Precursors: IA2, IB3, IC1, ID2, IE2<br>Conditions: CB2, CD1 | 0.60 | 538 |
| 32 | (S)-2-Amino-4-(2-(5-(2-ethoxypyrimidin-5-yl)-4-oxo-3-phenyl-3,4-dihydroquinazolin-2-yl)pyrrolidin-1-yl)-6-methylpyrimidine-5-carbonitrile<br>Precursors: IA1, IB1, IC1, ID2, IE3<br>Conditions: CB1, CD1 | 1.07 | 546 |
| 33 | (S)-4-Amino-6-(2-(5-(3-hydroxyprop-1-yn-1-yl)-4-oxo-3-phenyl-3,4-dihydroquinazolin-2-yl)pyrrolidin-1-yl)pyrimidine-5-carbonitrile<br>Precursors: IA1, IB2, IC1, ID1, IE12<br>Conditions: CB1, CD3 | 0.87 | 464 |

General Procedures Used for Preparation of Table Examples:

CA) Cyclization, Using POPh₃

At rt, a dry solution of amino acid derivative (1 eq.) and anthranilic acid derivative (1 eq.) in pyridine (0.83 M) was treated with triphenylphosphite (2.5 eq.) and the reaction mixture was stirred at 70° C. for 2 to 18 h, then treated with the amino or hydrazine derivative. The reaction mixture was stirred at 70° C. for 2 to 18 h. The reaction mixture was diluted with EtOAc, washed with sat. aq. NaHCO₃ soln. (2×) or sat. aq. CuSO₄ soln. and brine. The organic phase was dried over Na₂SO₄ and concentrated under reduced pressure. The crude product was purified by chromatography on silica gel (heptane/EtOAc)

CB) Deprotection Conditions
CB1) Using TFA
At rt, a dry solution of Boc intermediate (1 eq.) in DCM (0.1 to 0.25 M) was treated with TFA (10 eq.) and the reaction mixture was stirred at rt for 1 to 18 h. The reaction mixture was basified with a sat. aq. NaHCO$_3$ soln. to pH~9. The mixture was extracted with DCM (2×), then the combined organic layers were dried over Na$_2$SO$_4$ and concentrated in vacuo.
CB2) Using H$_3$PO$_4$
At rt, a dry solution of amino acid derivative (1 eq.) in THF (0.2 to 0.6 M) was treated with aq. H$_3$PO$_4$ soln. (85 wt % purchased from Aldrich) (same volume than solvent). The reaction mixture was stirred at rt for 24 h to 6 d. Water was added and the mixture was basified with a sat. aq. NaHCO$_3$ soln. to pH~9. The mixture was extracted with EtOAc (2×) and DCM (2×), then the combined organic layers were dried over Na$_2$SO$_4$ and concentrated in vacuo.
CB3) Using H$_3$PO$_4$ and TFA
At rt, a dry solution of amino acid derivative (1 eq.) in THF (0.085 M) was treated with aq. H$_3$PO$_4$ soln. (85 wt % purchased from Aldrich) (10 eq.). The reaction mixture was stirred at rt for 24 h then TFA (13 eq.) and DCM (0.042 M) were added and the reaction mixture was stirred at rt for 3 d. Basic work-up was done, and after concentration of the organic layer, the residue was diluted with DCM (0.14 M) and treated again with TFA (13 eq.), and stirred at rt for 18 h. The reaction mixture was basified with a sat. aq. NaHCO$_3$ soln. to pH~9. The mixture was extracted with DCM (2×), then the combined organic layers were dried over Na$_2$SO$_4$ and concentrated in vacuo.
CC) Coupling of R$^3$ Moiety
At rt, a solution of deprotected intermediate (1 eq.) and an aryl halogenide (1 to 2.5 eq.) in alcohol (nBuOH or EtOH, 0.08 M to 0.1 M) was treated with DIPEA (2 to 5 eq.) and heated in a microwave reactor or oil bath at 120-160° C. for 0.5 h to 6 d. The reaction mixture was evaporated under reduced pressure. The residue was taken up in DCM and washed with sat. aq. NaHCO$_3$ soln., the organic layer was dried over Na$_2$SO$_4$ and concentrated in vacuo. The crude was purified over either flash chromatography, SFC or prep. RP-HPLC.
CD) Coupling of R$^2$ Moiety
CD1) Using Intermediate IE1)-IE4)
Under argon atmosphere, a solution of chloro or bromo intermediate (1 eq.) in DMF (0.07 to 0.1 M) was treated with IE (1.1 to 1.5 eq.) and bis(tri-t-butylphosphine) palladium (0) (0.1 eq.). The tube was sealed and the reaction mixture was stirred at 80° C. to 100° C. for 3 h to 4 d. The reaction mixture was diluted with EtOAc and washed with water, the organic layer was dried over Na$_2$SO$_4$ and concentrated in vacuo. The crude was purified over either flash chromatography, SFC or prep. RP-HPLC.
CD2) Using Intermediates IE5)-IE11)
For IE5): A solution of chloro or bromo intermediate (1 eq.) in acetonitrile (0.125 M) was treated with IE5) (1.2 eq.) followed by a 1 M aq. Na$_2$CO$_3$ soln. (2.4 eq.) and PdCl$_2$(PPh$_3$)$_2$ (0.07 eq.). The reaction mixture was heated in a mw oven at 150° C. for 5 min under normal absorption. The reaction mixture was diluted with EtOAc and washed with water, the organic layer was dried over Na$_2$SO$_4$ and concentrated in vacuo. The crude was purified over either flash chromatography, SFC or prep. RP-HPLC.
For IE6)-IE11): A solution of chloro or bromo intermediate (1 eq.), IE (2 eq.), Pd(OAc)$_2$ (0.2 eq.)/BrettPhos (0.6 eq.) or BrettPhos Palladacycle (CAS registry 1148148-01-9) (0.2 eq.), Na$_2$CO$_3$ (3 eq.) in NMP (0.094 M) was degassed and backfilled with argon (3×). The reaction mixture was irradiated in a mw at 150° C. to 160° C. for 1 to 3 h under normal absorption with reload of catalyst and ligand if necessary. The reaction mixture was diluted with EtOAc and washed with water, the organic layer was dried over Na$_2$SO$_4$ and concentrated in vacuo. The crude was purified over either flash chromatography, SFC or prep. RP-HPLC.
CD3) Using Intermediate IE12)
A solution of bromo intermediate (1 eq.), IE12 (3 eq.), Pd(Ph$_3$)$_4$ (0.05 eq.), CuI (0.1 eq.), Et$_3$N (3 eq.) in DMF (0.1 M) in a closed vial was heated at 100° C. for 18 h. The same amounts of Pd(Ph$_3$)$_4$, CuI and IE12 were reloaded to complete the conversion and the reaction mixture was stirred for another 4 d at 100° C. The reaction mixture was diluted with EtOAc and washed with water, the organic layer was dried over Na$_2$SO$_4$ and concentrated in vacuo. The crude was purified over either flash chromatography, SFC or prep. RP-HPLC.
CE) Deacylation for Example 28
A solution of the corresponding acetyl derivative (1 eq.) in dry MeOH (0.1 M) was treated with K$_2$CO$_3$ (3 eq.). The suspension was stirred for 2 h at rt. It was evaporated under reduced pressure and the residue was taken up in EtOAc and washed with aq. 1N HCl soln., the organic layer was dried over Na$_2$SO$_4$ and concentrated in vacuo. The crude was purified over SFC.
Intermediates for Table Examples
IA) Amino Acid Derivatives

| Intermediate # | Structure | Name | CAS # or comment on synthesis |
|---|---|---|---|
| IA1 | HOOC-pyrrolidine-Boc | (S)-1-(tert-Butoxycarbonyl)pyrrolidine-2-carboxylic acid | 15761-39-4 |
| IA2 | HOOC-pyrrolidine(OTBDMS)-Boc | (2S,4S)-1-(tert-Butoxycarbonyl)-4-((tert-butyldimethylsilyl)oxy)pyrrolidine-2-carboxylic acid | 401564-17-8 |
| IA3 | HOOC-pyrrolidine(F)-Boc | (2S,4S)-1-(tert-Butoxycarbonyl)-4-fluoropyrrolidine-2-carboxylic acid | 203866-13-1 |
| IA4 | HOOC-pyrrolidine(OMe)-Boc | (2S,4S)-1-(tert-Butoxycarbonyl)-4-methoxypyrrolidine-2-carboxylic acid | 83623-93-2 |

IB) Anthranilic Acid Derivatives

| Intermediate # | Structure | Name | CAS # or comment on synthesis |
|---|---|---|---|
| IB1 | Cl-C$_6$H$_3$(NH$_2$)-COOH | 2-Amino-6-chlorobenzoic acid | 2148-56-3 |

-continued

| Intermediate # | Structure | Name | CAS # or comment on synthesis |
|---|---|---|---|
| IB2 | [2-Amino-6-bromobenzoic acid structure] | 2-Amino-6-bromobenzoic acid | 20776-48-1 |
| IB3 | [6-Amino-2-bromo-3-fluorobenzoic acid structure] | 6-Amino-2-bromo-3-fluorobenzoic acid | 2 steps from CAS 132715-69-6 (see Example 1) |

IC) Amines or Hydrazines

| Intermediate # | Structure | Name | CAS # or comment on synthesis |
|---|---|---|---|
| IC1 | [Aniline structure] | Aniline | 62-53-3 |
| IC2 | [o-Toluidine structure] | o-Toluidine | 95-53-4 |

ID) $R^3$ Precursors

| Intermediate # | Structure | Name | CAS # or comment on synthesis |
|---|---|---|---|
| ID1 | [4-Amino-6-chloropyrimidine-5-carbonitrile structure] | 4-Amino-6-chloropyrimidine-5-carbonitrile | 60025-09-4 |
| ID2 | [2-Amino-4-chloro-6-methylpyrimdine-5-carbonitrile structure] | 2-Amino-4-chloro-6-methylpyrimdine-5-carbonitrile | 99586-66-0 |
| ID3 | [6-Bromo-7H-purin-2-amine structure] | 6-Bromo-7H-purin-2-amine | 82499-03-4 |

IE) $R^2$ Precursors

| Intermediate # | Structure | Name | CAS # or comment on synthesis |
|---|---|---|---|
| IE1 | [1-Methyl-4-(tributylstannyl)-1H-pyrazole structure] | 1-Methyl-4-(tributylstannyl)-1H-pyrazole | 179055-21-1 |
| IE2 | [1-Methyl-4-(tributylstannyl)-1H-imidazole structure] | 1-Methyl-4-(tributylstannyl)-1H-imidazole | 446285-73-0 |

-continued

| Intermediate # | Structure | Name | CAS # or comment on synthesis |
|---|---|---|---|
| IE3 | 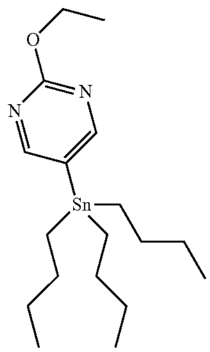 [SMILES: CCC[CH2][Sn]([CH2]CCC)([CH2]CCC)[c]1cnc(OCC)nc1] | 2-Ethoxy-5-(tributylstannyl)pyrimidine | 1025746-10-4 |
| IE4 | 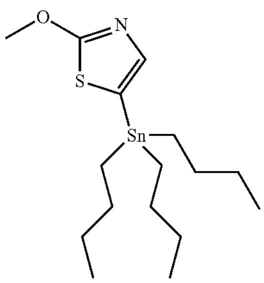 [SMILES: CCC[CH2][Sn]([CH2]CCC)([CH2]CCC)[c]1cnc(OC)s1] | 2-Methoxy-5-(tributylstannyl)thiazole | 1025744-42-6 |
| IE5 | 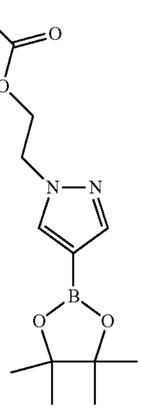 | 2-(4-(4,4,5,5-Tetramethyl-1,3,2-dioxaborolan-2-yl)-1H-pyrazol-1-yl)ethyl acetate | 1251731-71-1 |
| IE6 | 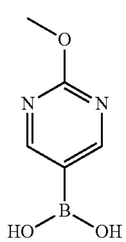 | (2-Methoxypyrimidin-5-yl)boronic acid | 628692-15-9 |
| IE7 | 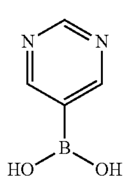 | Pyrimidin-5-ylboronic acid | 109299-78-7 |

| Intermediate # | Structure | Name | CAS # or comment on synthesis |
|---|---|---|---|
| IE8 | 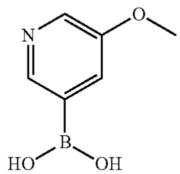 | (5-Methoxypyridin-3-yl)boronic acid | 850991-69-4 |
| IE9 | 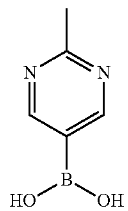 | (2-Methylpyrimidin-5-yl)boronic acid | 1034924-06-5 |
| IE10 | 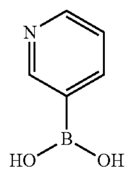 | Pyridin-3-ylboronic acid | 1692-25-7 |
| IE11 | 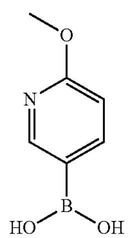 | (6-Methoxypyridin-3-yl)boronic acid | 163105-89-3 |
| IE12 | 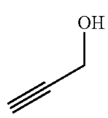 | Prop-2-yn-1-ol | 107-19-7 |

Biological Evaluation

The activity of a compound according to the present invention can be assessed by the following in vitro & in vivo methods.

Biological Assays

1 Determination of Enzymatic PI3K Alpha, PI3Kbeta, PI3Kgamma and PI3K Delta Isoform Inhibition 1.1 Generation of Gene Constructs, Protein Expression and Purification For the enzymatic assays, the preparation of PI3K gene constructs, protein expression and purification for HTS are described in WO2012/004299.

1.2 Biochemical Assays for PI3Kalpha, PI3Kbeta (Kinase-Glo Format)

The efficacy of the compounds of examples 1-117 as PI3 kinase inhibitors can be demonstrated as follows:

The kinase reaction is performed in a final volume of 50 µl per well of a half area COSTAR, 96 well plate. The final concentrations of ATP and phosphatidyl inositol in the assay are 5 µM and 6 µg/mL, respectively. The reaction is started by the addition of PI3 kinase, e.g. PI3 kinase α. p110δ.

The components of the assay are added per well as follows:

10 µl test compound in 5% DMSO per well in columns 2-1.

Total activity is determined by addition 10 µl of 5% vol/vol DMSO in the first 4 wells of column 1 and the last 4 wells of column 12.

The background is determined by addition of 10 µM control compound to the last 4 wells of column 1 and the first 4 wells of column 12.

2 mL 'Assay mix' are prepared per plate:
  1.912 mL of HEPES assay buffer
  8.33 µl of 3 mM stock of ATP giving a final concentration of 5 µM per well
  1 µl of [$^{33}$P]ATP on the activity date giving 0.05 µCi per well
  30 µl of 1 mg/mL PI stock giving a final concentration of 6 µg/mL per well
  5 µl of 1 M stock $MgCl_2$ giving a final concentration of 1 mM per well 20 µl of the assay mix are added per well.

2 mL 'Enzyme mix' are prepared per plate (x* µl PI3 kinase p110α in 2 mL of kinase buffer). The 'Enzyme mix' is kept on ice during addition to the assay plates.

* The volume of enzyme is dependent on the enzymatic activity of the batch in use.

20 µl 'Enzyme mix' are added/well to start the reaction.
The plate is then incubated at room temperature for 90 minutes.
The reaction is terminated by the addition of 50 µl WGA-SPA bead (wheat germ agglutinin-coated Scintillation Proximity Assay beads) suspension per well.
The assay plate is sealed using TopSeal-S (heat seal for polystyrene microplates, PerkinElmer LAS [Deutschland] GmbH, Rodgau, Germany) and incubated at room temperature for at least 60 minutes.
The assay plate is then centrifuged at 1500 rpm for 2 minutes using the Jouan bench top centrifuge (Jouan Inc., Nantes, France).
The assay plate is counted using a Packard TopCount, each well being counted for 20 seconds.

In a more preferred assay, the kinase reaction is performed in a final volume of 10 µl per well of a low volume non-binding CORNING, 384 well black plate (Cat. No. #3676). The final concentrations of ATP and phosphatidyl inositol (PI) in the assay are 1 µM and 10 µg/mL, respectively. The reaction is started by the addition of ATP.

The components of the assay are added per well as follows:
50 nl test compounds in 90% DMSO per well, in columns 1-20, 8 concentrations (1/3 and 1/3.33 serial dilution step) in single.
Low control: 50 nl of 90% DMSO in half the wells of columns 23-24 (0.45% in final).
High control: 50 nl of reference compound (e.g. compound of Example 7 in WO 2006/122806) in the other half of columns 23-24 (2.5 µM in final).
Standard: 50 nl of reference compound as just mentioned diluted as the test compounds in columns 21-22.
20 mL 'buffer' are prepared per assay:
  200 µl of 1M TRIS HCl pH7.5 (10 mM in final)
  60 µl of 1M $MgCl_2$ (3 mM in final)
  500 µl of 2M NaCl (50 mM in final)
  100 µl of 10% CHAPS (0.05% in final)
  200 µl of 100 mM DTT (1 mM in final)
  18.94 mL of nanopure water
10 mL 'PI' are prepared per assay:
  200 µl of 1 mg/mL I-alpha-Phosphatidylinositol (Liver Bovine, Avanti Polar Lipids Cat. No. 840042C MW=909.12) prepared in 3% OctylGlucoside (10 µg/mL in final)
  9.8 mL of 'buffer'
10 mL 'ATP' are prepared per assay:
  6.7 µl of 3 mM stock of ATP giving a final concentration of 1 µM per well
  10 mL of 'buffer'
2.5 mL of each PI3K construct are prepared per assay in 'PI' with the following final concentration:
  10 nM PI3K alfa EMV B1075
  25 nM beta EMV BV949
5 µl of 'PI/PI3K' are added per well.
5 µl 'ATP' are added per well to start the reaction.
The plates are then incubated at room temperature for 60 minutes (alfa, beta, delta) or 120 minutes (gamma).
The reaction is terminated by the addition of 10 µl Kinase-Glo (Promega Cat. No. #6714).
The assay plates are read after 10 minutes in Synergy 2 reader (BioTek, Vermont USA) with an integration time of 100 milliseconds and sensitivity set to 191.
Output: The High control is around 60,000 counts and the Low control is 30,000 or lower
This luminescence assay gives a useful Z' ratio between 0.4 and 0.7

The Z' value is a universal measurement of the robustness of an assay. A Z' between 0.5 and 1.0 is considered an excellent assay.

1.3 Biochemical Assays for PI3Kdelta, PI3Kgamma (Adapta Format)

The TR-FRET Adapta™ Universal Kinase Assay Kit was purchased from Invitrogen Corporation (Carlsbad/CA, USA) (Cat. No. PV5099). The kit contains the following reagents: Adapta Eu-anti-ADP Antibody (Europium labeled anti-ADP antibody in HEPES buffered saline, Cat. No. PV5097), Alexa Fluor® 647-labeled ADP tracer (Alexa Fluor® 647-labeled ADP tracer in HEPES buffered saline, Cat. No. PV5098), proprietary TR-FRET dilution buffer pH 7.5 (Cat. No. PV3574).

PIK3CD substrate Phosphatidylinositol was obtained from Invitrogen (vesicles consisting of 2 mM PI in 50 mM HEPES pH7.5; Cat. No. PV5371). PIK3CG substrate Phosphatidylinositol-4,5-bisphosphate (PIP(4,5)2 was obtained from Invitrogen (PIP2:PS large unilamellar vesicles consisting of 1 mM PI P2: 19 mM PS in 50 mM HEPES pH7.5, 3 mM MgCl2, 1 mM EGTA; Cat. No. PV5100).

Time-Resolved Fluorescence Resonance Energy Transfer (TR-FRET) is a technology based on energy transfer between two adjacent dyes, from an excited electron in one dye (the donor) to an electron of an adjacent dye (the acceptor) through resonance, then released as a photon. This energy transfer is detected by an increase in the fluorescence emission of the acceptor, and a decrease in the fluorescence emission of the donor. TR-FRET assays for protein kinases use a long-lifetime lanthanide Terbium or Europium chelates as the donor species which overcome interference from compound autofluorescence or light scatter from precipitated compounds, by introducing a delay after excitation by a flashlamp excitation source. Results are often expressed as a ratio of the intensities of the acceptor and donor fluorophores. The ratiometric nature of such a value corrects for differences in assay volumes between wells, as well as corrects for quenching effects due to colored compounds. The Adapta™ assay can be divided into two phases: a kinase reaction phase and an ADP detection phase. In the kinase reaction phase, all kinase reaction components are added to the well and the reaction is allowed to incubate for a set period of time specific for each kinase. After the reaction, a detection solution of Eu-labeled anti-ADP antibody, Alexa Fluor® 647-labeled ADP tracer, and EDTA (to stop the kinase reaction) are added to the assay well. ADP formed by the kinase reaction will displace the Alexa Fluor® 647-labeled ADP tracer from the antibody, resulting in a decrease in TR-FRET signal. In the presence of an inhibitor, the amount of ADP formed by the kinase reaction is reduced, and the resulting intact antibody-tracer interaction maintains a high TR-FRET signal. In the Adapta™ assay, the donor (Europium-anti-ADP antibody) is excited at 340 nm and will transfer its energy to the acceptor (Alexa Fluor® 647-labeled ADP tracer). The emission from the Alexa Fluor® 647 can be monitored with a filter centered at 665 nm because it is located between the emission peaks of the donor, which is measured at 615/620 nm.

50 nL of compound dilutions were dispensed onto white 384-well small volume polystyrene plate as described in section 2.2. Then 5 µL of PI3Kgamma and PI3Kdelta and lipid substrate (PI or PIP2:PS) followed by 5 µL of ATP (final assay volume 10 µL) are incubated at RT. The standard reaction buffer for the Adapta™ TR-FRET assay contained 10 mM Tris-HCl pH 7.5, 3 mM MgCl2, 50 mM NaCl, 1 mM DTT, 0.05% CHAPS. Reactions were stopped with 5 µL of a mixture of EDTA containing the Eu-labeled anti-ADP antibody and the Alexa Fluor® 647-labeled ADP tracer in TR-FRET dilution buffer (proprietary to IVG). Plates are read 15 to 60 mins later in a Synergy2 reader using an integration time of 0.4 seconds and a delay of 0.05 seconds. Control for the 100% inhibition of the kinase reaction was performed by replacing the PI3K by the standard reaction buffer. The control for the 0% inhibition was given by the solvent vehicle of the compounds (90% DMSO in $H_2O$).

Data are analyzed using Excel fit software or Graphpad Prism. $EC_{50}$ values were derived by fitting a sigmoidal dose-response curve to a plot of assay readout over inhibitor concentration. All fits were performed with the program XLfit4 (ID Business Solutions, Guildford, UK). Determination of $EC_{50}$ values of the percentage inhibition of each compound at 8 concentrations (usually 10, 3.0, 1.0, 0.3, 0.1, 0.030, 0.010 and 0.003 µM) n=2 were derived by fitting a sigmoidal dose-response curve to a plot of assay readout over inhibitor concentration. All fits were performed with the program XLfit4 (ID Business Solutions, Guildford, UK).

In one embodiment of the present invention, the class I PI3 kinase inhibitor, wherein said inhibitor has an inhibitory action on the PI3K isoform delta, wherein the range of activity, expressed as $IC_{50}$, in the enzymatic PI3K delta assay is between 1 nM and 500 nM.

In another embodiment of the present invention, the class I PI3 kinase inhibitor, wherein said inhibitor has an inhibitory action on the PI3K isoform delta, wherein the range of activity, expressed as $IC_{50}$, in the enzymatic PI3K delta assay is between 1 nM and 100 nM.

In another embodiment of the present invention, the class I PI3 kinase inhibitor, wherein said inhibitor has an inhibitory action on the PI3K isoform delta, wherein the range of activity, expressed as $IC_{50}$, in the enzymatic PI3K delta assay is between 0.5 nM and 10 nM.

In one embodiment of the present invention, the class I PI3 kinase inhibitor, wherein said inhibitor has an inhibitory action on the PI3K isoform gamma, wherein the range of activity, expressed as $IC_{50}$, in the enzymatic PI3K gamma assay is between 1 nM and 500 nM.

In another embodiment of the present invention, the class I PI3 kinase inhibitor, wherein said inhibitor has an inhibitory action on the PI3K isoform gamma, wherein the range of activity, expressed as $IC_{50}$, in the enzymatic PI3K gamma assay is between 1 nM and 100 nM.

In one embodiment of the present invention, the class I PI3 kinase inhibitor, wherein said inhibitor has an inhibitory action on the PI3K isoform delta, wherein the range of activity, expressed as $IC_{50}$, in the cellular PI3K delta assay is between 1 nM and 1000 nM.

In another embodiment of the present invention, the class I PI3 kinase inhibitor, wherein said inhibitor has an inhibitory action on the PI3K isoform delta, wherein the range of activity, expressed as $IC_{50}$, in the cellular PI3K delta assay is between 1 nM and 500 nM.

In one embodiment of the present invention, the class I PI3 kinase inhibitor, wherein said inhibitor has an inhibitory action on the PI3K isoform gamma, wherein the range of activity, expressed as $IC_{50}$, in the cellular PI3K gamma assay is between 1 nM and 1000 nM.

In another embodiment of the present invention, the class I PI3 kinase inhibitor, wherein said inhibitor has an inhibitory action on the PI3K isoform gamma, wherein the range of activity, expressed as $IC_{50}$, in the cellular PI3K delta gamma is between 1 nM and 500 nM.

2. Cellular Assays

In another embodiment of the present invention, the class I PI3 kinase inhibitor shows an at least 10 fold selectivity over the PI3K isoform alpha in a cellular assay.

In another embodiment of the present invention, the class I PI3 kinase inhibitor shows an at least 20 fold selectivity over the PI3K isoform alpha in a cellular assay.

2.1 Phosphoinositide-3 kinase (PI3K)-Mediated Akt 1/2 (S473) Phosphorylation in Rat-1 Cells Rat-1 cells stably overexpressing a myristoylated form of the catalytic subunit of human phosphoinositide-3 kinase (PI3K) alpha, beta or delta were plated in 384-well plates at a density of 7500 (PI3K alpha), 6200 (PI3K beta), or 4000 (PI3K delta) cells in 30 ul complete growth medium (Dulbecco's modified Eagle's medium (DMEM high glucose) supplemented with 10% (v/v) fetal bovine serum, 1% (v/v) MEM non essential amino acids, 10 mM HEPES, 2 mM L-glutamine, 10 µg/mL puromycin and 1% (v/v) Penicillin/Streptomycin) and were incubated at 37% C/5% $CO_2$/95% humidity for 24 h. Compounds were diluted in 384-well compound plates (compound master plates), to obtain 8-point serial dilutions for 40 test compounds in 90% DMSO, as well as 4 reference compounds plus 16 high controls and 16 low (inhibited) controls. Predilution plates were prepared by dispensing pipetting 250 nl of compound solutions into 384-well polypropylen plates (daugther plates), using a Hummingwell nanoliter dispenser. Compounds were prediluted by the addition of 49.75 ul complete growth medium. 10 ul of prediluted compound solution were transferred to the cell plate using a 384-well pipettor, resulting in a final DMSO concentration of 0.11%. Cells were incubated for 1 h at 37% C/5% $CO_2$/95% humidity. The supernatant was removed, the cells were lysed in 20 ul of lysis buffer for AlphaScreen® SureFire® detection.

For detection of p-AKT(Ser473), the SureFire® p-Akt 1/2 (Ser473) Assay Kit (PerkinElmer, U.S.A.) was used. 5 ul of cell lysate was transferred to 384-well low volume Proxiplates for detection using a 384-well pipettor. Addition of AlphaScreen® SureFire® reagents was done according to the manufacturer's protocol. First, 5 ul of reaction buffer plus activation buffer mix containing AlphaScreen® acceptor beads was added, the plate was sealed, and incubated on a plate shaker for 2 hours at room temperature. Second, 2 ul of dilution buffer containing AlphaScreen® donor beads was added, and the plate was incubated on plate shaker as above for a further 2 hours. The plate was read on an AlphaScreen® compatible plate reader, using standard AlphaScreen® settings. Alternatively, p-AKT(Ser473) was detected with the CisBio HTRF Assay Kit: As positive control, 0.9 mM of 1-(3-(trifluoromethyl)-4-(piperazin-1-yl)phenyl)-8-(6-methoxypyridin-3-yl)-3-methyl-1H-imidazo[4,5-c]quinolin-2(3H)-one maleic acid salt in 90% (v/v) DMSO was added to the compound master plate. For compound testing, the cells were seeded at a density of 4000 (Rat-1_PI3Kdelta), 8000 (Rat-1_PI3Kalpha), or 6500 (Rat-1_PI3Kbeta) cells in 30 ul complete growth medium into 384-well plates, with a plastic surface promoting the adhesion of cells and their growth (assay plates) and were grown at 37° C./5% $CO_2$/90% humidity for 24 h. Some 10 ul of the compound predilutions from the daughter plate were then transferred to the cells. After treatment with compound for 1 h, medium was removed and cells were lysed by the addition of 20 ul lysis buffer supplemented with blocking buffer. Detection of p-AKT(Ser473) was performed with the HTRF pAKT (Ser473) assay kit according to the manufacturer's instructions using 16 ul of cell lysate in a total detection volume of 20 ul.

2.2 Determination of Murine B Cell Activation

PI3Kδ has been recognized to modulate B cell function when cells are stimulated through the B cell receptor (BCR) (Okkenhaug et al. Science 297:1031 (2002). For assessing the inhibitory property of compounds on B cell activation, the upregulation of activation markers CD86 and CD69 on murine B cells derived from mouse spleen antibody is measured after stimulation with anti-IgM. CD69 is a well known activation marker for B and T cells (Sancho et al. Trends Immunol. 26:136 (2005). CD86 (also known as B7-2) is primarily expressed on antigen-presenting cells, including B cells. Resting B cells express CD86 at low levels, but upregulate it following stimulation of e.g. the BCR or IL-4 receptor. CD86 on a B cell interacts with CD28 on T cells. This interaction is required for optimal T cell activation and for the generation of an optimal IgG1 response (Carreno et al. Annu Rev Immunol. 20:29 (2002)).

Spleens from Balb/c mice are collected, splenocytes are isolated and washed twice with RPMI containing 10% foetal bovine serum (FBS), 10 mM HEPES, 100 Units/mL penicilline/streptomycine. RPMI supplemented in this way is subsequently referred to as medium. The cells are adjusted to $2.5 \times 10^6$ cells/mL in medium and 200 µl cell suspension ($5 \times 10^6$ cells) are added to the appropriate wells of 96 well plates.

Then the cells are stimulated by adding 50 µl anti-IgM mAb in medium (final concentration: 30 µg/mL). After incubation for 24 hours at 37° C., the cells are stained with the following antibody cocktails: anti-mouse CD86-FITC, anti-mouse CD69-PerCP-Cy5.5, anti-mouse CD19-PerCP for the assessment of B cells, and anti-mouse CD3-FITC, anti-mouse CD69-PE for the assessment of T cells (2 µl of each antibody/well). After one hour at room temperature (rt) in the dark the cells are transferred to 96 Deepwell plates. The cells are washed once with 1 mL PBS containing 2% FBS and after re-suspension in 200 µl the samples are analyzed on a FACS Calibur flow cytometer. Lymphocytes are gated in the FSC/SSC dot plot according to size and granularity and further analyzed for expression of CD19, CD3 and activation markers (CD86, CD69). Data are calculated from dot blots as percentage of cells positively stained for activation markers within the CD19+ or CD3+ population using BD CellQest Software.

For assessing the inhibitory property of compounds, compounds are first dissolved and diluted in DMSO followed by a 1:50 dilution in medium. Splenocytes from Balb/c mice are isolated, re-suspended and transferred to 96 well plates as described above (200 µl/well). The diluted compounds or solvent are added to the plates (25 µl) and incubated at 37° C. for 1 hour. Then the cultures are stimulated with 25 µl anti-IgM mAb/well (final concentration 30 µg/mL) for 24 hours at 37° C. and stained with anti-mouse CD86-FITC and anti-mouse CD19-PerCP (2 µl of each antibody/well). CD86 expression on CD19 positive B cells is quantified by flow cytometry as described above.

2.3 Determination of Rat B Cell Activation

PI3Kδ has been recognized to modulate B cell function when cells are stimulated through the B cell receptor (BCR) (Okkenhaug et al. Science 297:1031 (2002). For assessing the inhibitory property of compounds on B cell activation, the upregulation of activation markers CD86 on rat B cells derived from whole blood is measured after stimulation with anti-IgM and recombinant IL-4. The CD86 molecule (also known as B7-2) is primarily expressed on antigen-presenting cells, including B cells. Resting B cells express CD86 at low levels, but upregulate it following stimulation of e.g. the BCR or IL-4 receptor. CD86 on a B cell interacts with CD28 on T cells. This interaction is required for optimal T cell activation and for the generation of an optimal IgG1 response (Carreno et al. Annu Rev Immunol. 20:29 (2002)).

Collection of Rat Blood

Whole blood was collected from the abdominal aorta adult male Lewis rats (LEW/HanHsd) oby using a 10 ml syringe with hypodermic needle pre-coated with sodium heparin. Blood was transferred into 50 ml Falcon tubes and the anticoagulant concentration was adjusted to 100 U/ml.

Stimulation of Rat B Cells and Treatment with Specific Inhibitor

For assessment of the in vitro effects of immunosuppressive drugs, heparinized blood was prediluted to 50% with medium. As medium served DMEM high glucose (Animed cat#1-26F01-I) supplemented with 100 U/ml penicillin, 100 mg/ml streptomycin, 2 mM L-glutamin, 50 mg/ml dextran 40 and 5% fetal calf serum (FCS, Fetaclone I, Gibco #10270-106). Then, 190 µl prediluted blood was spiked with 10 µl of pre-diluted test compound in 96 well U-bottomed microtiter plates (Nunc) resulting in a 3-fold serial dilution with a concentration range from 20 to 0.0003 µM. Control wells were pretreated with DMSO to obtain a final concentration of 0.5% DMSO. Cultures were set up in duplicates, mixed well by agitation on a plate shaker (Heidolph Titramax 101; 30 sec, speed 900), pipetting up and down and agitated on the plate shaker again. Cultures were incubated at 37° C., 5% $CO_2$ for 1 hr. Then, 20 µl of polyclonal goat anti-rat IgM Ab (Serotec, cat#302001) and 10 µl of diluted recombinant rIL-4 (Immunotools #340085) were added to obtain final concentrations of 30 µg/ml and 5 ng/ml, respectively. Plates were mixed by agitation on a plate shaker as above and incubated for 24 hrs at 37° C., 5% $CO_2$.

Determination of B Cell Activation by Flow Cytometry

After incubation, 15 µl of a 25 mM EDTA solution was added per well and shaken for 15 min to detach adherent cells. For analysis of surface activation markers, samples were then stained with PE-Cy5-labeled anti-ratCD45RA (BD cat#557015) to allow gating on B cells in FACS analysis. In addition, samples were stained with PE-labeled anti-rat CD86 (BD cat#551396). All staining procedures were performed at rt for 30 min in the dark. After incubation, samples were transferred to 96-deep well V-bottomed microtiter plates (Corning #396096) containing 2 ml/well of BD Lysing Solution (BD #349202). After lysis of erythrocytes samples were washed with 2 ml of CellWASH (BD #349524). Data was acquired on an LSRII or FACScalibur flow cytometer (BD Biosciences) using Cellquest Plus or DIVA (version 6.1.1) software, respectively. Lymphocytes were gated in the FSC/SSC dot blot according to size and granularity and further analyzed for expression of CD45RA and activation markers. Data were calculated from dot blots or histograms as percentage of cells positively stained for activation markers within the CD45RA+ population.

Statistical Evaluation

The percentage inhibition of B cell activation after exposure to drug was calculated by the following formula:

$$\% \text{ Inhibition} = 100 \times \frac{\text{stimulation without drug} - \text{stimulation with drug}}{\text{stimulation without drug} - \text{unstimulated}}$$

ORIGIN 7 software (OriginLab Corporation, Northampton, Mass.) was used for non-linear regression curve fitting. The drug concentration resulting in 50% inhibition ($IC_{50}$) was obtained by fitting the Hill equation to inhibition data.

2.4 Cellular U937 AKT Assay for PI 3-Kinase Gamma

The U937 monocyte cell line is maintained in a basal medium of RPMI 1640 supplemented with 10% heat inactivated FCS, 100 U/ml Penicillin, 100 ug/ml streptomycin and 2 mM L-glutamine (Invitrogen). U937 suspension culture is maintained by seeding cells at a density of 0.125×10⁶ cells per ml in fresh medium every three or four days. Cells are incubated at 37° C., 5% $CO_2$. Three or four days prior to assay, cells are seeded at a density of 0.25×10⁶ cells per ml in a total volume of 40 ml in a T175 culture flask.

Before beginning the cell manipulations described below, the MSD (Meso Scale Discovery) assay plate is blocked by addition of 150 ul/well blocking buffer supplied and incubated with shaking for a minimum of one hour at room temperature. All steps of the assay must be performed quickly, with accurately timed incubation periods and observing temperature controls where indicated.

Cells seeded at 0.25×10⁶/ml 3 or 4 days prior to the assay are aspirated, transferred to a 50 ml Falcon tube, counted and centrifuged for eight minutes at 300 g at room temperature. Supernatant is aspirated, the cell pellet resuspended and washed once in HBSS (Hank's Balanced Salt Solution) by centrifugation for eight minutes at 300 g at room temperature. The cell pellet is resuspended in HBSS to a concentration of 4×10⁶ per ml, and 100 µL of cell suspension added to each well of a flat-bottomed 96-well tissue culture plate. Assay plates are incubated for 1.5 hours at 37° C., 5% $CO_2$ to allow background AKT phosphorylation to reduce before the compound stimulation step.

A 5 mM stock concentration of compound is prepared in 100% DMSO; from this a 1 in 125 dilution is made in HBSS giving a top compound concentration of 40 µM, 0.8% DMSO. Compound titrations are prepared in a fresh flat-bottomed, 96-well plate, by 10-fold serial dilution of 40 uM into HBSS 0.8% DMSO; pipette tips are replaced after each dilution is made. Compound concentrations at this stage are 4-times the final concentration required in the assay plate. Cells are stimulated with compound or HBSS 0.8% DMSO by direct transfer of 50 ul/well from the compound dilution plate. The assay plate containing compound-treated cells is then incubated for 30 minutes at 37° C. A standard plate layout is used for all experiments.

Compound-treated cells, in addition to positive control wells ("max MIP1α"), are stimulated with 50 µL per well of 40 ng/ml MIP1α (R&D Systems catalogue number 270-LD, lyophilized stock reconstituted to 50 µg/ml with PBS 0.1% BSA). Negative control wells ("min HBSS"), are stimulated with 50 µl/well of HBSS in the absence of MIP1α. Final compound concentrations are now diluted 4-fold giving a top concentration of 10 µM; where added, the final concentration of MIP1α is 10 ng/ml. Cells are incubated with MIP1α for 3 minutes, at 37° C., 5% CO2. After the three minute stimulation period, the assay plate is kept ice cold at all times. Assay plates are centrifuged for 2 minutes at 300 g, 4° C. and supernatant is removed by gently inverting, and then blotting the plate on tissue. Cells are then washed by gentle addition of 150 µL/well of ice cold HBSS and centrifugation at 300 g, for 5 minutes at 4° C. Supernatant is aspirated and the plate blotted as described above. The plate is placed on ice and cells are immediately treated with 35 µL per well of ice cold lysis buffer, prepared according to the kit instructions (per assay plate, to 5 ml of Tris lysis buffer add 100 µl of 50× protease inhibitor solution and 50 µl of each 100× phosphatase inhibitor solutions I and II). Plates are incubated on ice for 20 minutes before centrifugation at 841 g for 5 minutes, 4° C. Block buffer is aspirated from the MSD plate, and the plate washed four times with 300 µl/well Tris wash buffer. 25 µL of cell lysate is then transferred from the assay plate to the washed MSD plate which is sealed and incubated at room temperature for one hour with shaking. The plate is washed four times with 300 µL per well of Tris wash buffer before addition of 25 µL per well of sulfo-tag anti-total AKT/pAKT detection antibody (60 µl of 50× antibody stock is diluted in 1 ml block buffer mixed with 2 ml wash buffer) and incubated at room temperature for one hour with shaking. The plate is washed four times with 300 µl per well of Tris wash buffer and 150 µl per well of Read buffer is added, taking care to avoid the introduction of bubbles. The plate is immediately read using an MSD SECTOR Imager 6000.

Results are exported in Excel and the percentage of phosphorylated AKT is calculated using the equation: % Phosphoprotein=((2*Phospho signal)/(Phospho signal+Total signal))*100. Compound-mediated inhibition of AKT phosphorylation is analysed using Prizm V Graphpad software.

2.5 Determination of TLR9-Induced IL-6 in Mouse Splenocytes

Preparation of Single Cell Suspension from Mouse Spleen

Spleens were dissected from C57BL/6 mice immediately following euthanasia. Excess fat was trimmed from the spleens prior to mashing the spleen through a 0.4 µM cell strainer using a plunger from a 5 ml syringe. A single cell suspension was prepared and the volume was adjusted to 15 ml in a 50 ml Falcon tube using cold PBS. Cells were centrifuged at 1500 rpm for 5 minutes at 4° C. degrees prior to removal of supernatant and re-suspension in 5 ml of red blood cell lysis buffer per spleen and incubation for 5 minutes at room temperature. Ice cold PBS (30 ml) was added to the cells prior to centrifugation at 1500 rpm for 5 minutes at 4° C. The supernatant was removed and the cells were washed twice with 40 ml of murine splenocyte culture media (MSCM). MSCM consisted of RPMI supplemented with 100 units/ml Penicillin and 100 µg/ml Streptomycin, 1× nonessential amino acids, 1 mM Sodium Pyruvate, 0.05 mM β-mercaptoethanol, and 10% heatinactivated Fetal Bovine Serum (FBS). Cells were re-suspended in 10-20 ml of MSCM and counted using a Countess cell counter. Approximately 60×10⁶ splenocytes were obtained from a single C57BL/6 mouse spleen.

Stimulation of Murine Splenocytes and Treatment with Specific Inhibitor

Splenocytes were plated at a final density of 2×10⁵ cells/well in a volume of 100 µl in 96 well flat bottomed plates and incubated in a humidified 37° C. incubator for 2-4 hours. Afterwards, compounds to be tested were dispensed using an automated liquid handling machine using previously prepared compound stock plates. Stock plates consisted of compounds (in 90%/10% DMSO/dd$H_2$0) arrayed in 8-10 point using 2- or 3-fold dilutions. The liquid handling machine dispensed 1 µl of each dilution from the previously prepared compound source plate into the appropriate destination well in the 96-well plate. The final starting concentration of the compounds in the cell culture was 10 µM. The final concentration of DMSO in the cell cultures was 0.5%. Cells were incubated with compounds for 1 hour prior to addition of TLR ligand. Then, a 10×$EC_{80}$ concentration of CpG1826 was added in a volume of 20 µl (for a final culture volume of 200 µl) whereupon cultures were incubated overnight in a humidified 37° C. incubator.

Determination of Interleukin-6 by ELISA

After overnight culture, plates were centrifugated at 2000 rpm for 5 minutes at room temperature. Subsequently 150 µl of each culture was transferred to 96-well V-bottomed plates and IL-6 levels were measured using commercially available mouse IL-6 sandwich ELISA kit. Briefly, plates were coated overnight with the capture antibody prior to blocking for 1 hour with PBS/0.1% BSA. Samples and standards were added in a volume of 50 µl and the plate was incubated for 2 hours at room temperature. After removal of the standards/samples, the plate was washed using PBS/0.05% Tween prior to addition of 50 µl of the biotinylated detection antibody whereupon the plate was incubated for 2 hours at room temperature with agitation. Plates were washed again prior to addition of 50 µl streptavidin-horseradish peroxidase per well for 20 minutes. Following additional plate washes 50 µl TMB substrate was added to each well and plates were incubated for 20 minutes prior addition of 25 µl/well stop solution. IL-6 levels were measured using a SpectraMax 190 Plate Reader (450 nm) and analyzed using SoftMax Pro and GraphPad Prism software.

2.6 Determination of TLR9-Induced IFNalpha in Human Peripheral Blood Mononuclear Cells (PBMC)

Preparation of PBMC from Fresh Human Blood

Human blood (ca. 75 ml) was collected in 10 S-Monovette tubes containing Heparin (S-Monovette 7.5 mL NH Heparin 16 IU/mL blood; Starstedt). Leucosep™ tubes (30 mL #227290; Greiner Bio-one) were prepared by addition of 15 ml lymphocyte separation medium LSM1077™ per tube (#J15-004; PAA Laboratories) and centrifugation for 30 sec at 1000 g. Some 25 ml blood was transferred to Leucosep™ tubes following dilution with equal parts of PBS (without Ca2+/Mg2+; #14190-094). Samples were centrifuged at 800 g for 20 min at 22° C. using an Eppendorf 5810R centrifuge without brake. The PBMC layer was carefully removed from plasma:separation medium interface and transferred into clean 50 ml tube. Cells were washed once by addition of PBS (up to 45 ml) and centrifuged (1400 rpm, 10 min at 22° C.) with brake (set at speed 9) using an Eppendorf 5810R. Pelleted cells were carefully resuspended in Media (RPMI 1640+GlutaMAX-I, 0.05 mM 2-mercaptoethanol, 10 mM HEPES and 5% v/v FCS) and samples pooled. The medium components 2-mercaptoethanol (#31350-010; 50 mM), Hepes (#15630-056, 1M) and RPMI 1640 (1×)+GlutaMAX-I (#61870-010) were obtained from Gibco. FCS (#2-01F36-1) was obtained from Amimed. The PBMC were counted using a Countess® Automated cell counter (sample was pre-diluted 1:10 in Media, prior to the addition of equal volume (10 µl) of Trypan Blue). Cells were diluted to $4 \times 10^6$ cells/ml and seeded in 384-well plates (#353962; Becton Dickinson AG) to give a final volume of 25 µl (i.e. $1 \times 10^5$ cells/well).

Stimulation of PBMC and Treatment with Specific Inhibitor

Compounds were pre-diluted in 100% v/v DMSO (#41640-100 mL; Sigma-Aldrich), followed by transfer in Media (to achieve a final DMSO concentration of 0.25%). Cells were treated with appropriate compound dilution (5 µl) or vehicle control (5 µl) and incubated for 30 min at 37° C. in a humidified incubator in air with 5% (v/v) $CO_2$. Cells were stimulated with CpG2216 (0.3 µM; #tlrl-hodna; Invivogen) or vehicle control (10 µl/well) and incubated for 20 h. Plates were briefly centrifuged (200×g for 2 min at 22° C.) and supernatant samples (30 µl) removed for quantification of IFNα levels.

Quantification of IFNα Using AlphaLisa Technology

For quantification of IFNalpha the human interferon AlphaLISA Kit (#AL264F) from PerkinElmer was used. An antibody mix containing anti-IFNα acceptor beads (5 µg/ml final) and biotinylated antibody anti-IFNα (0.5 nM final) is prepared fresh and dispensed (5 µl) into 384-well Opti-plates™ (#6007299; PerkinElmer). Dilution of known IFNα standards (human IFNα B (2b)) were prepared and together with cell supernatants (5 µl) were added to plates above. Plates were briefly centrifuged (pulse at 200 g), covered with adhesive sealing film, vortexed and incubated 1 h at room temperature in the dark. Streptavidin-coated donor beads (20 µg/ml final) was prepared and added to each well (5 µl) in a dark lit area (light sensitive mix). Plates were incubated 30 min at room temperature (Pates must not be centrifuged or covered). After incubation, the plates were read with an EnVision™ multiplate reader equipped with the ALPHA option using the instrument's own "AlphaScreen standard settings" (e.g. total measurement time: 550 ms, Laser 680 nm excitation time: 180 ms, mirror: D640 as, emission filter: M570w, center wavelength 570 nm, bandwidth 100 nm, transmittance 75%). Data were collected for analysis and quantification of IFNα levels.

Data Evaluation and Analysis

Data were analysed using Excel XL fit 4.0 (Microsoft) with XLfit add-in (IDBS; version 4.3.2). Specific IFNα concentrations were determined following extrapolation to standard curves using human IFNα B (2b). Individual $IC_{50}$ values of compounds were determined by nonlinear regression after fitting of curves to the experimental data.

3 Determination of Antibody Production to Sheep Red Blood Cells (SRBC).

In brief, OFA rats were injected i.v. with sheep erythrocytes on d0 and treated orally on four consecutive days (d0 to d3) with the compounds under investigation. Spleen cell suspensions were prepared on d4 and lymphocytes were plated onto soft agar in presence of indicator cells (SRBC) and complement. Lysis of the indicator cells due to secretion of SRBC-specific antibody (predominantly of the IgM subclass) and presence of complement yielded plaques. The number of plaques per plate were counted and expressed as number of plaques per spleen.

Immunization:

Groups of five female OFA rats were immunized on day 0 with $2 \times 10^8$/ml SRBC (obtained from Laboratory Animal Services LAS, Novartis Pharma AG) in a volume of 0.5 ml per rat by i.v. injection.

Compound Treatment:

Animals were treated with compound suspended in 0.5% CMC, 0.5% Tween80 in for 4 consecutive days (days 0, 1, 2 and 3) starting on the day of immunization. Compound was administered orally twice daily with 12 hours intervals between doses in an application volume of 5 ml/kg body weight.

Preparation of Spleen Cell Suspensions:

On day 4, animals were euthanized with $CO_2$. Spleens were removed, weighed, and deposited in plastic tubes containing 10 ml of cold (4° C.) Hank's balanced salt solution (HBSS; Gibco, pH 7.3, containing 1 mg Phenolred/100 ml) for each rat spleen. Spleens were homogenized with a glass potter, left on ice for 5 minutes and 1 ml supernatant was transferred into a new tube. Cells were washed once in 4 ml HBSS then supernatants were discarded and pellets re-suspended in 1 ml of HBSS. Lymphocyte numbers per spleen were determined by automated cell counter and spleen cell suspensions were adjusted to a cell concentration of $30 \times 10^6$/ml.

Plaque Forming Assay:

Soft agar petri dishes were prepared with 0.7% agarose (SERVA) in HBSS.

In addition, one ml of 0.7% agarose was prepared in plastic tubes and kept at 48° C. in a water bath. Some 50 µl of a $30 \times 10^6$/ml spleen cell suspension and 50 µl of SRBC at 40×10⁸/ml were added, mixed rapidly (Vortex) and poured onto the prepared agarose dishes. Petri dishes were slightly tilted to achieve even distribution of cell mixture on agarose layer. The dishes were left at room temperature for 15 minutes and were then incubated at 37° C. for 60 minutes. Then, 1.4 ml guinea pig complement (Harlan; 10%) was added and the incubation continued for another 60 minutes at 37° C. SRBC-specific antibodies released by the plated-out B cells bound to the antigen (SRBC) in their vicinity. These antigen-antibody complexes activated complement and led to the lysis of the SRBC leaving a bright spot (plaque) within the red erythrocyte layer. Plaques were counted with a microscope.

The following formula for determination of inhibition of plaque formation was used:

% Inhibition=$C*100/V-100$ with: V=mean number of plaques/spleen for vehicle group; C=mean number of plaques/spleen for compound treated group

REFERENCES

N. K. Jerne & A. A. Nordin (1963) Plaque formation in agar by single antibody-producing cells. Science 140:405.
N. K. Jerne, A. A. Nordin & C. Henry (1963) The agar plaque technique for recognizing antibody-producing cells. In: "Cell Bound Antibodies", B. Amos & H. Koprowski, Eds., Wistar Inst. Press, Philadelphia pp. 109-125.

Biological Data
Enzymatic Assay

| Example ID | PI3K alpha IC50 [umol l−1] | PI3K delta IC50 [umol l−1] | PI3K gamma IC50 [umol l−1] |
|---|---|---|---|
| 1 | 0.074 | 0.008 | 0.028 |
| 2 | 1.3 | n.d. | 0.15 |
| 3 | 1.4 | 0.008 | 1.2 |
| 4 | 0.32 | 0.006 | 0.082 |
| 5 | 0.23 | 0.004 | 0.085 |
| 6 | 0.13 | 0.009 | 0.056 |
| 7 | 0.21 | 0.006 | 0.11 |
| 8 | 1.1 | 0.014 | 0.75 |
| 9 | 0.053 | 0.008 | 0.018 |
| 10 | 1.3 | 0.006 | 0.038 |
| 11 | 2.3 | 0.045 | 0.23 |
| 12 | 1.2 | 0.005 | 0.21 |
| 13 | 0.26 | 0.007 | 0.12 |
| 14 | 0.92 | 0.074 | 0.33 |
| 15* | >10 | >10 | >10 |
| 16 | 0.18 | 0.007 | 0.048 |
| 17 | 1.2 | 0.021 | 0.94 |
| 18 | 0.056 | 0.014 | 0.089 |
| 19 | 0.82 | 0.017 | 0.39 |
| 20 | 0.26 | 0.015 | 0.14 |
| 21 | 0.26 | 0.024 | 0.27 |
| 22 | 0.58 | 0.005 | 0.13 |
| 23 | n.d. | n.d. | n.d. |
| 24 | 0.17 | 0.005 | 0.081 |
| 25 | 0.048 | 0.005 | 0.065 |
| 26 | 0.53 | 0.006 | 0.41 |
| 27 | 0.086 | 0.010 | 0.058 |
| 28 | 0.24 | 0.010 | 0.021 |
| 29 | 0.37 | 0.004 | 0.013 |
| 30 | 0.45 | 0.014 | 0.024 |
| 31 | 0.57 | 0.013 | 0.11 |
| 32 | 0.49 | 0.005 | 0.14 |
| 33 | 0.62 | 0.013 | 0.081 |

Cellular Assays

| Example ID | Cell PI3K alpha IC50 [umol l−1] | Cell PI3K delta IC50 [umol l−1] | Cell PI3K gamma IC50 [umol l−1] |
|---|---|---|---|
| 1 | 2.2 | 0.003 | 0.032 |
| 2 | 1.3 | 0.003 | n.d. |
| 3 | 6.8 | 0.011 | 0.43 |
| 4 | 2.8 | <0.003 | 0.040 |
| 5 | 3.0 | 0.007 | 0.22 |
| 6 | 1.4 | 0.005 | 0.041 |
| 7 | 4.7 | 0.009 | 0.025 |
| 8 | 3.2 | 0.006 | 0.029 |
| 9 | 0.67 | <0.003 | 0.056 |
| 10 | 3.9 | 0.060 | 0.038 |
| 11 | >10 | 0.66 | 0.34 |
| 12 | 5.9 | 0.028 | 0.12 |
| 13 | 1.1 | 0.012 | n.d. |
| 14 | 3.3 | 0.008 | 0.21 |
| 15* | >10 | 5.4 | >10 |
| 16 | 2.7 | 0.008 | 0.055 |
| 17 | 5.8 | <0.003 | 0.29 |
| 18 | 0.42 | <0.003 | 0.016 |
| 19 | 5.4 | <0.003 | 0.22 |
| 20 | 1.5 | <0.003 | 0.27 |
| 21 | 2.5 | 0.013 | 1.1 |
| 22 | >10 | 0.007 | 0.018 |
| 23 | >10 | 0.013 | 0.011 |
| 24 | 5.0 | <0.003 | 0.009 |
| 25 | 1.9 | 0.004 | 0.049 |
| 26 | >6.5 | 0.007 | 0.17 |
| 27 | 1.3 | 0.006 | 0.063 |
| 28 | >10 | 0.090 | 0.12 |
| 29 | 2.7 | 0.006 | 0.038 |
| 30 | 2.3 | <0.010 | 0.011 |
| 31 | >10 | 0.12 | 0.24 |
| 32 | 2.4 | <0.003 | 0.72 |
| 33 | 6.5 | 0.014 | 0.12 |

*Biological data for example 15 in the enzymatic and cellular assay are believed to be an artefact.

The invention claimed is:
1. A compound of formula (I)

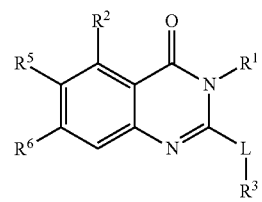

or a pharmaceutically acceptable salt thereof wherein
$R^1$ is
phenyl, which is unsubstituted or substituted by 1, 2 or 3 substituents independently selected from the group consisting of
  methyl, ethyl, difluoromethyl, methoxy, difluoromethoxy, cyclopropyl, chloro and fluoro;
pyridyl, which is unsubstituted or substituted by 1, 2 or 3 substituents independently selected from the group consisting of
  methyl, ethyl, difluoromethyl, methoxy, difluoromethoxy, cyclopropyl, chloro and fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;

pyrolidin-3-yl, which is unsubstituted or substituted in the 1 position by a substituent which is selected from the group consisting of methoxycarbonyl, methylsulfonyl, methyl and methylcarbonyl; or
dimethylamine;
$R^2$ is
$C_4$-$C_7$-heteroaryl, containing one nitrogen atom and additional 0, 1, 2 or 3 heteroatoms independently selected from the group consisting of N, O and S, wherein $C_4$-$C_7$-heteroaryl is unsubstituted or substituted by 1-3 substituents independently selected from the group consisting of
$C_1$-$C_4$-alkyl,
$C_1$-$C_4$-fluoroalkyl,
hydroxy-$C_1$-$C_4$-alkyl,
hydroxy-$C_1$-$C_4$-fluoroalkyl,
$C_1$-$C_4$-alkoxy,
$C_1$-$C_4$-fluoroalkoxy,
$C_3$-$C_6$-cycloalkyl, which is unsubstituted or substituted by 1-3 substituents independently selected from the group consisting of methyl and fluoro,
$C_3$-$C_6$-heterocycloalkyl, which is unsubstituted or substituted by 1-3 substituents independently selected from the group consisting of methyl and fluoro,
cyano,
fluoro,
amino,
$C_1$-$C_4$-alkylamino, and
$C_1$-$C_4$-dialkylamino;
or
$C_2$-$C_5$-alkynyl, which is unsubstituted or substituted by 1-2 substituents independently selected from the group consisting of
$C_1$-$C_4$-fluoroalkyl,
$C_3$-$C_6$-cycloalkyl, which is unsubstituted or substituted by 1-3 substituents independently selected from the group consisting of methyl and fluoro,
$C_3$-$C_6$-heterocycloalkyl, which is unsubstituted or substituted by 1-3 substituents independently selected from the group consisting of methyl and fluoro,
$C_1$-$C_4$-alkoxy,
$C_1$-$C_4$-fluoroalkoxy,
hydroxyl,
cyano,
fluoro,
amino,
$C_1$-$C_4$-alkylamino, and
$C_1$-$C_4$-dialkylamino;
$R^5$ and $R^6$ are independently hydrogen, deuterium or fluoro;
-L-$R^3$ is

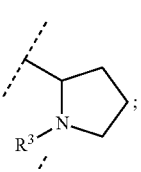 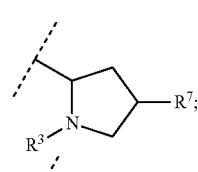

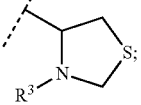 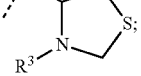

-continued

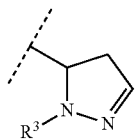

wherein
$R^7$ is methoxy, difluoromethoxy, trifluoromethoxy, hydroxy, fluoro or methylsulfonylamine; and
$R^3$ is

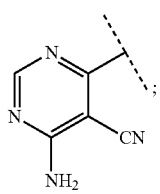 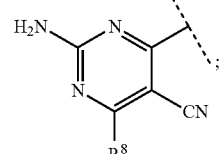

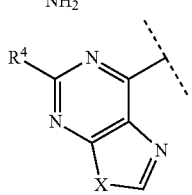 or 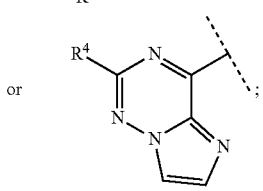

wherein
$R^4$ is hydrogen or amino,
$R^8$ is hydrogen, methyl, fluoromethyl, difluoromethyl, trideuteromethyl or amino, and
X is NH, NMe or S.

2. A compound according to claim 1 or a pharmaceutically acceptable salt thereof, of the formula (I')

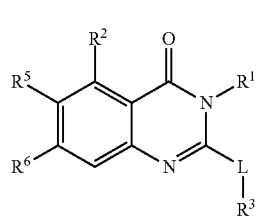

wherein,
$R^1$ is
phenyl, which is unsubstituted or substituted by 1, 2 or 3 substituents independently selected from the group consisting of
methyl, ethyl, difluoromethyl, methoxy, difluoromethoxy, cyclopropyl, chloro and fluoro;
pyridyl, which is unsubstituted or substituted by 1, 2 or 3 substituents independently selected from the group consisting of
methyl, ethyl, difluoromethyl, methoxy, difluoromethoxy, cyclopropyl, chloro and fluoro;
1-methylpyrazol-5-yl;
2-methylthiophen-5-yl;
$C_3$-$C_6$-cycloalkyl, which is unsubstituted or substituted in the 1 position by methyl;
tetrahydropyran-4-yl;
piperidin-1-yl;
morpholin-4-yl;

pyrolidin-3-yl, which is unsubstituted or substituted in the 1 position by a substituent which is selected from the group consisting of methoxycarbonyl, methylsulfonyl, methyl and methylcarbonyl; or dimethylamine;

$R^2$ is $C_4$-$C_7$-heteroaryl, containing one nitrogen atom and additional 0, 1, 2 or 3 heteroatoms independently selected from the group consisting of N, O and S, wherein $C_4$-$C_7$-heteroaryl is unsubstituted or substituted by 1-3 substituents independently selected from the group consisting of $C_1$-$C_4$-alkyl, $C_1$-$C_4$-fluoroalkyl, hydroxy-$C_1$-$C_4$-alkyl, hydroxy-$C_1$-$C_4$-fluoroalkyl, $C_1$-$C_4$-alkoxy, $C_1$-$C_4$-fluoroalkoxy, $C_3$-$C_6$-cycloalkyl, which is unsubstituted or substituted by 1-3 substituents independently selected from the group consisting of methyl and fluoro, $C_3$-$C_6$-heterocycloalkyl, which is unsubstituted or substituted by 1-3 substituents independently selected from the group consisting of methyl and fluoro, cyano, fluoro, amino, $C_1$-$C_4$-alkylamino, and $C_1$-$C_4$-dialkylamino;

$R^5$ and $R^6$ are independently hydrogen, deuterium or fluoro;

-L-$R^3$ is

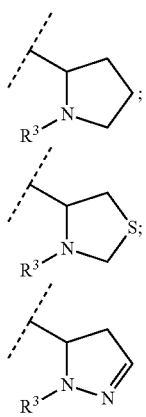

wherein $R^7$ is methoxy, difluoromethoxy, trifluoromethoxy, hydroxy, fluoro or methylsulfonylamine; and $R^3$ is

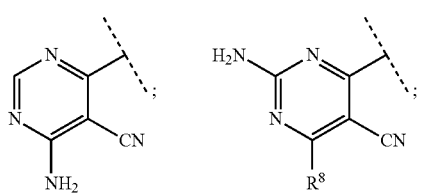

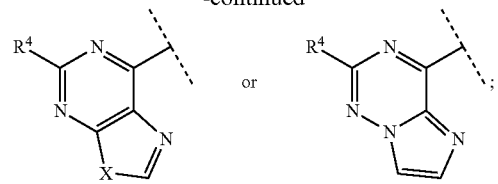

wherein $R^4$ is hydrogen or amino, $R^8$ is hydrogen, methyl, fluoromethyl, difluoromethyl, trideuteromethyl or amino, and X is NH, NMe or S.

3. A compound according to claim 1 or a pharmaceutically acceptable salt thereof, of the formula (Ia)

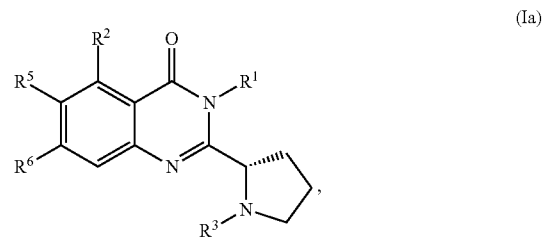

(Ia)

wherein $R^1$ is phenyl, which is unsubstituted or substituted by 1, 2 or 3 substituents independently selected from the group consisting of methyl, ethyl, difluoromethyl, methoxy, difluoromethoxy, cyclopropyl, chloro and fluoro;

pyridyl, which is unsubstituted or substituted by 1, 2 or 3 substituents independently selected from the group consisting of methyl, ethyl, difluoromethyl, methoxy, difluoromethoxy, cyclopropyl, chloro and fluoro;

1-methylpyrazol-5-yl;

2-methylthiophen-5-yl;

$C_3$-$C_6$-cycloalkyl, which is unsubstituted or substituted in the 1 position by methyl;

tetrahydropyran-4-yl;

piperidin-1-yl;

morpholin-4-yl;

pyrolidin-3-yl, which is unsubstituted or substituted in the 1 position by a substituent which is selected from the group consisting of methoxycarbonyl, methylsulfonyl, methyl and methylcarbonyl; or dimethylamine;

$R^2$ is $C_4$-$C_7$-heteroaryl, containing one nitrogen atom and additional 0, 1, 2 or 3 heteroatoms independently selected from the group consisting of N, O and S, wherein $C_4$-$C_7$-heteroaryl is unsubstituted or substituted by 1-3 substituents independently selected from the group consisting of $C_1$-$C_4$-alkyl, $C_1$-$C_4$-fluoroalkyl, hydroxy-$C_1$-$C_4$-alkyl, hydroxy-$C_1$-$C_4$-fluoroalkyl, $C_1$-$C_4$-alkoxy, $C_1$-$C_4$-fluoroalkoxy, $C_3$-$C_6$-cycloalkyl, which is unsubstituted or substituted by 1-3 substituents independently selected from the group consisting of methyl and fluoro, $C_3$-$C_6$-heterocycloalkyl, which is unsubstituted or substituted by 1-3 substituents independently selected from the group consisting of methyl and fluoro, cyano, fluoro, amino, $C_1$-$C_4$-alkylamino, and $C_1$-$C_4$-dialkylamino;

or $C_2$-$C_5$-alkynyl, which is unsubstituted or substituted by 1-2 substituents independently selected from the group consisting of $C_1$-$C_4$-fluoroalkyl, $C_3$-$C_6$-cycloalkyl, which is unsubstituted or substituted by 1-3 substituents independently selected from the group consisting of methyl and fluoro, $C_3$-$C_6$-heterocycloalkyl, which is unsubstituted or substituted by 1-3 substituents independently selected from the group consisting of methyl and fluoro, $C_1$-$C_4$-alkoxy, $C_1$-$C_4$-fluoroalkoxy, hydroxy, cyano, fluoro, amino, $C_1$-$C_4$-alkylamino, and $C_1$-$C_4$-dialkylamino;

$R^5$ and $R^6$ are independently hydrogen, deuterium or fluoro; and $R^3$ is

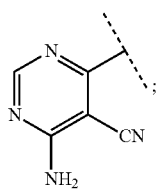 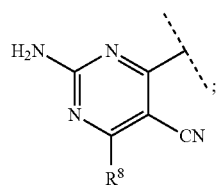

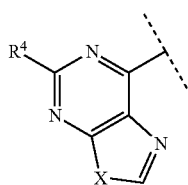 or 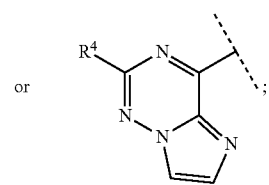

wherein $R^4$ is hydrogen or amino, $R^8$ is hydrogen, methyl, fluoromethyl, difluoromethyl, trideuteromethyl or amino, and X is NH, NMe or S.

4. A compound according to claim 1 or a pharmaceutically acceptable salt thereof, of the formula (Ib)

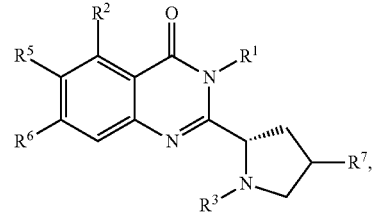

wherein $R^1$ is phenyl, which is unsubstituted or substituted by 1, 2 or 3 substituents independently selected from the group consisting of
  methyl, ethyl, difluoromethyl, methoxy, difluoromethoxy, cyclopropyl, chloro and fluoro;

pyridyl, which is unsubstituted or substituted by 1, 2 or 3 substituents independently selected from the group consisting of
  methyl, ethyl, difluoromethyl, methoxy, difluoromethoxy, cyclopropyl, chloro and fluoro;

1-methylpyrazol-5-yl;

2-methylthiophen-5-yl;

$C_3$-$C_6$-cycloalkyl, which is unsubstituted or substituted in the 1 position by methyl;

tetrahydropyran-4-yl;

piperidin-1-yl;

morpholin-4-yl;

pyrolidin-3-yl, which is unsubstituted or substituted in the 1 position by a substituent which is selected from the group consisting of methoxycarbonyl, methylsulfonyl, methyl and methylcarbonyl; or dimethylamine;

$R^2$ is $C_4$-$C_7$-heteroaryl, containing one nitrogen atom and additional 0, 1, 2 or 3 heteroatoms independently selected from the group consisting of N, O and S, wherein $C_4$-$C_7$-heteroaryl is unsubstituted or substituted by 1-3 substituents independently selected from the group consisting of $C_1$-$C_4$-alkyl, $C_1$-$C_4$-fluoroalkyl, hydroxy-$C_1$-$C_4$-alkyl, hydroxy-$C_1$-$C_4$-fluoroalkyl, $C_1$-$C_4$-alkoxy, $C_1$-$C_4$-fluoroalkoxy, $C_3$-$C_6$-cycloalkyl, which is unsubstituted or substituted by 1-3 substituents independently selected from the group consisting of methyl and fluoro, $C_3$-$C_6$-heterocycloalkyl, which is unsubstituted or substituted by 1-3 substituents independently selected from the group consisting of methyl and fluoro, cyano, fluoro, amino, $C_1$-$C_4$-alkylamino, and $C_1$-$C_4$-dialkylamino;

or $C_2$-$C_5$-alkynyl, which is unsubstituted or substituted by 1-2 substituents independently selected from the group consisting of $C_1$-$C_4$-fluoroalkyl, C$_3$-C$_6$-cycloalkyl, which is unsubstituted or substituted by 1-3 substituents independently selected from the group consisting of methyl and fluoro, C$_3$-C$_6$-heterocycloalkyl, which is unsubstituted or substituted by 1-3 substituents independently selected from the group consisting of methyl and fluoro, C$_1$-C$_4$-alkoxy, C$_1$-C$_4$-fluoroalkoxy, hydroxy, cyano, fluoro, amino, C$_1$-C$_4$-alkylamino, and C$_1$-C$_4$-dialkylamino;

R$^5$ and R$^6$ are independently hydrogen, deuterium or fluoro;

R$^7$ is methoxy, difluoromethoxy, trifluoromethoxy, hydroxy, fluoro or methylsulfonylamine; and R$^3$ is

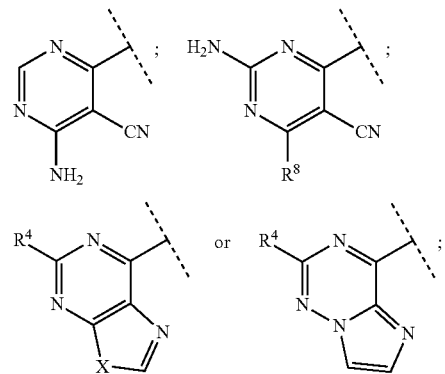

wherein

R$^4$ is hydrogen or amino,

R$^8$ is hydrogen, methyl, fluoromethyl, difluoromethyl, trideuteromethyl or amino, and X is NH, NMe or S.

5. A compound according to claim 1 or a pharmaceutically acceptable salt thereof which is a compound of formula (IA), (IB) or (IC), (IA)

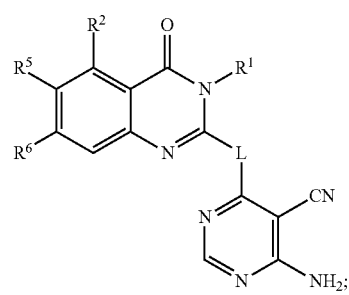

(IB)

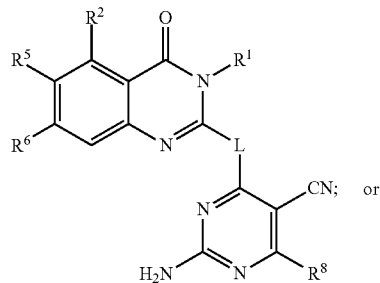

(IC)

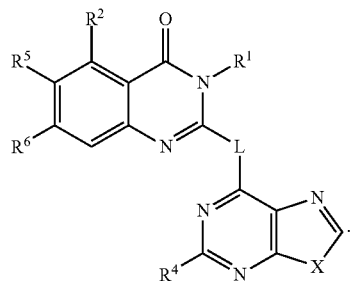

6. A compound according to claim 4, wherein R$^3$ is

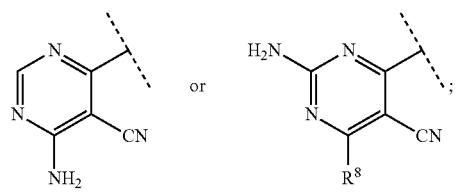

wherein

R$^8$ is methyl.

7. A compound according to claim 1 or a pharmaceutically acceptable salt thereof wherein R$^2$ is C$_5$-C$_6$-heteroaryl, containing one nitrogen atom and additional 0, 1, 2 or 3 heteroatoms independently selected from the group consisting of N, O and S, wherein C$_4$-C$_7$-heteroaryl is unsubstituted or substituted by 1-3 substituents independently selected from the group consisting of C$_1$-C$_4$-alkyl, C$_1$-C$_4$-fluoroalkyl, hydroxy-C$_1$-C$_4$-alkyl, hydroxy-C$_1$-C$_4$-fluoroalkyl, C$_1$-C$_4$-alkoxy, C$_1$-C$_4$-fluoroalkoxy, C$_3$-C$_6$-cycloalkyl, which is unsubstituted or substituted by 1-3 substituents independently selected from the group consisting of methyl and fluoro, C$_3$-C$_6$-heterocycloalkyl, which is unsubstituted or substituted by 1-3 substituents independently selected from the group consisting of methyl and fluoro, and fluoro.

8. A compound according to claim 1 or a pharmaceutically acceptable salt thereof wherein R$^1$ is phenyl, which is unsubstituted or substituted by 1, 2 or 3 substituents independently selected from the group consisting of methyl, ethyl, difluoromethyl, methoxy, difluoromethoxy, cyclopropyl, chloro and fluoro; or pyridyl, which is unsubstituted or substituted by 1, 2 or 3 substituents independently selected from the group consisting of methyl, ethyl, difluoromethyl, methoxy, difluoromethoxy, cyclopropyl, chloro and fluoro.

9. A compound according to claim 1, selected from the group consisting of

2-Amino-4-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)-6-methylpyrimidine-5-carbonitrile, (S)-4-Amino-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile, (S)-4-Amino-6-(2-(5-(2-methoxypyrimidin-5-yl)-4-oxo-3-phenyl-3,4-dihydroquinazolin-2-yl)pyrrolidin-1-yl)pyrimidine-5-carbonitrile, (S)-2-Amino-4-(2-(5-(2-methoxypyrimidin-5-yl)-4-oxo-3-phenyl-3,4-dihydroquinazolin-2-yl)pyrrolidin-1-yl)-6-methylpyrimidine-5-carbonitrile, (S)-4-Amino-6-(2-(6-fluoro-5-(1-methyl-1H-pyrazol-4-yl)-4-oxo-3-phenyl-3,4-dihydroquinazolin-2-yl)pyrrolidin-1-yl)pyrimidine-5-carbonitrile, (S)-2-Amino-4-(2-(6-fluoro-5-(1-methyl-1H-pyrazol-4-yl)-4-oxo-3-phenyl-3,4-dihydroquinazolin-2-yl)pyrrolidin-1-yl)-6-methylpyrimidine-5-carbonitrile, 2-Amino-4-((2S,4S)-2-(6-fluoro-5-(2-methoxypyrimidin-5-yl)-4-oxo-3-phenyl-3,4-dihydroquinazolin-2-yl)-4-hydroxypyrrolidin-1-yl)-6-methylpyrimidine-5-carbonitrile, 4-Amino-6-((2S,4S)-2-(6-fluoro-5-(1-methyl-1H-pyrazol-4-yl)-4-oxo-3-phenyl-3,4-dihydroquinazolin-2-yl)-4-hydroxypyrrolidin-1-yl)pyrimidine-5-carbonitrile, 2-Amino-4-((2S,4S)-2-(6-fluoro-5-(2-methoxythiazol-5-yl)-4-oxo-3-phenyl-3,4-dihydroquinazolin-2-yl)-4-hydroxypyrrolidin-1-yl)-6-methylpyrimidine-5-carbonitrile, 2-Amino-4-((2S,4S)-4-methoxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile, 2-((2S,4S)-1-(2-Amino-9H-purin-6-yl)-4-methoxypyrrolidin-2-yl)-5-(1-methyl-1H-pyrazol-4-yl)-3-phenylquinazolin-4(3H)-one, (S)-2-Amino-4-methyl-6-(2-(5-(1-methyl-1H-pyrazol-4-yl)-4-oxo-3-phenyl-3,4-dihydroquinazolin-2-yl)pyrrolidin-1-yl)pyrimidine-5-carbonitrile, (S)-4-Amino-6-(2-(5-(1-methyl-1H-pyrazol-4-yl)-4-oxo-3-(o-tolyl)-3,4-dihydroquinazolin-2-yl)pyrrolidin-1-yl)pyrimidine-5-carbonitrile, (S)-4-Amino-6-(2-(5-(1-methyl-1H-imidazol-4-yl)-4-oxo-3-phenyl-3,4-dihydroquinazolin-2-yl)pyrrolidin-1-yl)pyrimidine-5-carbonitrile, 2-Amino-4-((2S,4S)-4-hydroxy-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile, (S)-2-Amino-4-methyl-6-(2-(4-oxo-3-phenyl-5-(pyrimidin-5-yl)-3,4-dihydroquinazolin-2-yl)pyrrolidin-1-yl)pyrimidine-5-carbonitrile, (S)-2-Amino-4-(2-(5-(5-methoxypyridin-3-yl)-4-oxo-3-phenyl-3,4-dihydroquinazolin-2-yl)pyrrolidin-1-yl)-6-methylpyrimidine-5-carbonitrile, (S)-2-Amino-4-methyl-6-(2-(5-(2-methylpyrimidin-5-yl)-4-oxo-3-phenyl-3,4-dihydroquinazolin-2-yl)pyrrolidin-1-yl)pyrimidine-5-carbonitrile, (S)-2-Amino-4-methyl-6-(2-(4-oxo-3-phenyl-5-(pyridin-3-yl)-3,4-dihydroquinazolin-2-yl)pyrrolidin-1-yl)pyrimidine-5-carbonitrile, (S)-2-Amino-4-(2-(5-(6-methoxypyridin-3-yl)-4-oxo-3-phenyl-3,4-dihydroquinazolin-2-yl)pyrrolidin-1-yl)-6-methylpyrimidine-5-carbonitrile, 2-Amino-4-((2S,4S)-4-hydroxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile, 2-Amino-4-((2S,4S)-4-hydroxy-2-(5-(2-methylpyrimidin-5-yl)-4-oxo-3-phenyl-3,4-dihydroquinazolin-2-yl)pyrrolidin-1-yl)-6-methylpyrimidine-5-carbonitrile, 2-Amino-4-((2S,4S)-4-hydroxy-2-(4-oxo-3-phenyl-5-(pyridin-3-yl)-3,4-dihydroquinazolin-2-yl)pyrrolidin-1-yl)-6-methylpyrimidine-5-carbonitrile, 2-Amino-4-((2S,4S)-4-hydroxy-2-(5-(5-methoxypyridin-3-yl)-4-oxo-3-phenyl-3,4-dihydroquinazolin-2-yl)pyrrolidin-1-yl)-6-methylpyrimidine-5-carbonitrile, 2-Amino-4-((2S,4S)-4-hydroxy-2-(4-oxo-3-phenyl-5-(pyrimidin-5-yl)-3,4-dihydroquinazolin-2-yl)pyrrolidin-1-yl)-6-methylpyrimidine-5-carbonitrile, 2-Amino-4-((2S,4S)-4-hydroxy-2-(5-(4-methoxypyridin-3-yl)-4-oxo-3-phenyl-3,4-dihydroquinazolin-2-yl)pyrrolidin-1-yl)-6-methylpyrimidine-5-carbonitrile, 2-Amino-4-((2S,4S)-4-hydroxy-2-(5-(1-(2-hydroxyethyl)-1H-pyrazol-4-yl)-4-oxo-3-phenyl-3,4-dihydroquinazolin-2-yl)pyrrolidin-1-yl)-6-methylpyrimidine-5-carbonitrile, 2-Amino-4-((2S,4S)-2-(5-(2-ethoxypyrimidin-5-yl)-6-fluoro-4-oxo-3-phenyl-3,4-dihydroquinazolin-2-yl)-4-hydroxypyrrolidin-1-yl)-6-methylpyrimidine-5-carbonitrile, 2-Amino-4-((2S,4S)-4-fluoro-2-(5-(1-methyl-1H-pyrazol-4-yl)-4-oxo-3-phenyl-3,4-dihydroquinazolin-2-yl)pyrrolidin-1-yl)-6-methylpyrimidine-5-carbonitrile, 2-Amino-4-((2S,4S)-2-(6-fluoro-5-(1-methyl-1H-imidazol-4-yl)-4-oxo-3-phenyl-3,4-dihydroquinazolin-2-yl)-4-hydroxypyrrolidin-1-yl)-6-methylpyrimidine-5-carbonitrile, (S)-2-Amino-4-(2-(5-(2-ethoxypyrimidin-5-yl)-4-oxo-3-phenyl-3,4-dihydroquinazolin-2-yl)pyrrolidin-1-yl)-6-methylpyrimidine-5-carbonitrile, (S)-4-Amino-6-(2-(5-(3-hydroxyprop-1-yn-1-yl)-4-oxo-3-phenyl-3,4-dihydroquinazolin-2-yl)pyrrolidin-1-yl)pyrimidine-5-carbonitrile, and 2-Amino-4-((2S,4S)-4-methoxy-2-(5-(2-methoxypyrimidin-5-yl)-4-oxo-3-phenyl-3,4-dihydroquinazolin-2-yl)pyrrolidin-1-yl)-6-methylpyrimidine-5-carbonitrile, or a pharmaceutically acceptable salt thereof.

10. A pharmaceutical composition comprising a therapeutically effective amount of a compound according to claim 1 or a pharmaceutically acceptable salt thereof and one or more pharmaceutically acceptable carriers.

11. A combination comprising a therapeutically effective amount of a compound according to claim 1 or a pharmaceutically acceptable salt thereof and one or more therapeutically active co-agents.

12. A compound selected from a compound of the formula

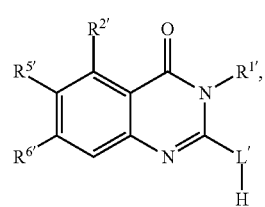

(E)

-continued

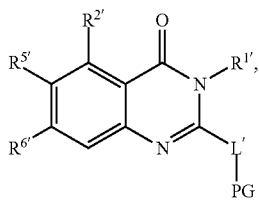
(D)

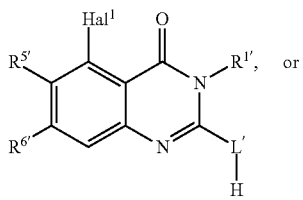
(F) or

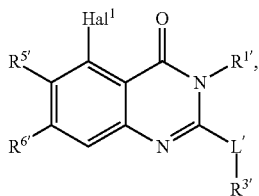
(G)

wherein
$R^{1'}$ is $R^1$, as defined for a compound of formula (I) in claim 1, or a substituent that can be transferred into $R^1$ via functionalization steps or functional group adjustment steps;
$R^{2'}$ is $R^2$, as defined for a compound of formula (I) in claim 1, or a substituent that can be transferred into $R^2$ via functionalization steps or functional group adjustment steps;
$R^{5'}$ is $R^5$, defined for a compound of formula (I) in claim 1, or a substituent that can be transferred into $R^5$ via functionalization steps or functional group adjustment steps;
$R^{6'}$ is $R^6$, as defined for a compound of formula (I) in claim 1, or a substituent that can be transferred into $R^6$ via functionalization steps or functional group adjustment steps; and
L' is L, as defined for a compound of formula (I) in claim 1, or a substituent that can be transferred into L via functionalization steps or functional group adjustment steps;
PG represents a suitable protecting group;
$Hal^1$ represents a halogen.

13. A process or method for the manufacture of a compound of formula (I) or a pharmaceutically acceptable salt thereof according to claim 1,
comprising the steps of method A:
d1) coupling a compound of formula (E),

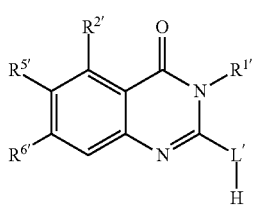
(E)

wherein
$R^{1'}$ is $R^1$, as defined for a compound of formula (I) in claim 1, or a substituent that can be transferred into $R^1$ via functionalization steps or functional group adjustment steps;
$R^{2'}$ is $R^2$, as defined for a compound of formula (I) in claim 1, or a substituent that can be transferred into $R^2$ via functionalization steps or functional group adjustment steps;
$R^{5'}$ is $R^5$, as defined for a compound of formula (I) in claim 1, or a substituent that can be transferred into $R^5$ via functionalization steps or functional group adjustment steps;
$R^{6'}$ is $R^6$, as defined for a compound of formula (I) in claim 1, or a substituent that can be transferred into $R^6$ via functionalization steps or functional group adjustment steps; and
L' is L, as defined for a compound of formula (I) in claim 1, or a substituent that can be transferred into L via functionalization steps or functional group adjustment steps;
with $R^{3'}$-Hal wherein $R^{3'}$ is $R^3$, as defined for a compound of formula (I) in claim 1, or a substituent that can be transferred into $R^3$ via functionalization steps or functional group adjustment steps;

and Hal represents halogen;

in the presence of an amine base with heating, or under customary Buchwald-Hartwig conditions using a suitable Pd catalyst/ligand combination and a suitable base and an organic solvent;

optionally followed by functionalization steps or functional group adjustment steps d1);

wherein the compound of formula (E) is prepared comprising the step c1) of deprotecting PG from the compound of formula (D),

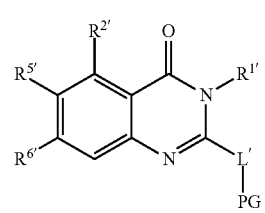
(D)

wherein PG represents a suitable protecting group, and the other substituents are as defined for a compound of formula (E);

optionally followed by functionalization steps or functional group adjustment steps c1'), wherein the compound of formula (D) is prepared comprising the step b1) of coupling the compound of formula (C),

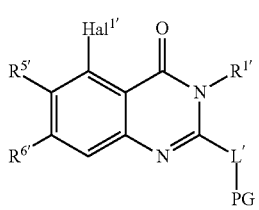

wherein Hal$^1$ represents a halogen or a pseudohalogen, and the other substituents are as defined for the compound of formula (D);
with

R$^{2'}$-Y wherein when R$^{2'}$ is C$_4$-C$_7$-heteroaryl, as defined for R$^2$ for a compound of formula (I) in claim 1, or a substituent that can be transferred into C$_4$-C$_7$-heteroaryl, via functionalization steps or functional group adjustment steps, Y represents a boronic acid residue or a cyclic or acyclic borolanyl; or an alkylstannyl;

or wherein when R$^{2'}$ is C$_2$-C$_5$-alkynyl, as defined for R$^2$ for a compound of formula (I) in claim 1, or a substituent that can be transferred into C$_2$-C$_5$-alkynyl, via functionalization steps or functional group adjustment steps, Y is H (for a terminal alkyne) or Y represents an alkylstannyl (non terminal alkyne) under customary reaction conditions of the Suzuki reaction (Y is boronic acid residue or a cyclic or acyclic boronate ester), the Stille reaction (Y is alkylstannyl) or the Sonogashira coupling (Y is H of a terminal alkyne);

optionally followed by functionalization steps or functional group adjustment steps b1');

wherein the compound of formula (C) is prepared comprising the step a) of reacting a compound of formula (A),

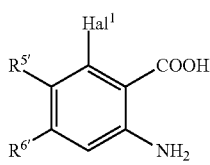

wherein the substituents are as defined for the compound of formula (C);
with a compound of formula (B),

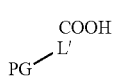

wherein the substituents are as defined for the compound of formula (C);
followed by reaction with R$^{1'}$—NH$_2$
wherein R$^{1'}$ is as defined for a compound of formula (E);
optionally followed by functionalization steps or functional group adjustment steps a');

or alternatively comprising the steps of method B:

d1) coupling a compound of formula (E),

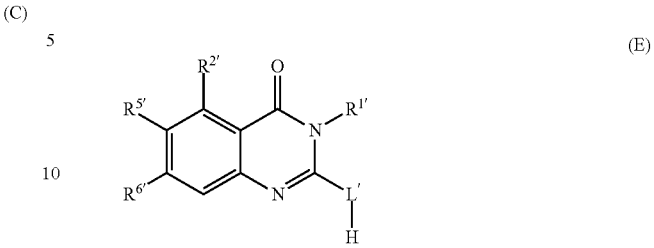

wherein

R$^{1'}$ is R$^1$, as defined for a compound of formula (I) in claim 1, or a substituent that can be transferred into R$^1$ via functionalization steps or functional group adjustment steps;

R$^{2'}$ is R$^2$, as defined for a compound of formula (I) in claim 1, or a substituent that can be transferred into R$^2$ via functionalization steps or functional group adjustment steps;

R$^{5'}$ is R$^5$, as defined for a compound of formula (I) in claim 1, or a substituent that can be transferred into R$^5$ via functionalization steps or functional group adjustment steps;

R$^{6'}$ is R$^6$, as defined for a compound of formula (I) in claim 1, or a substituent that can be transferred into R$^6$ via functionalization steps or functional group adjustment steps; and L' is L, as defined for a compound of formula (I) in claim 1, or a substituent that can be transferred into L via functionalization steps or functional group adjustment steps;

with

R$^{3'}$-Hal wherein R$^{3'}$ is R$^3$, as defined for a compound of formula (I) in claim 1, or a substituent that can be transferred into R$^3$ via functionalization steps or functional group adjustment steps;

and Hal represents halogen;

in the presence of an amine base with heating, or under customary Buchwald-Hartwig conditions using a suitable Pd catalyst/ligand combination and a suitable base and an organic solvent;

optionally followed by functionalization steps or functional group adjustment steps d1);

wherein the compound of formula (E) is prepared comprising the step c2) of coupling a compound of formula (F),

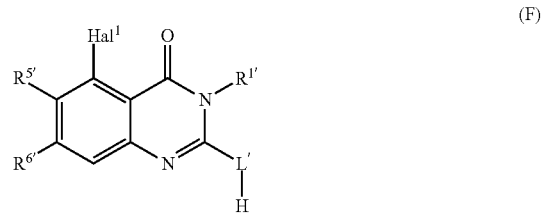

wherein Hal¹ represents a halogen, or a pseudohalogen, and the other substituents are as defined for the compound of formula (E);

with $R^{2'}$—Y wherein when $R^{2'}$ is $C_4$-$C_7$-heteroaryl, as defined for $R^2$ for a compound of formula (I) in claim 1, or a substituent that can be transferred into $C_4$-$C_7$-heteroaryl, via functionalization steps or functional group adjustment steps, Y represents a boronic acid residue or a cyclic or acyclic borolanyl; or an alkylstannyl;

wherein when $R^{2'}$ is $C_2$-$C_5$-alkynyl, as defined for $R^2$ for a compound of formula (I) in claim 1, or a substituent that can be transferred into $C_2$-$C_5$-alkynyl, via functionalization steps or functional group adjustment steps, Y is H (for a terminal alkyne) or Y represents an alkylstannyl (non terminal alkyne) under customary reaction conditions of the Suzuki reaction (Y is boronic acid residue or a cyclic or acyclic borolanyl), the Stille reaction (Y is alkylstannyl) or the Sonogashira coupling (Y is H of a terminal alkyne);

optionally followed by functionalization steps or functional group adjustment steps c2');

wherein the compound of formula (F) is prepared comprising the step b2) of deprotecting PG from the compound of formula (C),

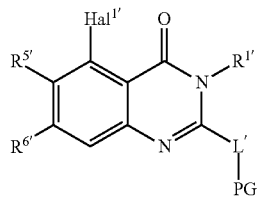

(C)

wherein PG represents a suitable protecting group, and the other substituents are as defined for the compound of formula (F);

optionally followed by functionalization steps or functional group adjustment steps b2');

wherein the compound of formula (C) is prepared comprising the step a) of reacting a compound of formula (A),

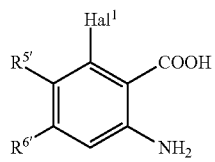

(A)

wherein the substituents are as defined for the compound of formula (C);

with a compound of formula (B),

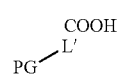

(B)

wherein the substituents are as defined for the compound of formula (C);

followed by reaction with $R^{1'}$—$NH_2$ wherein $R^{1'}$ is as defined for a compound of formula (E);

optionally followed by functionalization steps or functional group adjustment steps a');

or alternatively comprising the steps of method C:

d2) coupling a compound of formula (G),

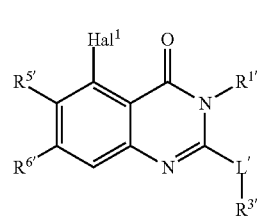

(G)

wherein

Hal¹ represents a halogen or a pseudohalogen;

$R^{1'}$ is $R^1$, as defined for a compound of formula (I) in claim 1, or a substituent that can be transferred into $R^1$ via functionalization steps or functional group adjustment steps;

$R^{5'}$ is $R^5$, as defined for a compound of formula (I) in claim 1, or a substituent that can be transferred into $R^5$ via functionalization steps or functional group adjustment steps;

$R^{6'}$ is $R^6$, as defined for a compound of formula (I) in claim 1, or a substituent that can be transferred into $R^6$ via functionalization steps or functional group adjustment steps; and L' is L, as defined for a compound of formula (I) in claim 1, or a substituent that can be transferred into L via functionalization steps or functional group adjustment steps;

with $R^{2'}$—Y wherein when $R^{2'}$ is $C_4$-$C_7$-heteroaryl, as defined for $R^2$ for a compound of formula (I) in claim 1, or a substituent that can be transferred into $C_4$-$C_7$-heteroaryl, via functionalization steps or functional group adjustment steps, Y represents a boronic acid residue or a cyclic or acyclic borolanyl; or an alkylstannyl;

wherein when $R^{2'}$ is $C_2$-$C_5$-alkynyl, as defined for $R^2$ for a compound of formula (I) in claim 1, or a substituent that can be transferred into $C_2$-$C_5$-alkynyl, via functionalization steps or functional group adjustment steps, Y is H (for a terminal alkyne) or Y represents an alkylstannyl (non terminal alkyne) under customary reaction conditions of the Suzuki reaction (Y is boronic acid residue or a cyclic or acyclic borolanyl), the Stille reaction (Y is alkylstannyl) or the Sonogashira coupling (Y is H of a terminal alkyne);

optionally followed by functionalization steps or functional group adjustment steps d2');

wherein the compound of formula (G) is prepared comprising the step c3) of coupling the compound of formula (F),

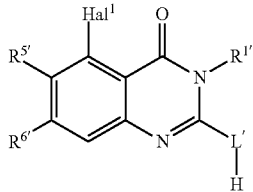

(F)

wherein the substituents are as defined for a compound of formula (G);
with

R3'-Hal wherein

R$^{3'}$ is R$^3$, as defined for a compound of formula (I) in claim 1, or a substituent that can be transferred into R$^3$ via functionalization steps or functional group adjustment steps; and Hal represents halogen;

in the presence of an amine base with heating, or under customary Buchwald-Hartwig conditions using a suitable Pd catalyst/ligand combination and a suitable base and an organic solvent;

optionally followed by functionalization steps or functional group adjustment steps c3');

wherein the compound of formula (F) is prepared comprising the step b2) of deprotecting PG from the compound of formula (C),

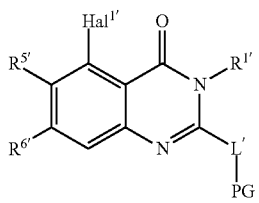

(C)

wherein PG represents a suitable protecting group, and the other substituents are as defined defined for a compound of formula (F);

optionally followed by functionalization steps or functional group adjustment steps b2')

wherein the compound of formula (C) is prepared comprising the step a) of reacting a compound of formula (A),

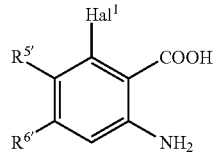

(A)

wherein the substituents are as defined for a compound of formula (C);

with a compound of formula (B),

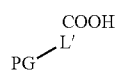

(B)

wherein the substituents are as defined for a compound of formula (C);

followed by reaction with R$^{1'}$—NH$_2$ wherein R$^{1'}$ is as defined for a compound of formula (C);

optionally followed by functionalization steps or functional group adjustment steps a').

14. A method of modulating the activity of the class I PI3 kinases, in a subject, wherein the method comprises administering to the subject a therapeutically effective amount of a compound according to claim 1 or a pharmaceutically acceptable salt thereof.

15. A method of treating a disorder or a disease selected from the group consisting of rheumatoid arthritis (RA), pemphigus vulgaris (PV), endemic form of Brazilian pemphigus (Fogo selvagem), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS) (such as primary Sjögren's syndrom (pSS)), ANCA-associated vasculitides (such as Wegener disease, microscopic polyangiitis or Churg-Strauss syndrome), cryoglobulinemia, ischemia-reperfusion injury, chronic autoimmune urticaria (CAU), allergy (atopic dermatitis, contact dermatitis, allergic rhinitis), Goodpasture's syndrome, transplant rejection, severe and cerebral malaria, trypanosomiasis, leishmaniasis, toxoplasmosis and neurocysticercosis comprising administering to a subject a therapeutically effective amount of a compound according to claim 1 or a pharmaceutically acceptable salt thereof.

* * * * *